United States Patent
Skipper et al.

(10) Patent No.: US 9,132,255 B2
(45) Date of Patent: Sep. 15, 2015

(54) CUSHIONING STRUCTURE

(75) Inventors: Christopher Scott Skipper, North Ryde (AU); Matthew David Spruell, Bella Vista (AU); Joshua Adam Gudiksen, Mortdale (AU); Fiona Catherine Carroll, Concord (AU); Johannes Nickol, Matinsried (DE); Johann Sebastian Burz, Martinsried (DE); Achim Biener, Munich (DE); Bernd Christoph Lang, Gräfelfing (DE); Teresa Wang, Bella Vista (AU)

(73) Assignee: ResMed Limited, Bella Vista (AU)

( * ) Notice: Subject to any disclaimer, the term of this patent is extended or adjusted under 35 U.S.C. 154(b) by 584 days.

(21) Appl. No.: 12/734,670

(22) PCT Filed: Nov. 17, 2008

(86) PCT No.: PCT/AU2008/001711
§ 371 (c)(1),
(2), (4) Date: Nov. 29, 2010

(87) PCT Pub. No.: WO2009/062265
PCT Pub. Date: May 22, 2009

(65) Prior Publication Data
US 2011/0088699 A1    Apr. 21, 2011

(30) Foreign Application Priority Data

Nov. 15, 2007 (AU) ............................. 2007906253
Nov. 16, 2007 (AU) ............................. 2007906271
Jan. 4, 2008 (AU) ............................. 2008900072
Mar. 14, 2008 (AU) ............................. 2008901271
May 29, 2008 (AU) ............................. 2008902720
Jun. 27, 2008 (AU) ............................. 2008903294
Jul. 22, 2008 (EP) ..................................... 08160921

(51) Int. Cl.
*A62B 18/08* (2006.01)
*A61M 16/06* (2006.01)
(Continued)

(52) U.S. Cl.
CPC ........... *A61M 16/06* (2013.01); *A61M 16/0616* (2014.02); *A61M 16/0622* (2014.02);
(Continued)

(58) Field of Classification Search
CPC ............ A61M 16/06; A61M 16/0616; A61M 16/0622; A61M 2016/0661
USPC ............. 128/206.21, 206.24, 206.26, 206.23, 128/206.28, 207.13
See application file for complete search history.

(56) References Cited

U.S. PATENT DOCUMENTS 3,330,273 A    7/1967   Bennett
4,907,584 A *  3/1990   McGinnis ................ 128/206.24
(Continued)

FOREIGN PATENT DOCUMENTS

CN    1 735 439        2/2006
EP    0427474 A2       5/1991
(Continued)

OTHER PUBLICATIONS

International Preliminary Report on Patentability issued in Appln. No. PCT/AU2008/001711 (May 18, 2010).
(Continued)

*Primary Examiner* — Melanie Hand
*Assistant Examiner* — Aundria Hairell
(74) *Attorney, Agent, or Firm* — Nixon & Vanderhye P.C.

(57) ABSTRACT

A patient interface includes a cushioning structure including at least one hollow chamber filled with first and second discrete and/or layered filling materials and a seal forming structure formed in one piece with the cushioning structure. The seal forming structure includes a thin membrane flap that is structured to provide a seal to the patient's face. The chamber extends only around a portion of the perimeter of the cushioning structure such that the chamber with first and second filling materials is provided in cheek and lip regions of the cushioning structure and a solid silicone portion is provided in a nasal bridge region of the cushioning structure.

17 Claims, 71 Drawing Sheets

(51) Int. Cl.

| | | |
|---|---|---|
| B29C 45/00 | (2006.01) | |
| B29C 65/02 | (2006.01) | |
| B29C 65/04 | (2006.01) | |
| B29C 65/48 | (2006.01) | |
| B29C 65/00 | (2006.01) | |
| B29C 67/24 | (2006.01) | |
| B29C 69/00 | (2006.01) | |
| B29K 75/00 | (2006.01) | |
| B29K 83/00 | (2006.01) | |
| B29K 105/00 | (2006.01) | |
| B29K 283/00 | (2006.01) | |
| B29L 22/02 | (2006.01) | |
| B29L 31/48 | (2006.01) | |

(52) U.S. Cl.
CPC ........ *A61M16/0638* (2014.02); *B29C 45/0001* (2013.01); *B29C 65/02* (2013.01); *B29C 65/028* (2013.01); *B29C 65/04* (2013.01); *B29C 65/48* (2013.01); *B29C 66/21* (2013.01); *B29C 66/324* (2013.01); *B29C 67/246* (2013.01); *B29C 69/004* (2013.01); *B29K 2075/00* (2013.01); *B29K 2083/00* (2013.01); *B29K 2105/0061* (2013.01); *B29K 2283/00* (2013.01); *B29L 2022/025* (2013.01); *B29L 2031/4835* (2013.01)

(56) References Cited

U.S. PATENT DOCUMENTS

| | | | |
|---|---|---|---|
| 4,944,310 A | 7/1990 | Sullivan | |
| 5,560,354 A | 10/1996 | Berthon-Jones et al. | |
| 5,884,624 A | 3/1999 | Barnett et al. | |
| 6,019,101 A | 2/2000 | Cotner et al. | |
| 6,082,360 A | 7/2000 | Rudolph et al. | |
| 6,196,223 B1 | 3/2001 | Belfer et al. | |
| 6,397,847 B1 * | 6/2002 | Scarberry et al. | 128/206.24 |
| 6,467,483 B1 | 10/2002 | Kopacko et al. | |
| 6,615,832 B1 | 9/2003 | Chen | |
| 6,631,718 B1 | 10/2003 | Lovell | |
| 6,907,882 B2 | 6/2005 | Ging et al. | |
| 7,216,647 B2 * | 5/2007 | Lang et al. | 128/206.24 |
| 2002/0100479 A1 | 8/2002 | Scarberry et al. | |
| 2003/0168063 A1 | 9/2003 | Gambone et al. | |
| 2005/0199239 A1 | 9/2005 | Lang et al. | |
| 2006/0076018 A1 | 4/2006 | Barnett et al. | |
| 2007/0163594 A1 | 7/2007 | Ho et al. | |
| 2007/0221227 A1 | 9/2007 | Ho | |
| 2008/0149104 A1 | 6/2008 | Eifler | |
| 2008/0289633 A1 | 11/2008 | Kwok et al. | |
| 2010/0018534 A1 | 1/2010 | Veliss et al. | |
| 2010/0294281 A1 | 11/2010 | Ho | |
| 2011/0088698 A1 | 4/2011 | Barnett et al. | |
| 2011/0088699 A1 | 4/2011 | Skipper et al. | |
| 2011/0162654 A1 | 7/2011 | Carroll et al. | |

FOREIGN PATENT DOCUMENTS

| | | |
|---|---|---|
| EP | 0935971 A2 | 8/1999 |
| EP | 08160921.6 | 7/2008 |
| JP | 09207152 | 8/1997 |
| JP | 09216240 | 8/1997 |
| JP | 2002-526180 | 8/2002 |
| JP | 2005-529687 | 10/2005 |
| WO | WO 03/016018 | 2/2003 |
| WO | WO 2004/007010 | 1/2004 |
| WO | WO 2007/009182 | 1/2007 |
| WO | WO 2007/045023 | 4/2007 |
| WO | WO 2007/104042 | 9/2007 |
| WO | WO 2009/062265 | 5/2009 |

OTHER PUBLICATIONS

Office Action issued in a corresponding Japanese Application No. 2010-533389 (Jan. 22, 2013) with English translation thereof.
Patent Examination Report issued in a corresponding Australian Appl. No. 2008323541, dated Feb. 21, 2013.
Office Action issued in a corresponding Chinese Application No. 200880116496.1, dated Nov. 29, 2013, with English language translation thereof.
Office Action issued in a corresponding Chinese Appl. No. 200880116496.1, dated Jul. 18, 2013, with English translation thereof.
Extended European Search Report issued in a corresponding EP Application No. 08849633.6, dated Dec. 4, 2013.
Office Action issued in related U.S. Appl. No. 12/736,980 dated Sep. 4, 2014.
Office Action issued in related Chinese Appln. No. 200980119658.1 dated Jun. 20, 2014, with English Translation.
International Search Report issued in Appln. No. PCT/AU2008/001711 (Mar. 13, 2009).
Extended European Search Report issued in related European Appln. No. 09 75 3350.9 dated Apr. 24, 2015.

* cited by examiner

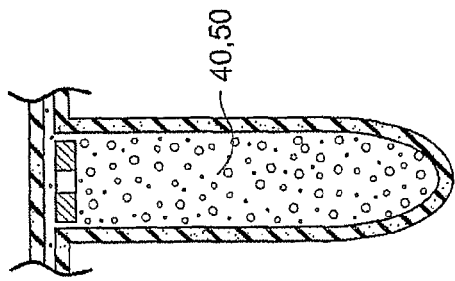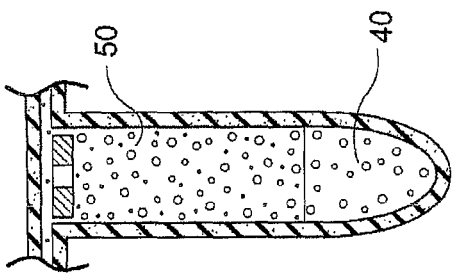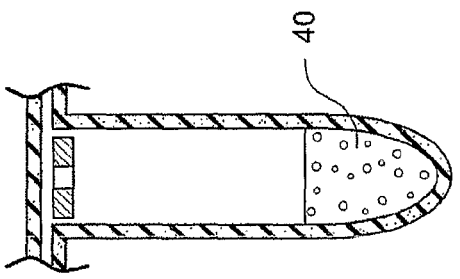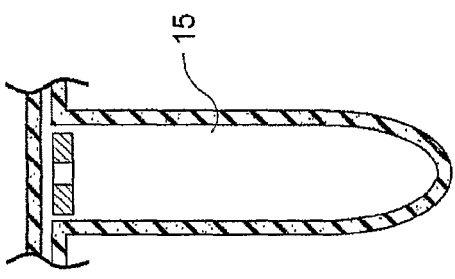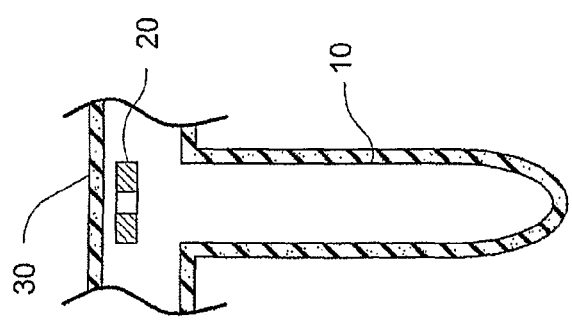

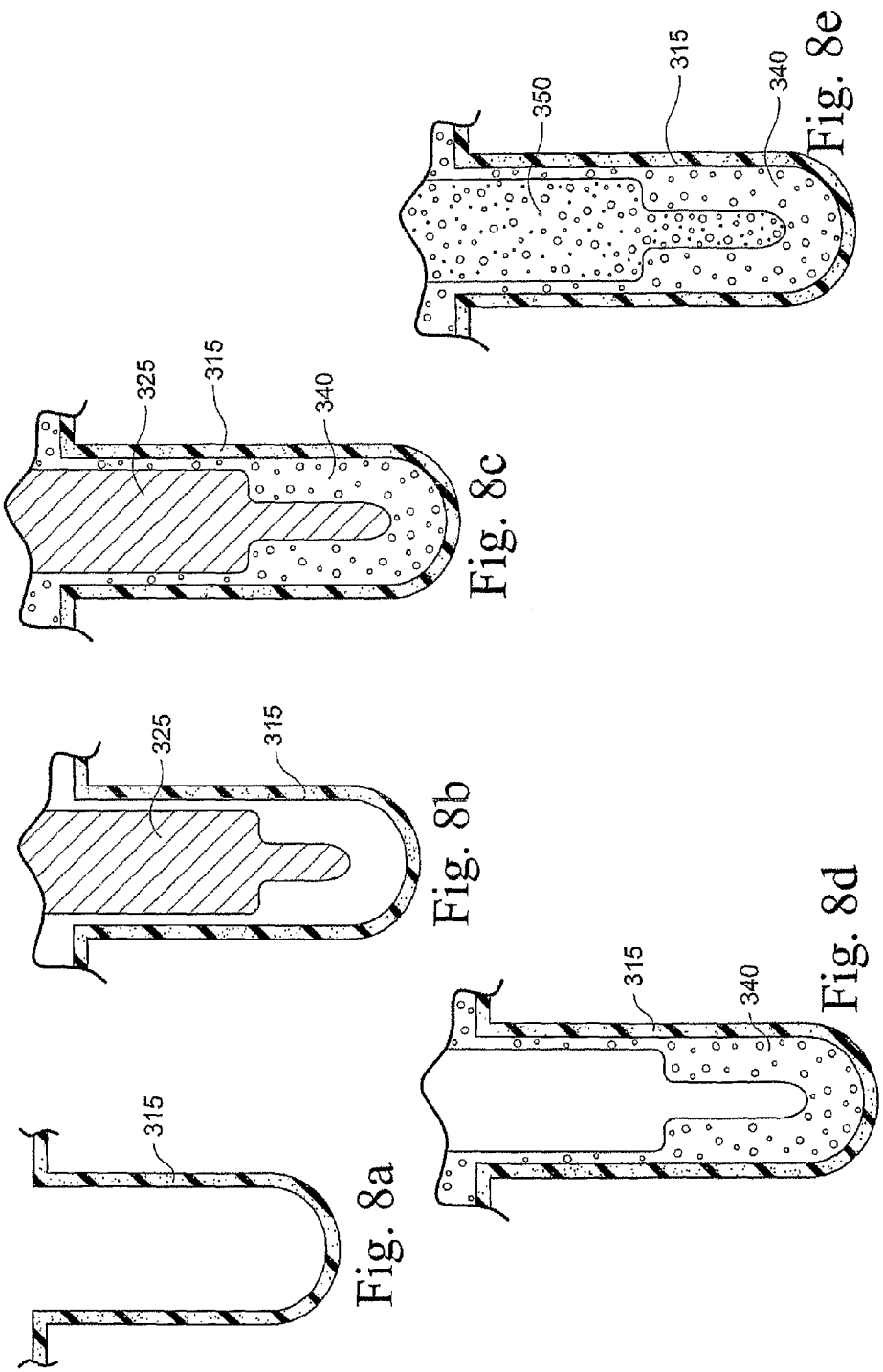

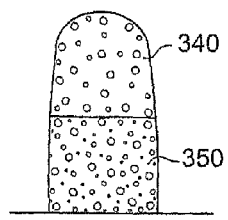
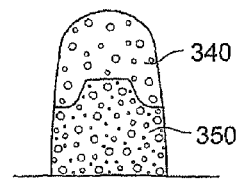
Fig. 10a   Fig. 10b
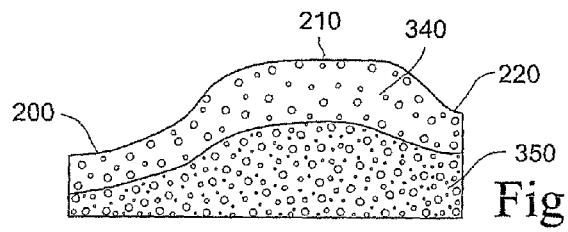
Fig. 11a
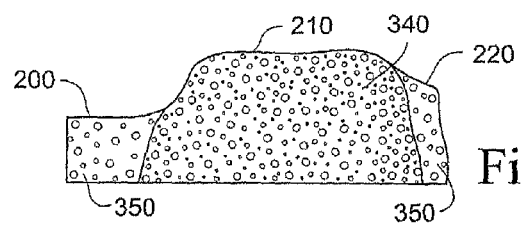
Fig. 11b
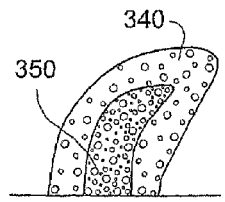 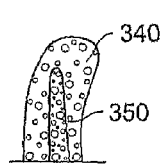 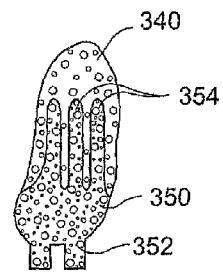
Fig. 12a   Fig. 12b   Fig. 13a
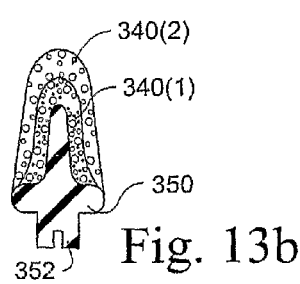 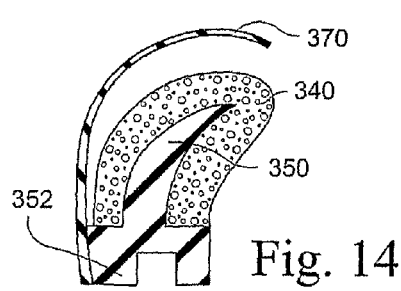
Fig. 13b   Fig. 14

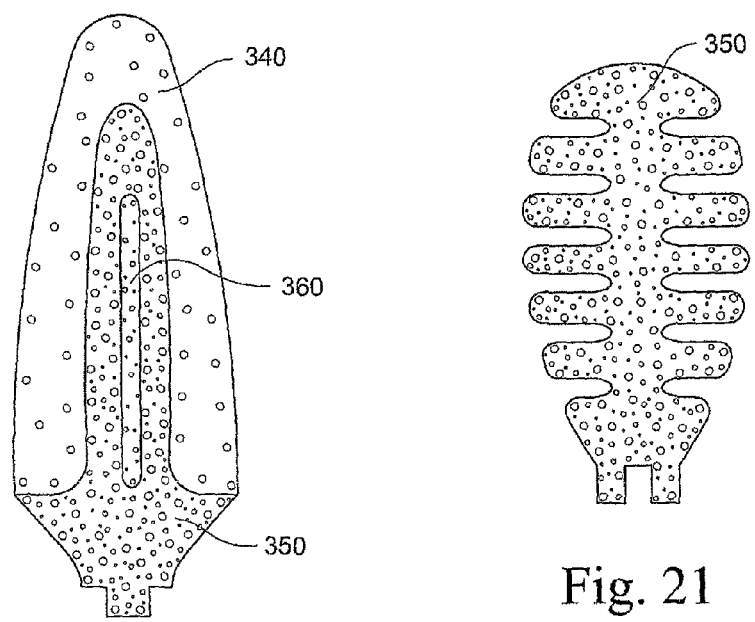
Fig. 20
Fig. 21
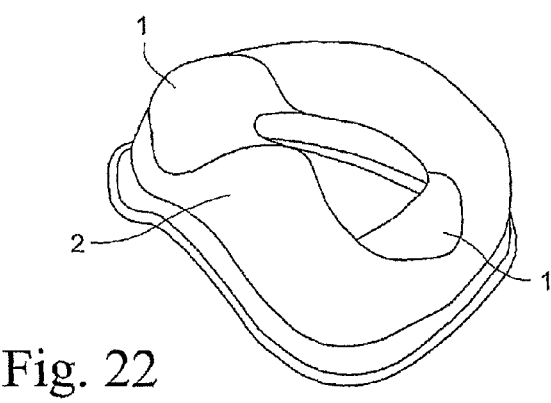
Fig. 22

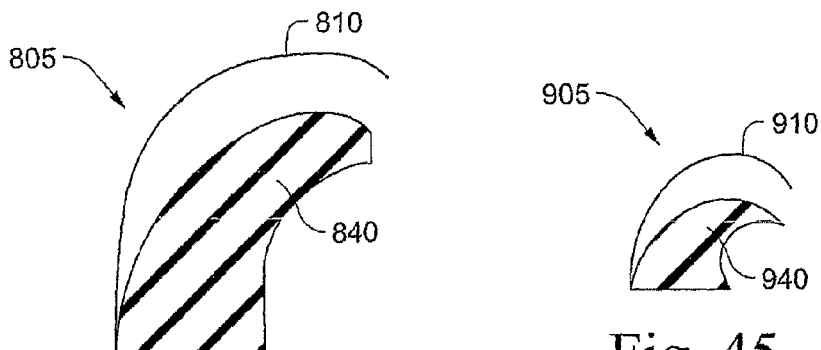
Fig. 44
Fig. 45
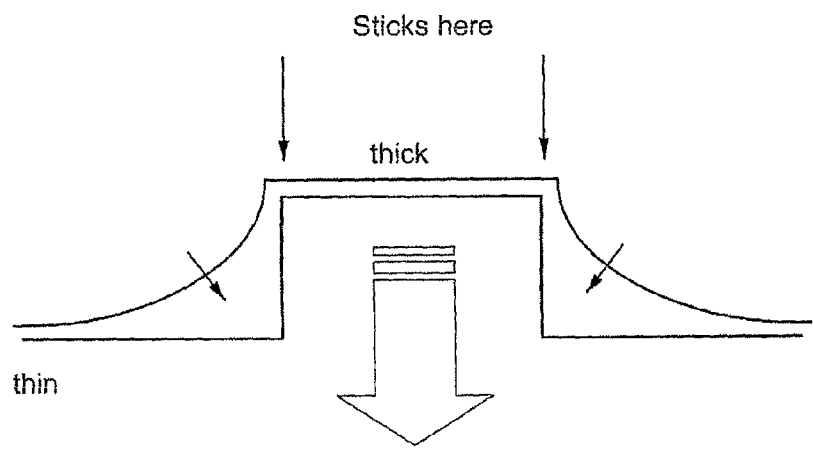
Fig. 46
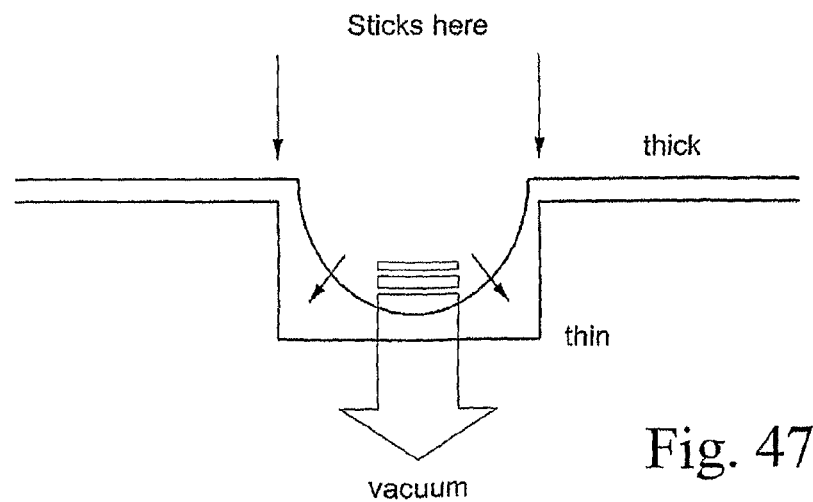
Fig. 47

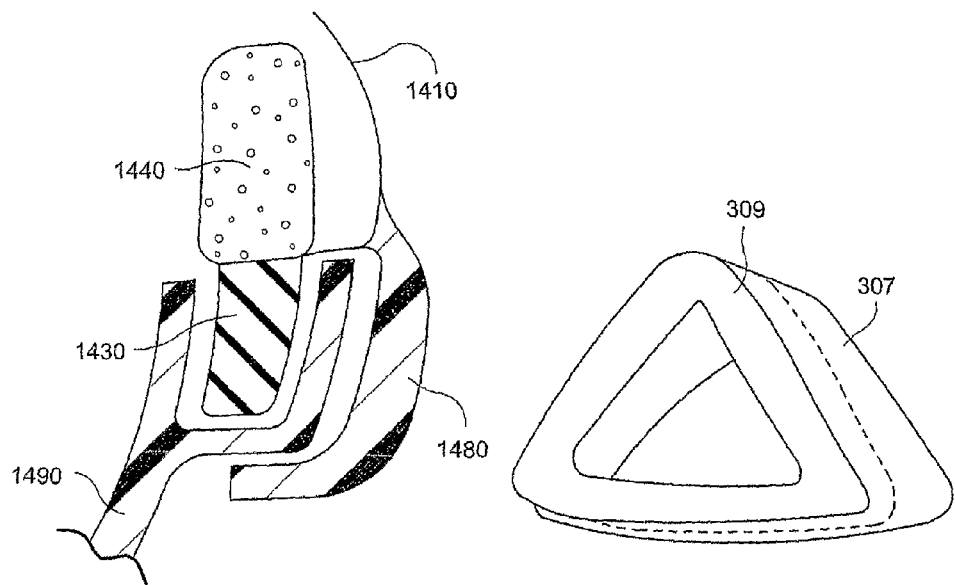
Fig. 52
Fig. 53
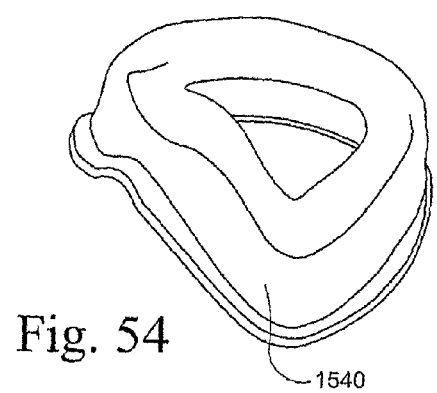
Fig. 54

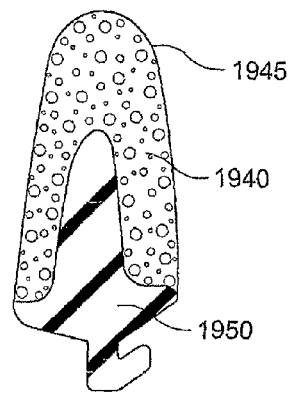
Fig. 60
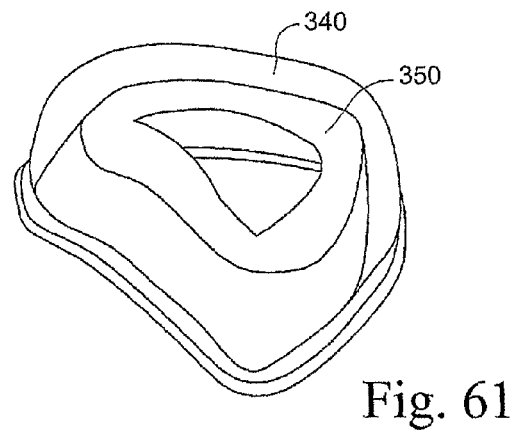
Fig. 61
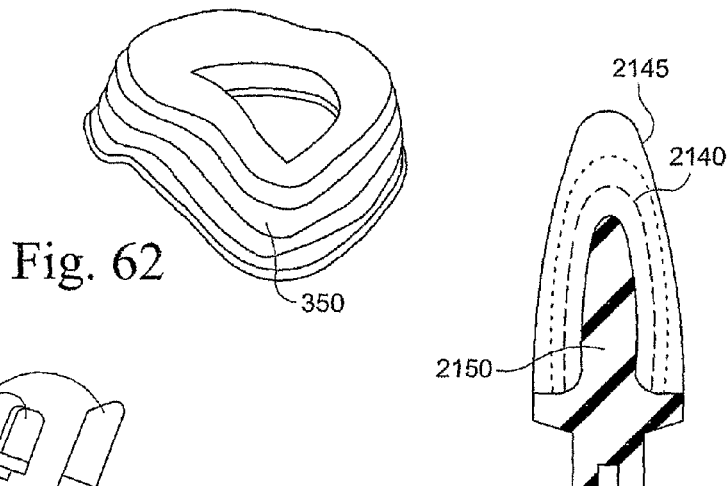
Fig. 62
Fig. 64
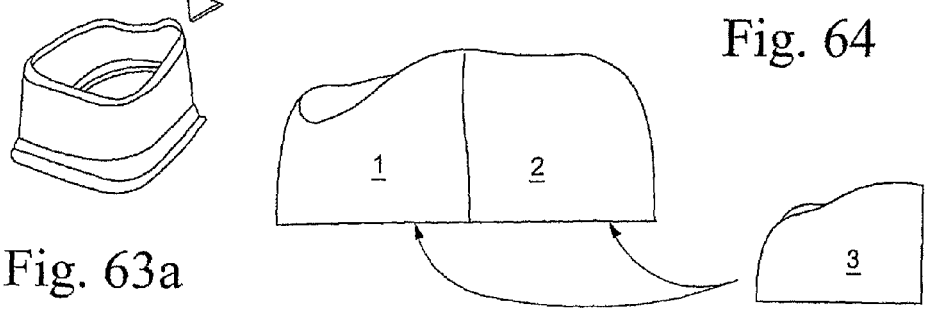
Fig. 63a
Fig. 63b

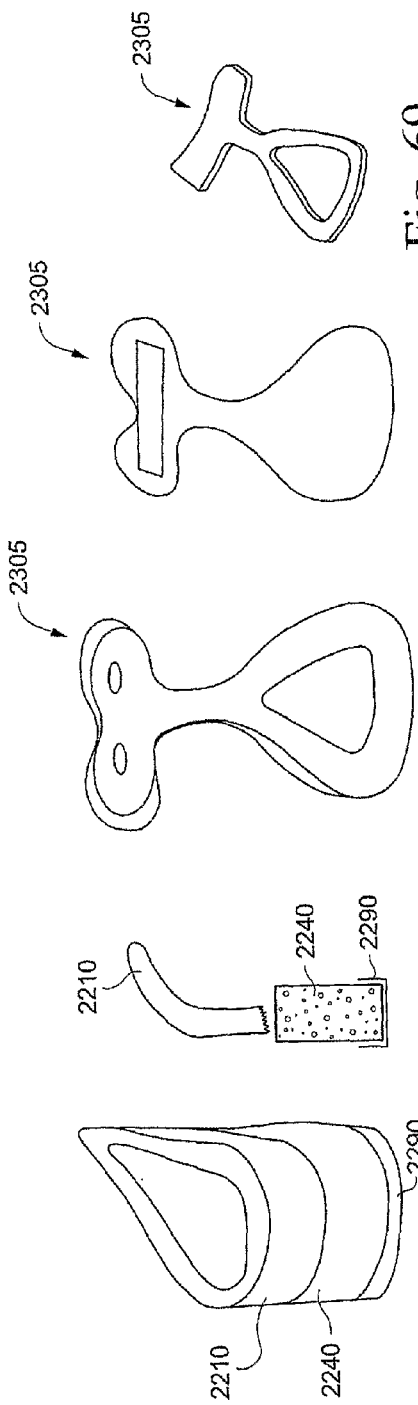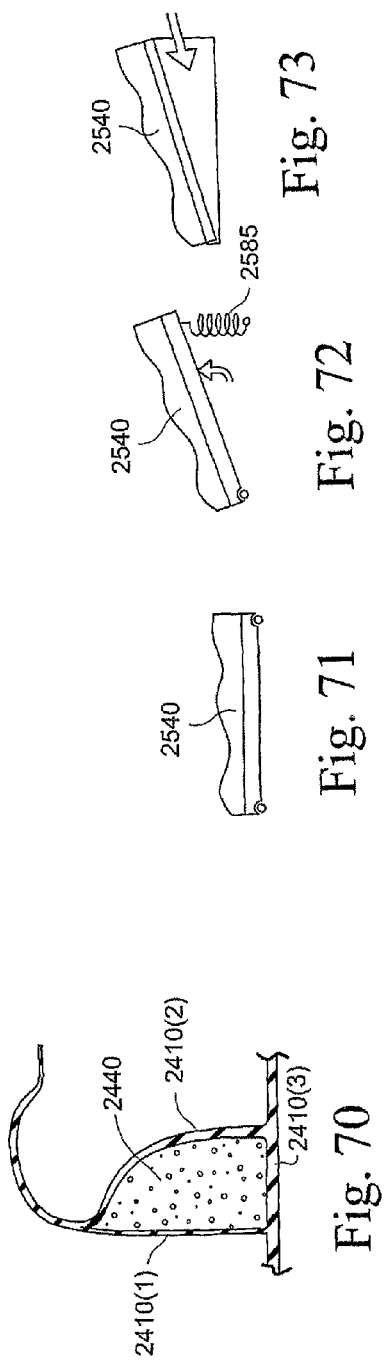

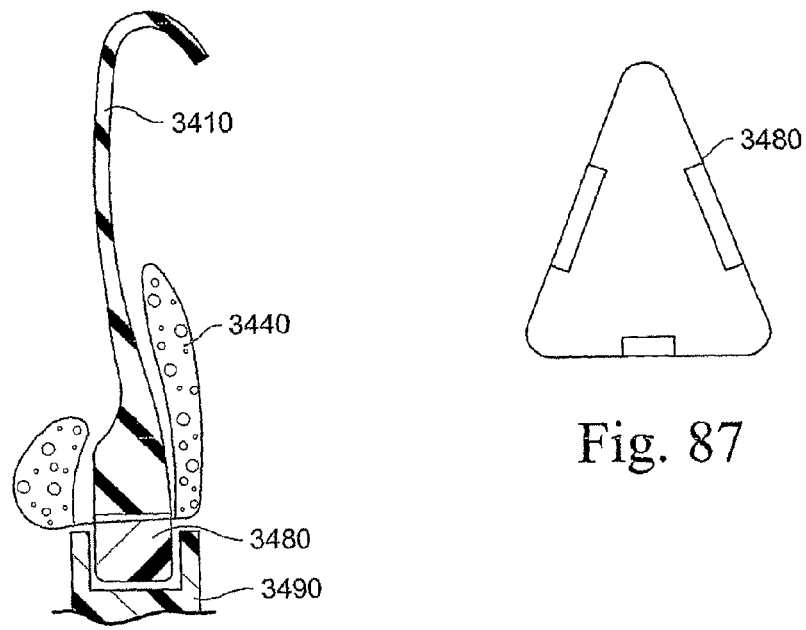
Fig. 86
Fig. 87
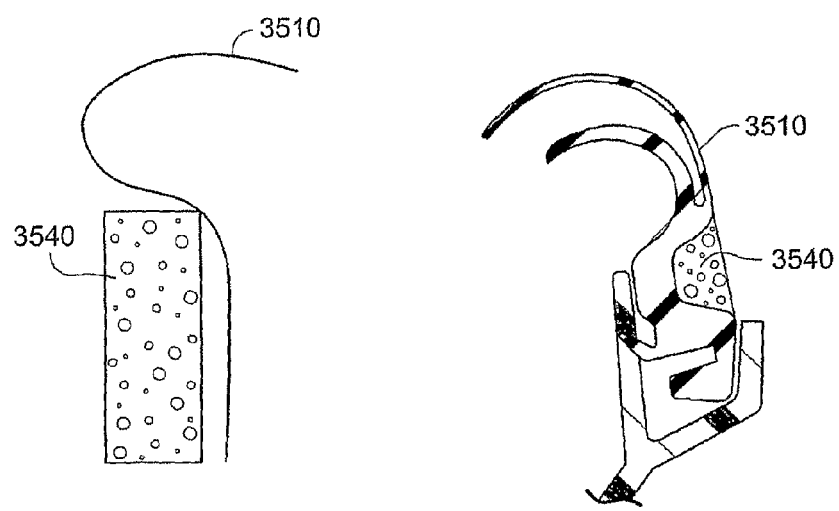
Fig. 88
Fig. 89

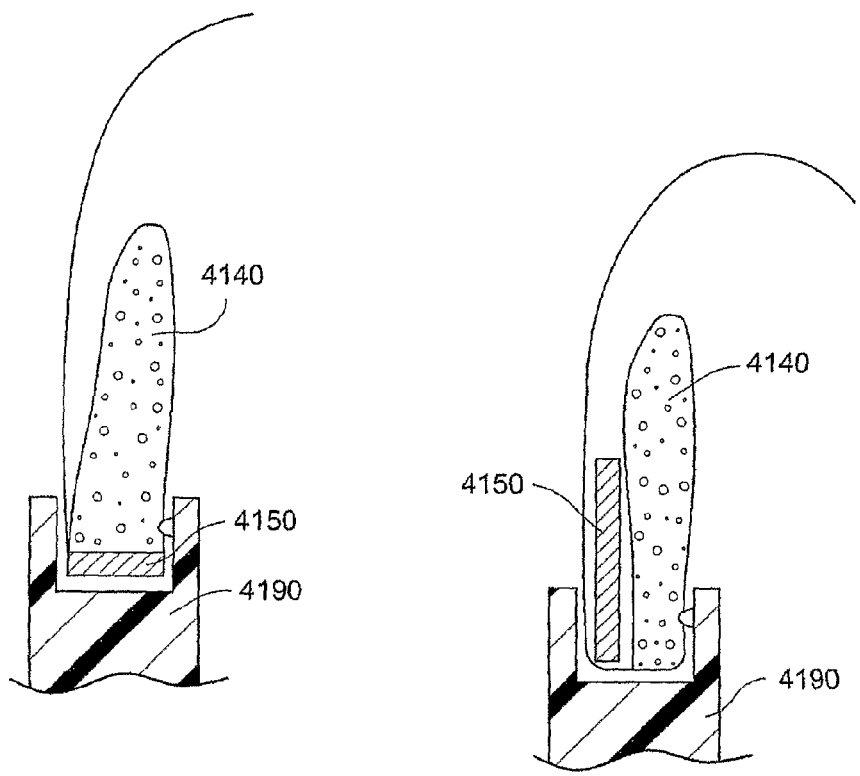
Fig. 99
Fig. 100
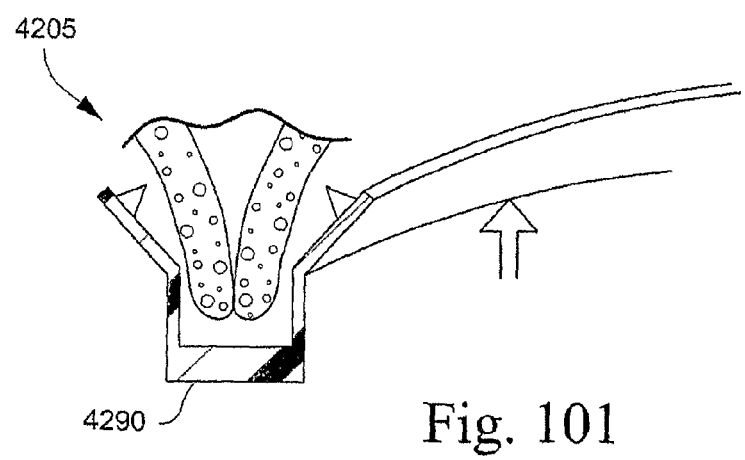
Fig. 101

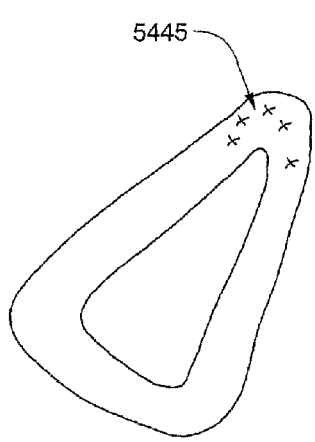
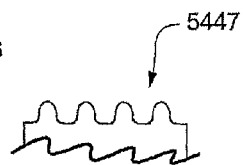
Fig. 118   Fig. 119
Fig. 117
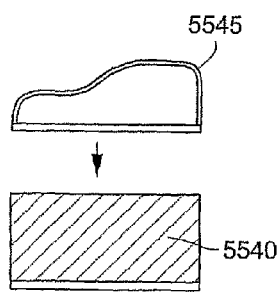
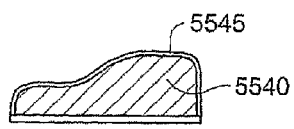
Fig. 121
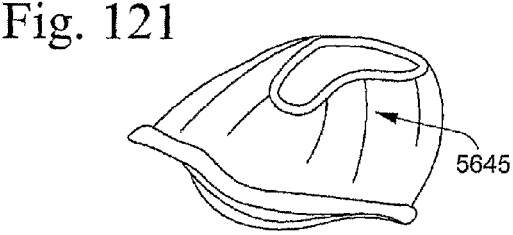
Fig. 120   Fig. 122
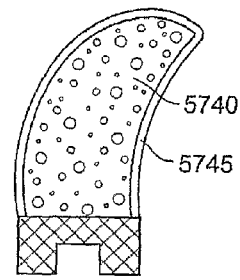
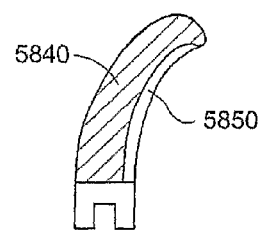
Fig. 123   Fig. 124

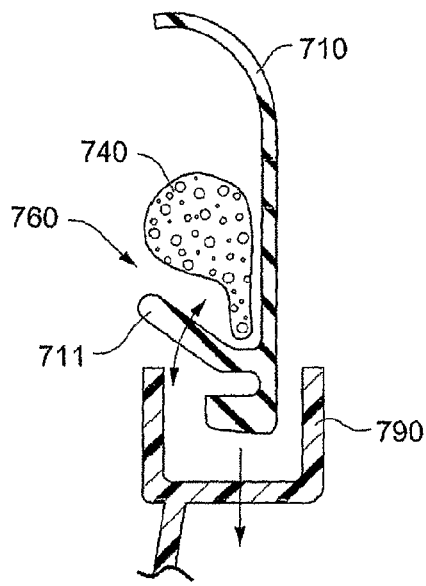
Fig. 151
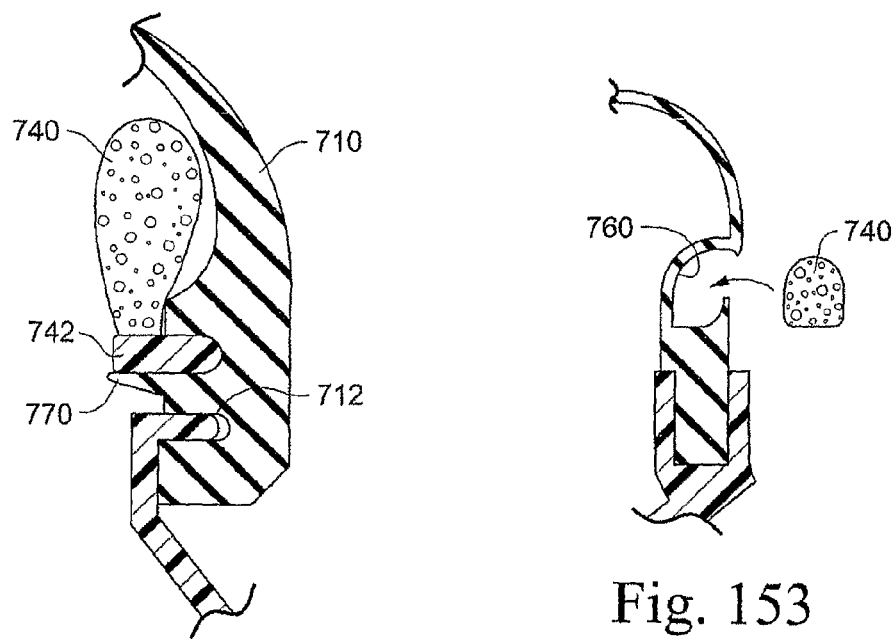
Fig. 152
Fig. 153

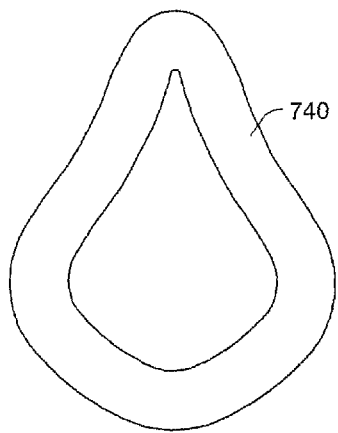
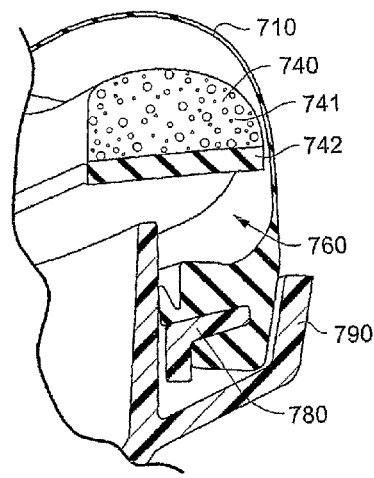
Fig. 154　　　Fig. 155
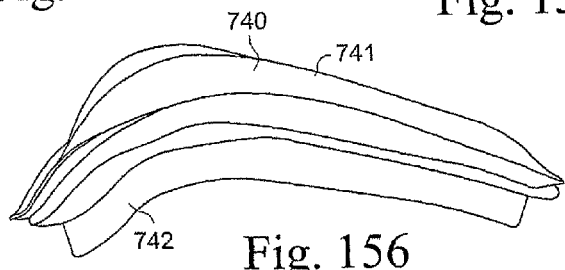
Fig. 156
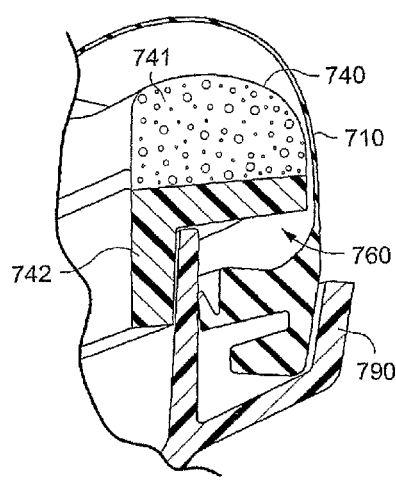
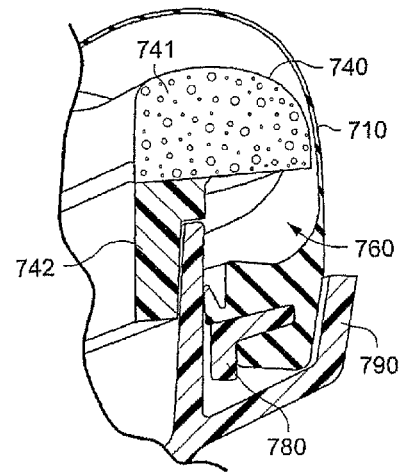
Fig. 157A　　　Fig. 157B

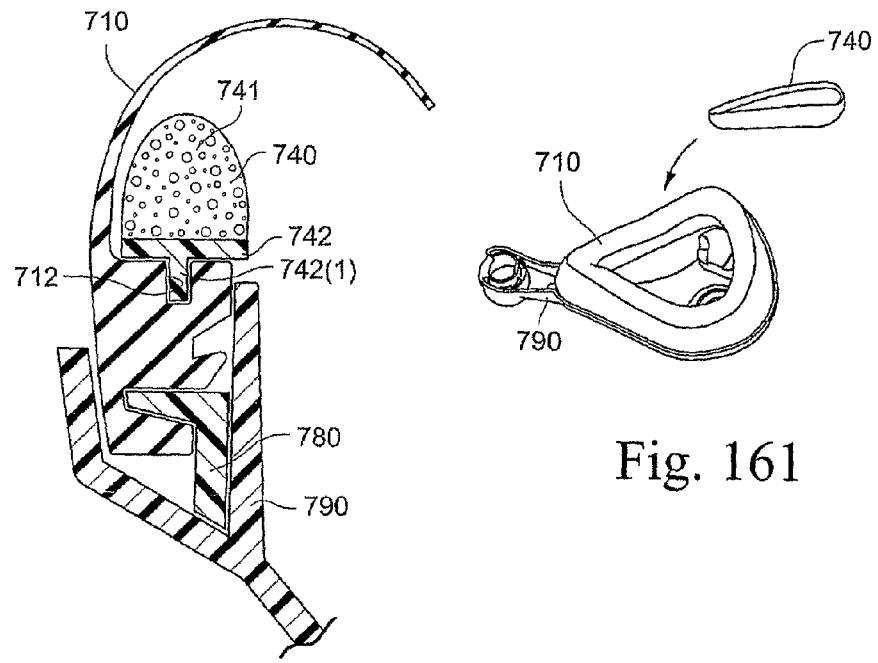
Fig. 160
Fig. 161
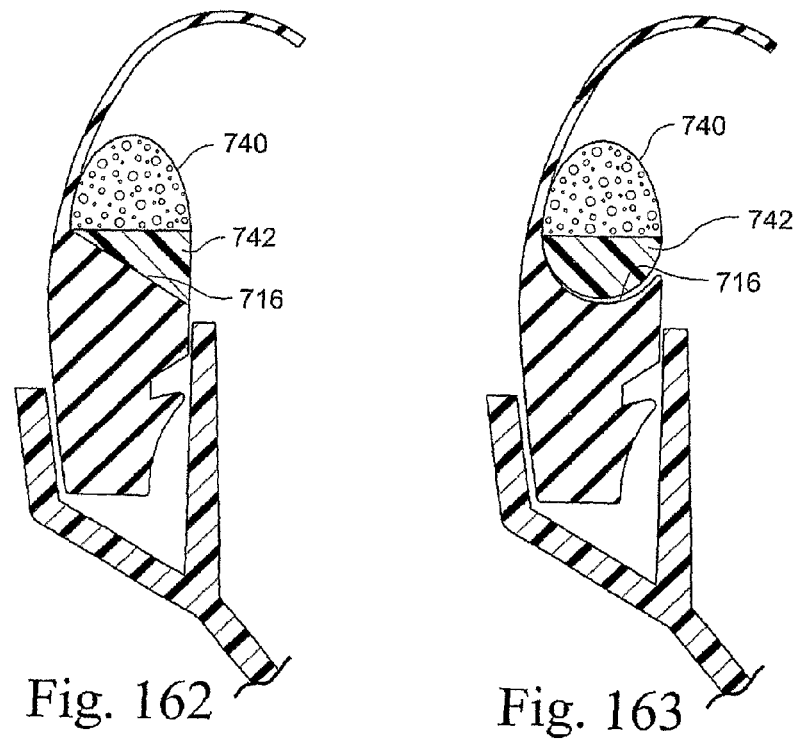
Fig. 162
Fig. 163

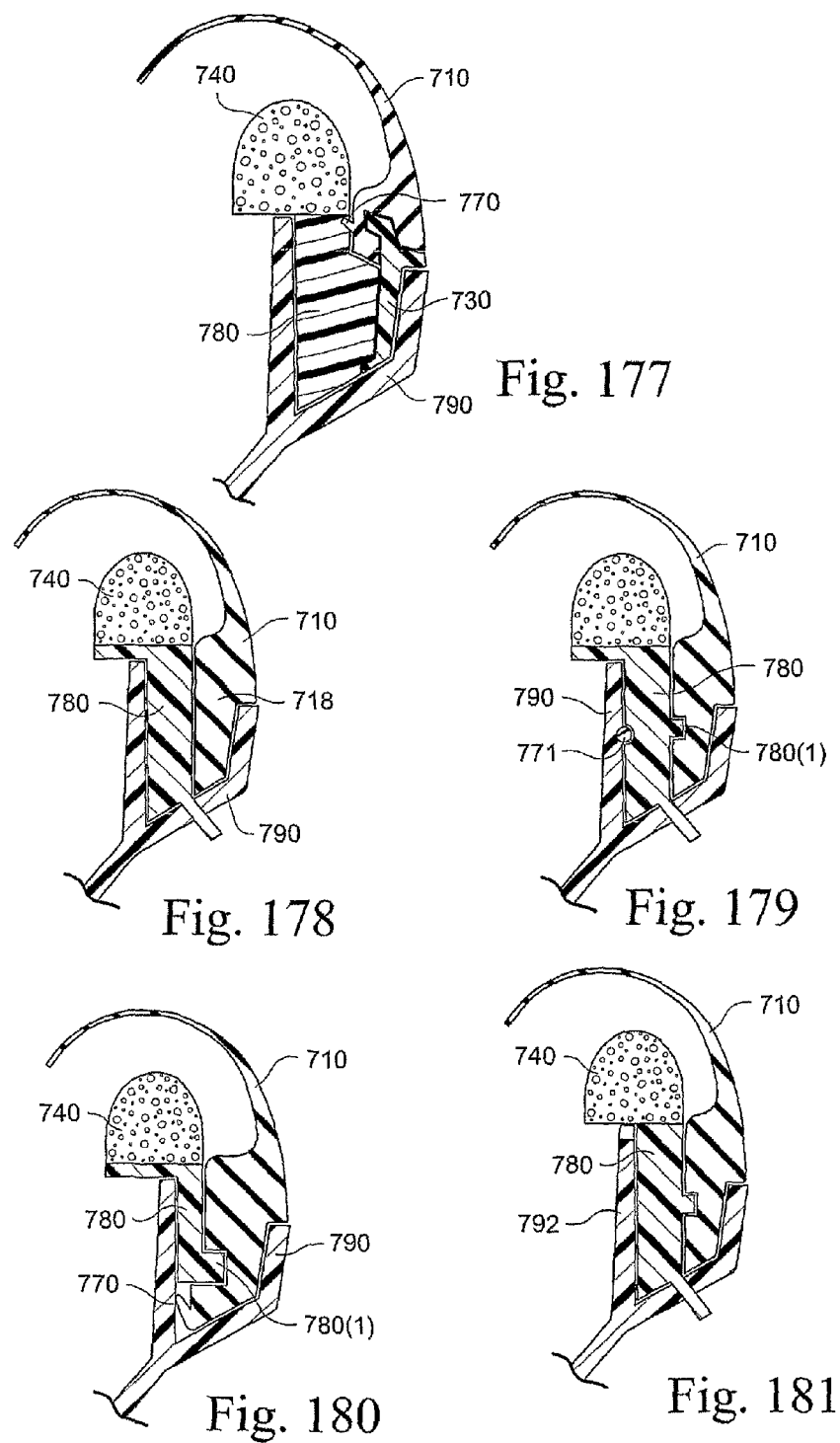

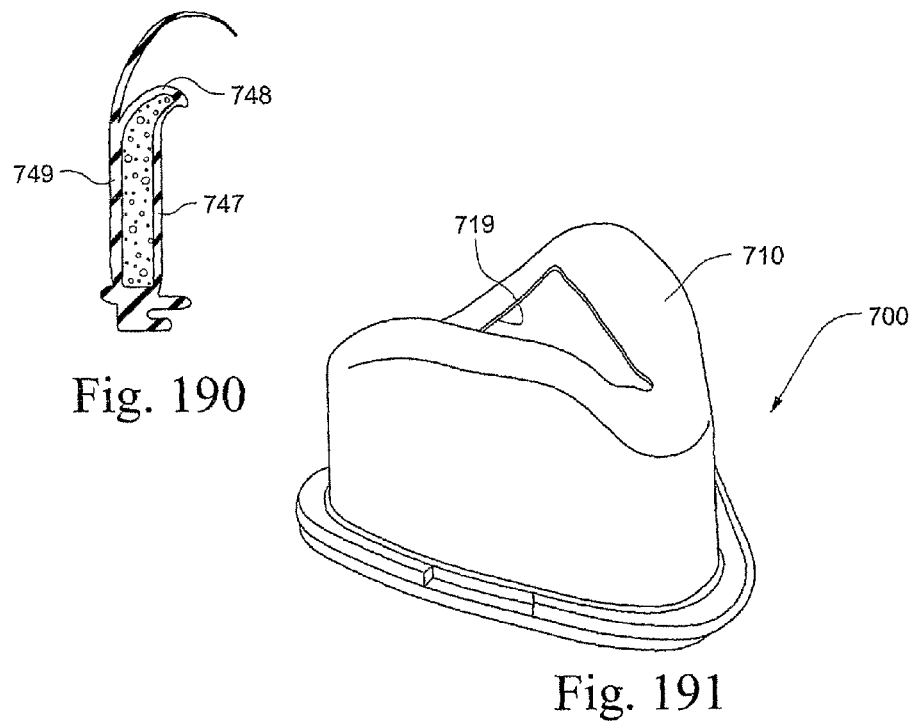
Fig. 190
Fig. 191
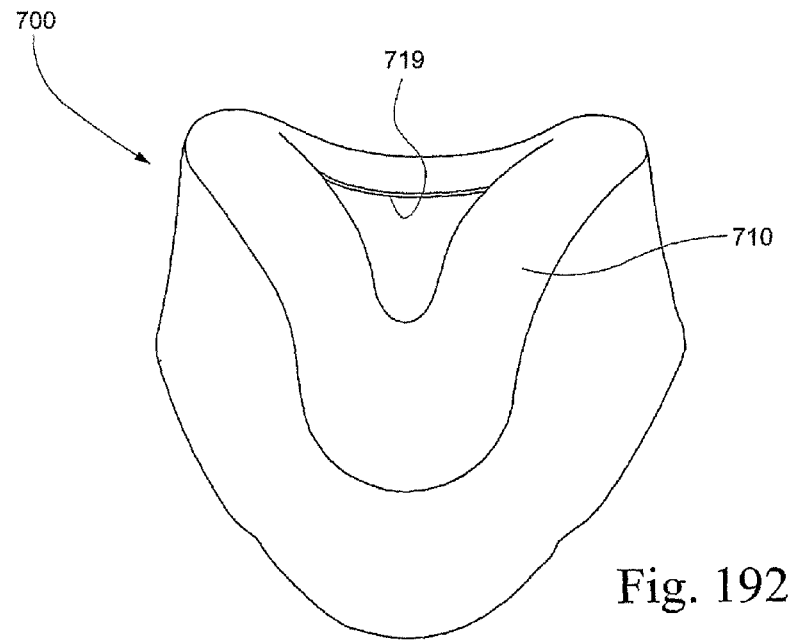
Fig. 192

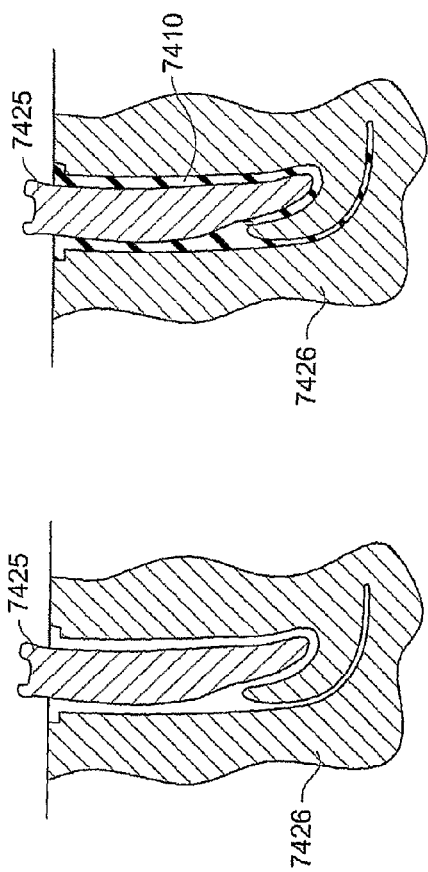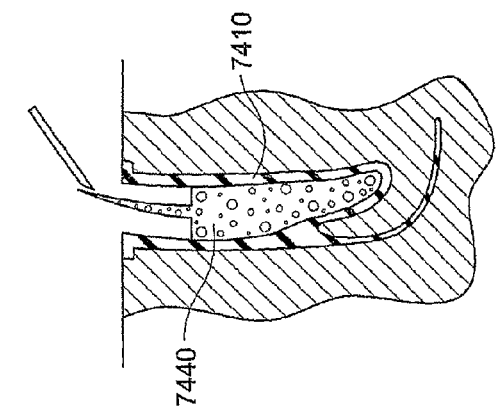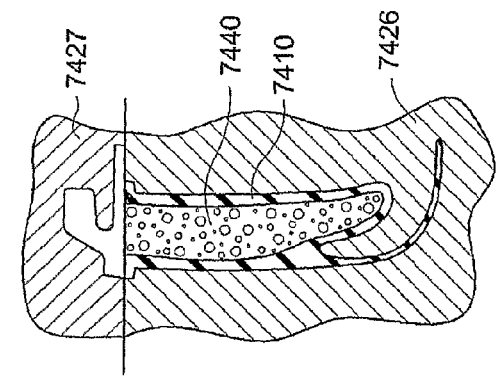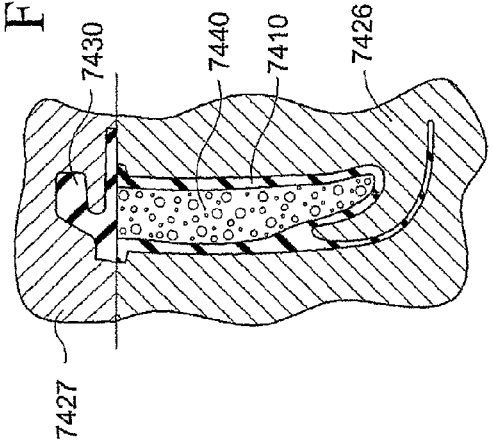
Fig. 209-1
Fig. 209-2
Fig. 209-3
Fig. 209-4
Fig. 209-5

CUSHIONING STRUCTURE

CROSS-REFERENCE TO APPLICATION

This application is the U.S. national phase of International Application No. PCT/AU2008/001711, filed Nov. 17, 2008, which designated the U.S. and claims the benefit of Australian Provisional Application Nos. AU 2007906253, filed Nov. 15, 2007, AU 2007906271, filed Nov. 16, 2007, AU 2008900072, filed Jan. 4, 2008, AU 2008902720, filed May 29, 2008, AU 2008901271, filed Mar. 14, 2008, and AU 2008903294, filed Jun. 27, 2008, and European Application No. EP 08160921.6, filed Jul. 22, 2008, each of which is incorporated herein by reference in its entirety.

FIELD OF THE INVENTION

The present technology relates to cushioning structure between a person and some form of apparatus. For example, the present invention may relate to the cushioning structure of respiratory equipment.

BACKGROUND OF THE INVENTION

The use of Nasal Continuous Positive Airway Pressure (nasal CPAP) to treat Sleep Disordered Breathing (SDB) was pioneered by Sullivan, e.g., see U.S. Pat. No. 4,944,310. Apparatus for providing nasal CPAP typically comprises a source of air at positive pressure (for example provided by a blower or flow generator), some form of patient interface or respiratory mask system (for example a nasal or full-face mask system), and an air delivery tube.

Respiratory mask systems typically include some form of cushioning element (a "cushion"), a sealing element and some form of stabilizing element (for example, a frame and headgear). The cushioning and sealing elements may be formed in one piece, or more than one piece, or may be separate structures. Cushioning and sealing elements may be formed from different portions of a single structure. Headgear may consist of an assembly of soft, flexible, elastic straps. They may be constructed from a composite material such as foam and fabric.

The frame may be a rigid or semi-rigid structure that allows for the connection of the undercushion, headgear and air delivery tube. The frame can be made of polycarbonate, silicone or various other materials.

Much mask design effort is directed towards improving the comfort of masks. A range of commercial mask systems are known including the MIRAGE mask, manufactured by ResMed Limited.

SUMMARY OF THE INVENTION

A first aspect of the present technology is to provide a comfortable cushioning structure for use with a patient interface for respiratory equipment, and method of manufacturing the cushioning structure.

Another aspect of the present technology is to provide a respiratory mask comprising a comfortable cushioning structure and a seal forming structure, methods for manufacturing the cushioning structure, and methods for manufacturing the seal forming structure, and methods for manufacturing a combined seal and cushioning structure.

Another aspect is to provide a cushioning structure that includes one or more chambers adapted for filling with soft, and/or conformable materials. The filling materials may have the same, graded or different properties. The filling materials may have the same or different storage modulus, loss modulus, stiffness, hardness, softness, elasticity, thicknesses, resiliency, recoil-characteristics and/or visco-elastic properties. One or more filling materials may be located in the same chamber, or in different chambers. In one form the filling materials may be gel materials, or gel-like materials. The filling materials may be foam. In addition, the cushioning structure may include one or more portions of a rubber material such as silicone, or a thermoplastic elastomer. The cushioning structure may have different properties in different regions, for example, for contact with different regions of the face such as the nose, cheek or top lip.

Another aspect of the present technology is methods of manufacturing a cushioning structure, including one or more of methods of forming, filling, or sealing a cushioning structure. Methods in accordance with the present technology include vacuum forming and molding.

Another aspect of the present technology relates to different softnesses of materials by varying the thickness of materials.

One aspect of the invention relates to a patient interface including a cushioning structure including at least one hollow chamber filled with first and second discrete and/or layered filling materials and a seal forming structure formed in one piece with the cushioning structure. The seal forming structure including a thin membrane flap that is structured to provide a seal to the patient's face. The thin membrane flap includes a free end that is spaced from the cushioning structure in its substantially relaxed, unstressed state and is responsive to a pressure difference between the interior and exterior of the mask chamber to bring at least a portion of the membrane flap into sealing engagement with the patient's face.

Another aspect of the invention relates to a method for manufacturing a patient interface including molding a cushioning structure including at least one chamber adapted to be filled with at least one filling material and a seal forming structure including a thin membrane flap in one piece with the cushioning structure with LSR, filling the at least one chamber with at least one filling material, and molding a cap and attaching the cap to the cushioning structure to enclose the at least one chamber. Another aspect relates to a method of adjusting the cushioning effect of a mask structure by varying the relative volume, or location of at least two filling materials, wherein the two filling materials have different mechanical properties. For example, a first filling material is softer than a second filling material.

Another aspect of the invention relates to a patient interface including a polyurethane skin including at least one chamber filled with gel, wherein the polyurethane skin includes an end portion that is oriented or curved inwardly to promote bending or rolling inwards towards the breathing cavity when force is applied thereto in use.

Another aspect of the invention relates to a method for manufacturing a patient interface including vacuum forming a polyurethane skin including at least one chamber adapted to be filled with gel and an end portion that is oriented or curved inwardly to promote bending or rolling inwards towards the breathing cavity when force is applied thereto in use, filling the at least one chamber with gel, and attaching a backing to the polyurethane skin to enclose the at least one chamber.

Another aspect of the invention relates to a cushion assembly for use with a respiratory mask including a bladder filled with a combination of a gel having a first indentation hardness and a gel having a second indentation hardness.

Another aspect of the invention relates to a respiratory mask system including a cushioning element having Shore 000 hardness in the range of about 10 to about 20.

Another aspect of the invention relates to a respiratory mask system including a cushioning element having Shore 000 hardness in the range of about 45 to about 90.

Another aspect of the invention relates to a respiratory mask system including a cushioning element having Shore 00 hardness equal to or greater than about 20, e.g., about 20 to about 30 or any value inbetween, i.e., 21, 22, 23, 24, 25, 26, 27, 28, 29.

Another aspect of the invention relates to a respiratory mask system including a cushioning element having Shore 00 hardness less than or equal to about 5, e.g., 5, 4, 3, 2, 1.

Another aspect of the invention relates to a respiratory mask system including a cushioning element having cone penetration hardness less than about 5 cone penetrations.

Another aspect of the invention relates to a respiratory mask system including a cushioning element having cone penetration greater than about 200 cone penetrations, e.g., about 200 to about 400, about 200 to about 250.

Another aspect of the invention relates to a respiratory mask system including a cushioning element having cone penetration between about 5 and about 250 cone penetrations, or e.g., about 150 to about 200, about 160 to about 180, about 200 to about 400, about 200 to about 250.

Another aspect of the invention relates to a respiratory mask system including a cushioning element having an encased gel and a silicone membrane spaced from the encased gel.

Another aspect of the invention relates to a cushioning element for a respiratory mask system including a bladder filled with a first gel and a second gel that is relatively harder than the first gel. The first gel has a Shore 000 hardness in the range of about 10 to about 20 and/or the second gel has a Shore 000 hardness greater than about 45.

Another aspect of the invention relates to a cushioning element for a respiratory mask system including a bladder filled with a first gel and a second gel that is relatively harder than the first gel, and a sealing membrane formed in one piece with the bladder. The sealing membrane is constructed from a thin membrane flap that is structured to substantially cover at least a portion of the bladder.

Another aspect of the invention relates to a respiratory mask system including a cushioning element including an undercushion constructed from a bladder filled with a gel having a Shore 000 hardness in the range of about 10 to about 20 and an over-cushion or sealing membrane constructed from a thin membrane flap having a Shore A hardness in the range of about 20 to about 60.

Another aspect of the invention relates to a method of manufacturing a cushion for a respiratory mask comprising the steps of providing a mold comprising at least two mold halves and at least one core therein, closing the mold, injecting a first material into the mold to form the cushion, wherein the core is enclosed by the cushion thereby forming at least one cavity, opening the mold, removing the core from the cushion to provide the at least one cavity within the cushion, and sealing the cavity.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of the invention. In such drawings:

FIGS. 8a to 8e shows a process for filling a chamber with two gels according to an embodiment of the present invention;

FIGS. 10a and 10b show cross sections of alternative cushion configurations with different material portions according to an embodiment of the present invention;

FIGS. 11a and 11b show side views of alternative cushion configurations with different material portions according to an embodiment of the present invention;

FIGS. 12a and 12b show cross sections of alternative cushion and internal support configurations according to an embodiment of the present invention;

FIGS. 13a and 13b show cross sections of alternative cushion and internal support configurations according to an embodiment of the present invention;

FIG. 14 shows a cross section of a cushion with an internal support, frame interface and sealing membrane according to an embodiment of the present invention;

FIG. 20 shows a cross section of a cushion according to another embodiment of the present invention;

FIG. 21 shows a cross section of an internal support structure according to another embodiment of the present invention;

FIG. 22 shows an isometric view of a cushion according to another embodiment of the present invention;

FIG. 44 is a cross-section of a gel cushion according to another embodiment of the present invention;

FIG. 45 is a cross-section of a gel cushion according to another embodiment of the present invention;

FIG. 46 shows male vacuum forming according to an embodiment of the present invention;

FIG. 47 shows female vacuum forming according to an embodiment of the present invention;

FIG. 52 illustrates cushion, clip, and frame according to an embodiment of the present invention;

FIG. 53 illustrates a cushion with first and second sections according to an embodiment of the present invention;

FIGS. 54 and 55 illustrate a cushion with multiple adjacent ribs according to an embodiment of the present invention;

FIG. 60 illustrates a cushion according to another embodiment of the present invention;

FIG. 61 illustrates a cushion with three layers of gel according to an embodiment of the present invention;

FIG. 62 illustrates a cushion with a branched medium/high durometer insert according to an embodiment of the present invention;

FIG. 63a illustrates a cushion with insertable or co-molded zones according to an embodiment of the present invention;

FIG. 63b illustrates a cushion with selectively interchangeable zones according to an embodiment of the present invention;

FIG. 64 illustrates a cushion cured and uncured silicone according to an embodiment of the present invention;

FIGS. 65 and 66 illustrate a cushion with a gel first portion and a silicone second portion according to an embodiment of the present invention;

FIGS. 67, 68, and 69 illustrate a cushion adapted to cover nose and mouth contacting portions as well as forehead pad according to an embodiment of the present invention;

FIG. 70 illustrates a cushion having a three piece polyurethane membrane and a gel filling according to an embodiment of the present invention;

FIGS. 71 and 72 illustrate a spring mechanism attached to a gel cushion according to an embodiment of the present invention;

FIG. 73 illustrates a gel cushion with an insertable spring mechanism according to an embodiment of the present invention;

FIG. 86 illustrates a cushion with a gel on either side of the sealing membrane according to an embodiment of the present invention;

FIG. 87 illustrates a clip mechanism provided to the gel of FIG. 86;

FIGS. 88 and 89 illustrate a gel provided to the outside of a cushion membrane according to an embodiment of the present invention;

FIGS. 99 and 100 illustrate cushions with harder components co-molded on a side or under the gel cushion according to an embodiment of the present invention;

FIG. 101 illustrates a ring-like frame with a clamp arrangement for clamping a cushion according to an embodiment of the present invention;

FIG. 117 illustrates a cushion with a textured surface according to an embodiment of the present invention;

FIG. 118 illustrates a lattice-like structure for the cushion of FIG. 117;

FIG. 119 illustrates a small bump structure for the cushion of FIG. 117;

FIGS. 120 and 121 illustrate a harder outer skin pressed over a soft, low durometer gel mass according to an embodiment of the present invention;

FIG. 122 illustrates a cushion wherein the inner wall of the skin is pre-stressed or shortened according to an embodiment of the present invention;

FIG. 123 illustrates a cushion in which the skin is relatively thick to support the gel according to an embodiment of the present invention;

FIG. 124 illustrates a cushion including a thickened inner wall according to an embodiment of the present invention;

FIG. 131 illustrates a cushion with a skin made from fabric or textile material according to an embodiment of the present invention;

FIG. 132 illustrates a gel cushion with an ice-pack arrangement according to an embodiment of the present invention;

FIGS. 133 and 134 illustrate a cushion with small balls of low durometer gel encased in a polyurethane or silicone cushion pouch according to an embodiment of the present invention;

FIGS. 135 and 136 illustrate a cushion with small gel/foam balls encased in a cushion pouch according to another embodiment of the present invention;

FIG. 137 illustrates a cushion with air bubbles provided within a high durometer gel according to an embodiment of the present invention;

FIG. 138 illustrates a cushion including a high durometer gel foam filled or injected with a low durometer gel according to an embodiment of the present invention;

FIG. 139 illustrates a cushion with glitter according to an embodiment of the present invention;

FIG. 140 illustrates a low durometer gel cushion with a mechanical finger pump according to an embodiment of the present invention;

FIG. 141 illustrates a cushion including a draw string according to an embodiment of the present invention;

FIG. 142 is a cross-sectional view of a cushion including a bladder according to an embodiment of the present invention;

FIG. 143 is a cross-sectional view in perspective of the cushion of FIG. 142;

FIG. 144 is a cross-sectional view showing a thickened portion or bead for the cushion of FIG. 142 according to an embodiment of the present invention;

Figure 5:
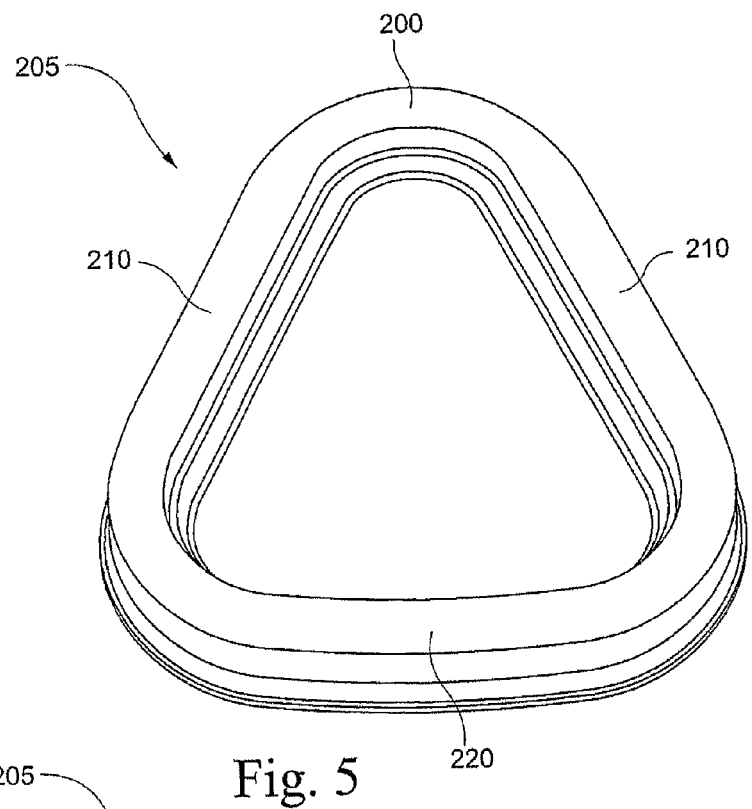
FIG. 5 shows a patient-side view of a cushion incorporating dual durometer gel technology according to an embodiment of the present invention.
Figure 6:
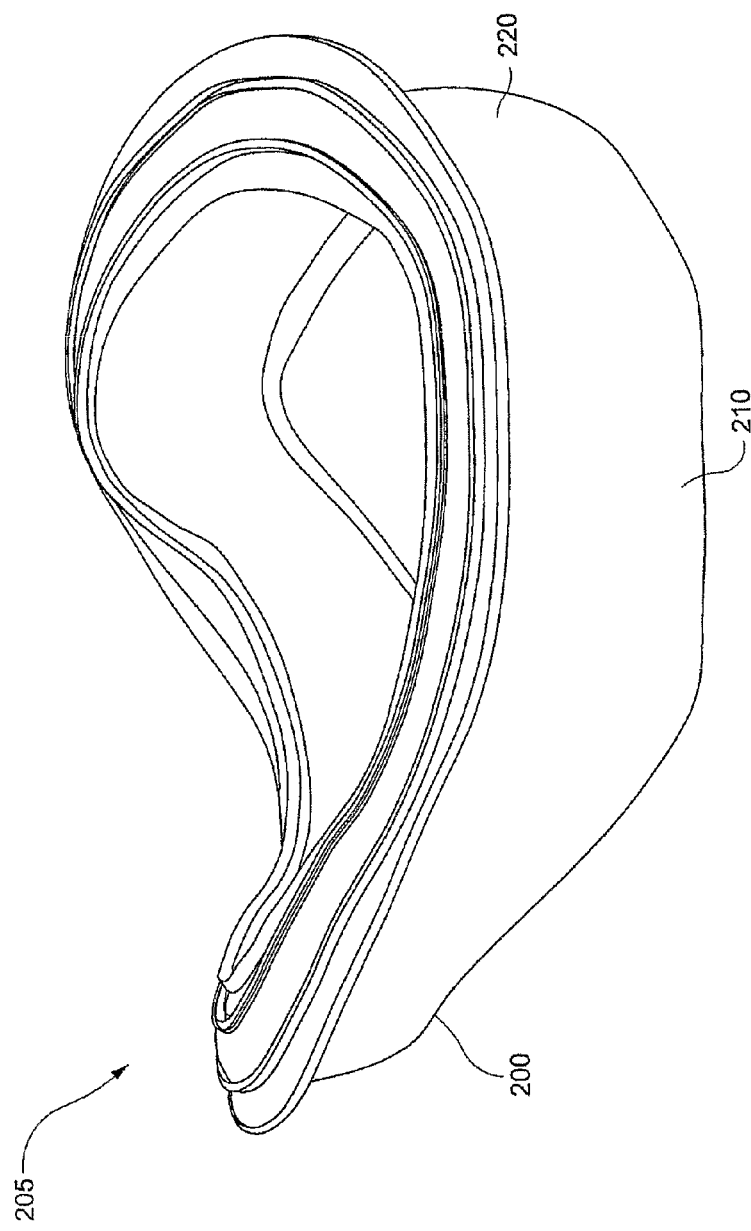
FIG. 6 shows a side view of the cushion of FIG. 5.
Figure 142:
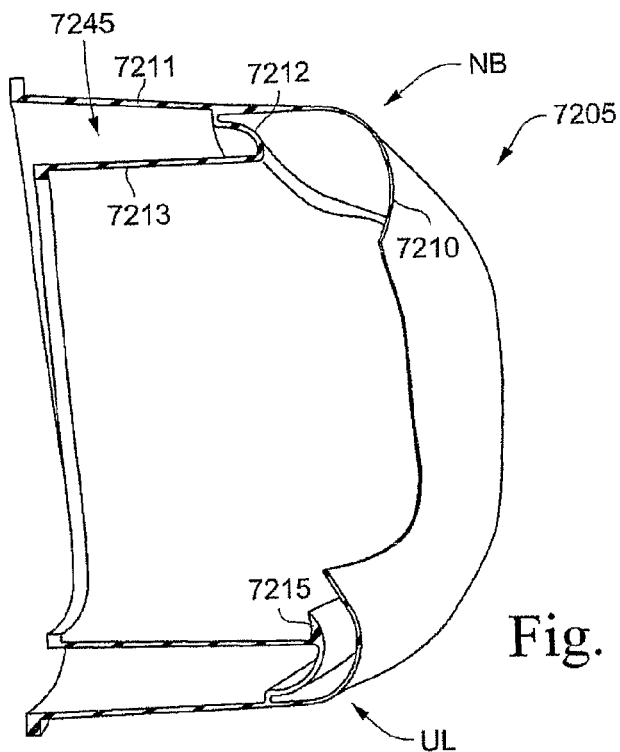
Figure 145:
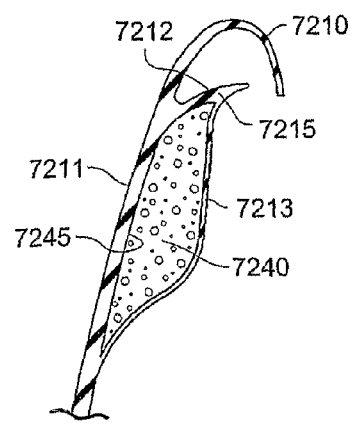
Figure 146:
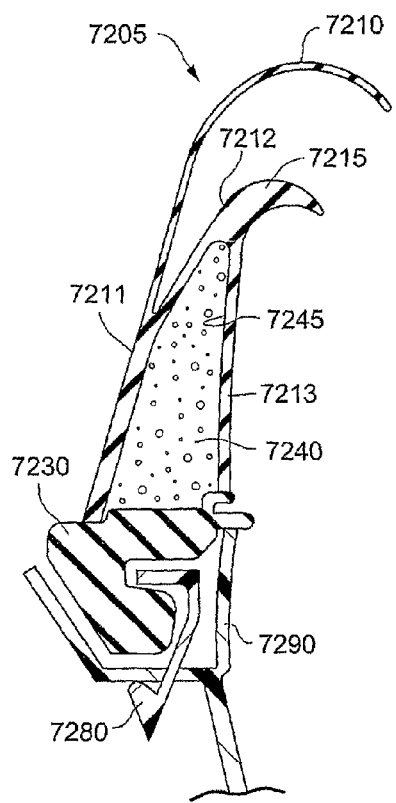
Figure 147:
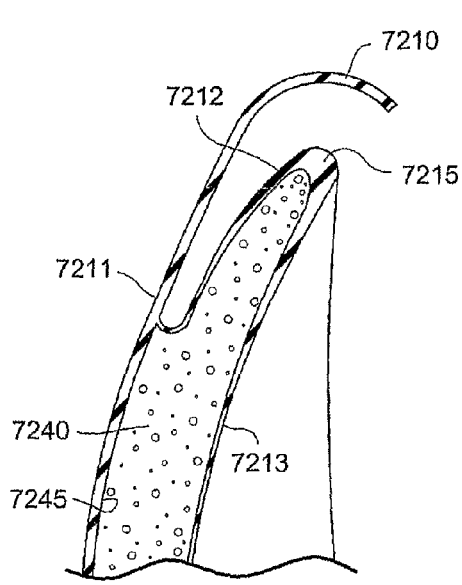
Figure 148:
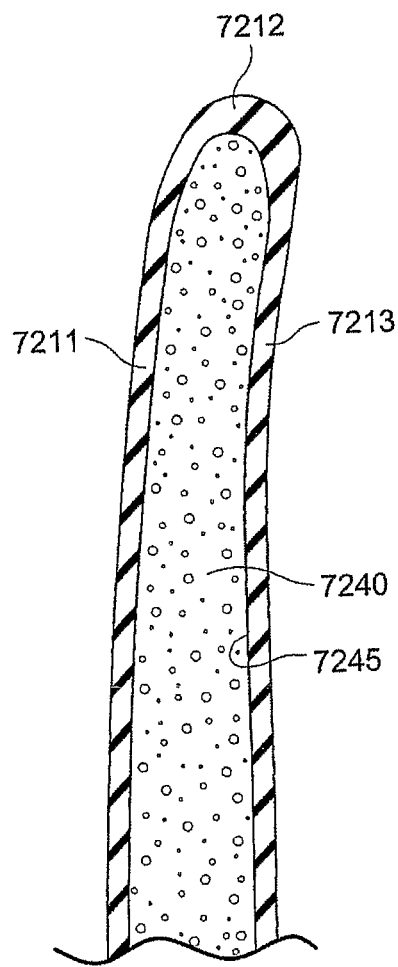
Figure 149:
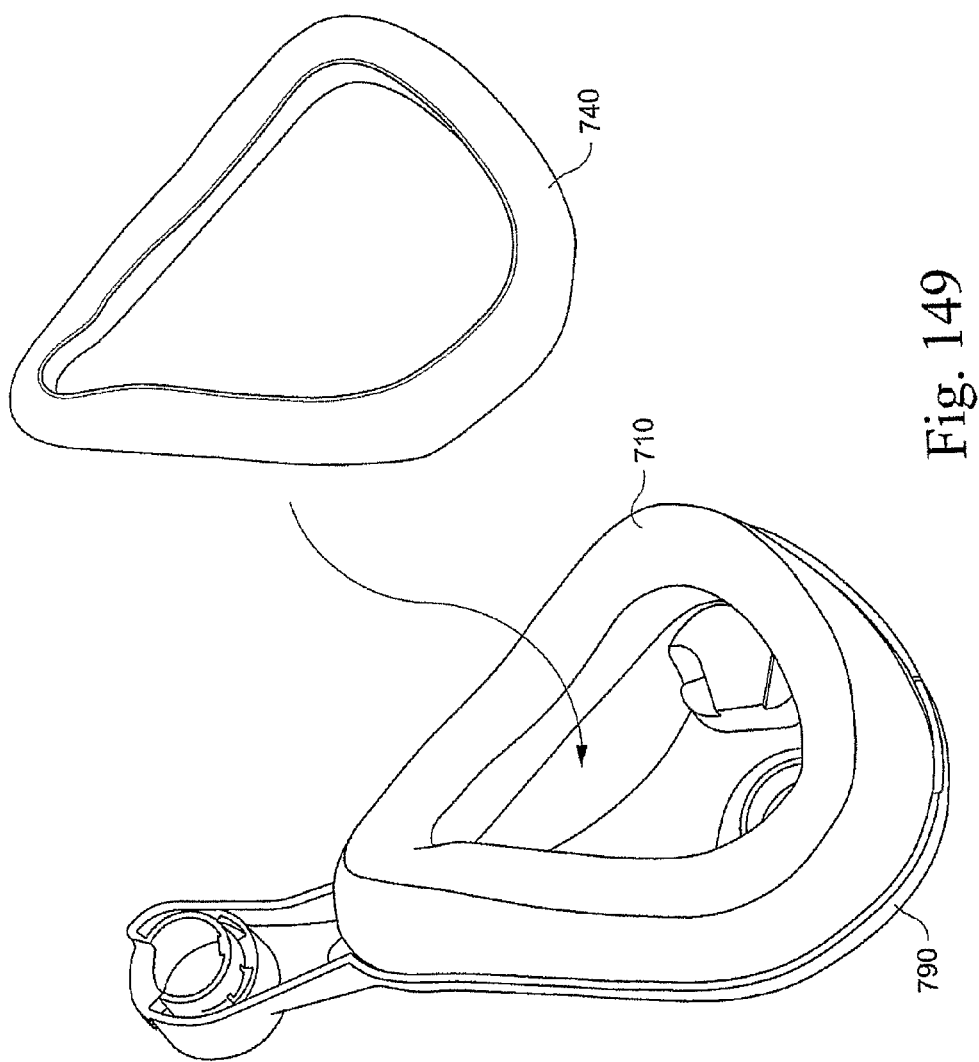
Figure 150:
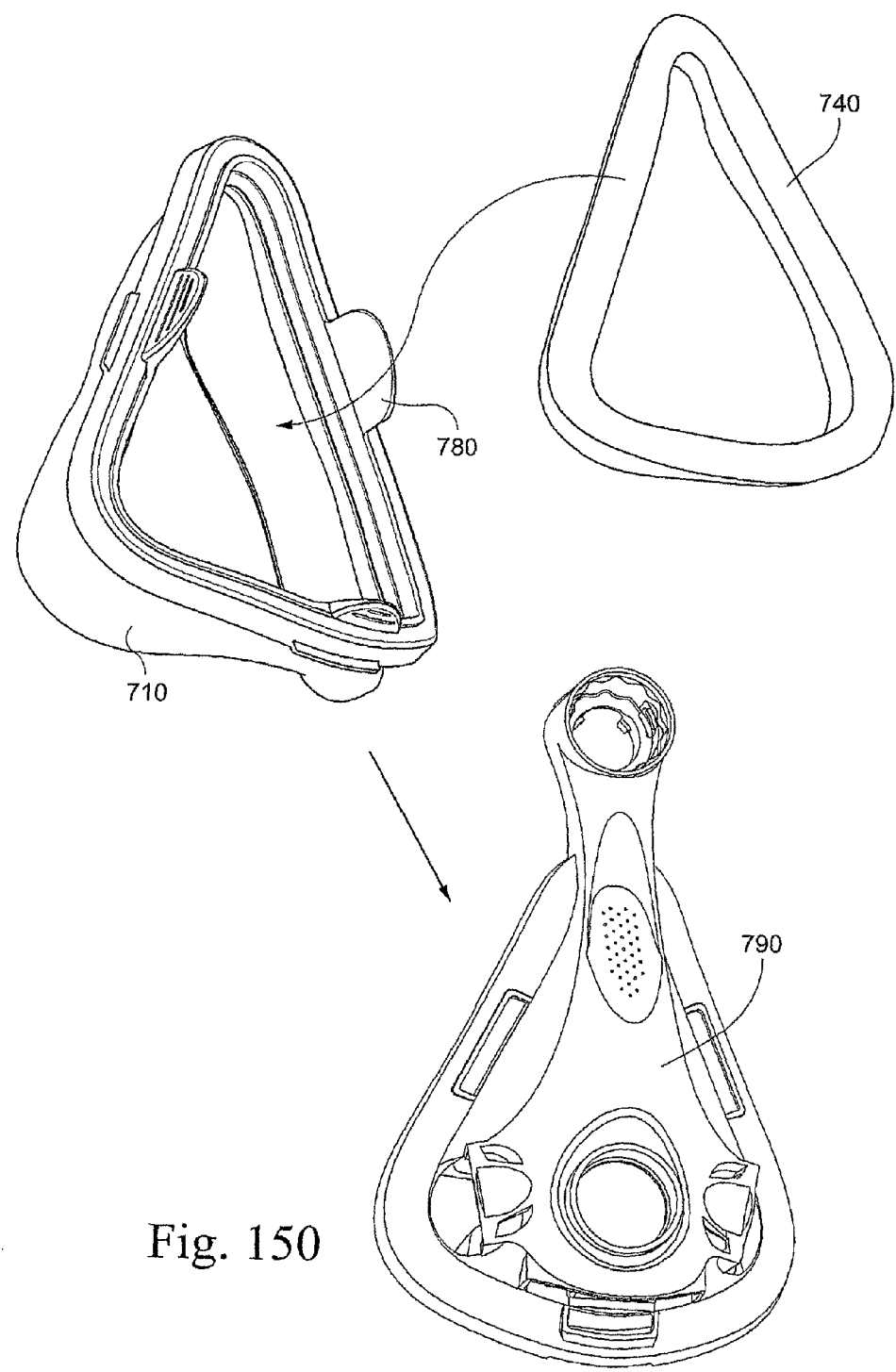
Figure 187:
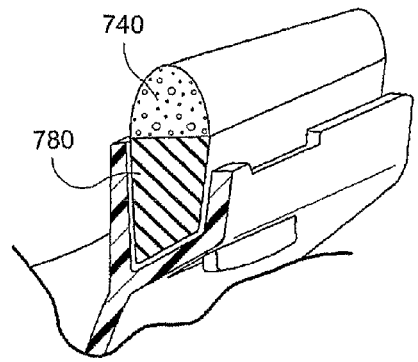
Figure 188:
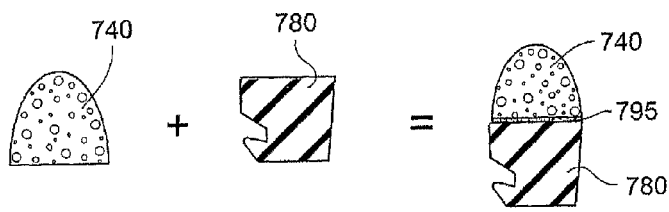
Figure 189:
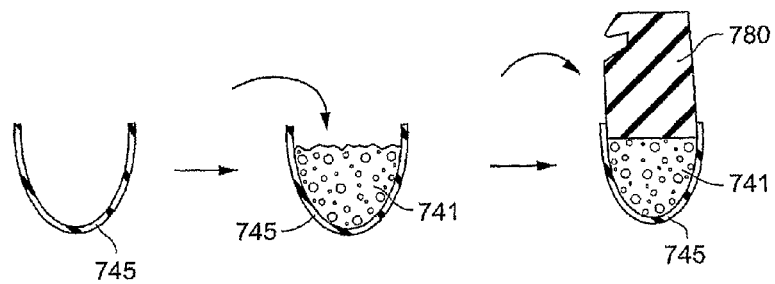
Figure 193:
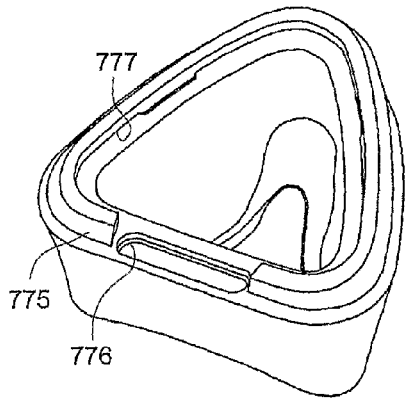
Figure 194:
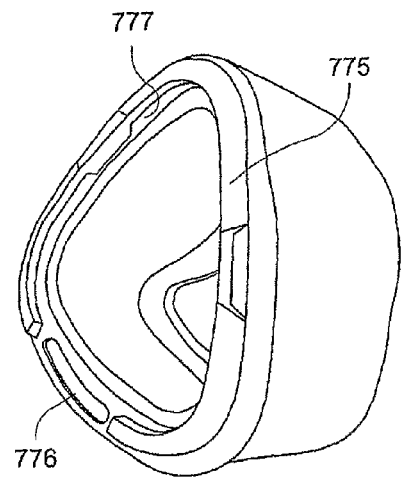
Figure 201:
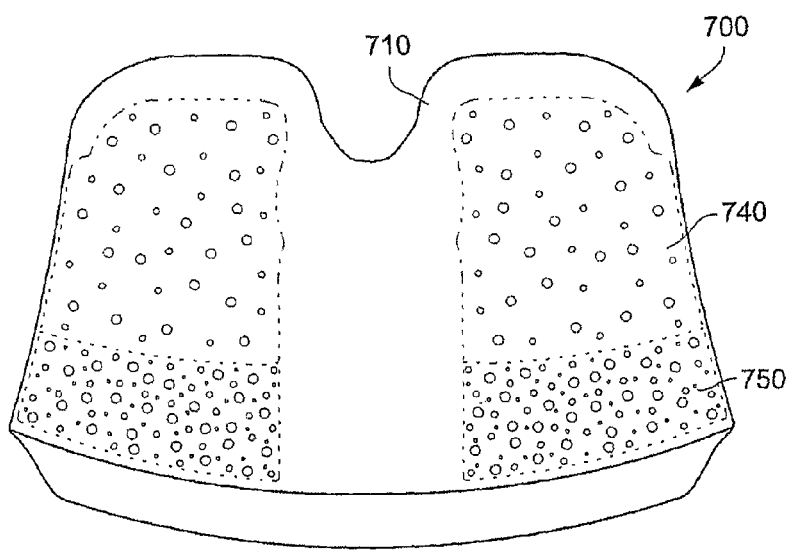
Figure 198:
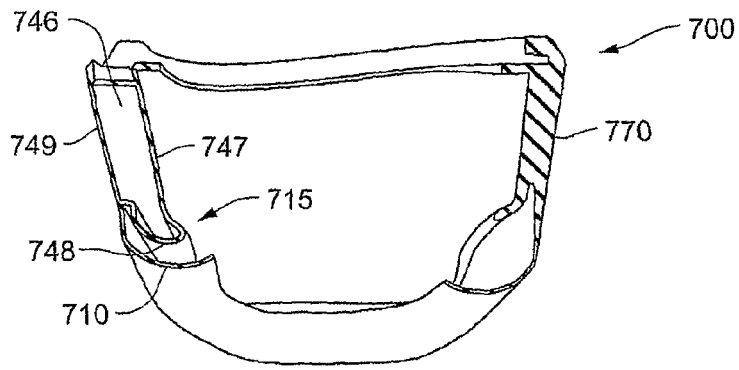
Figure 202:
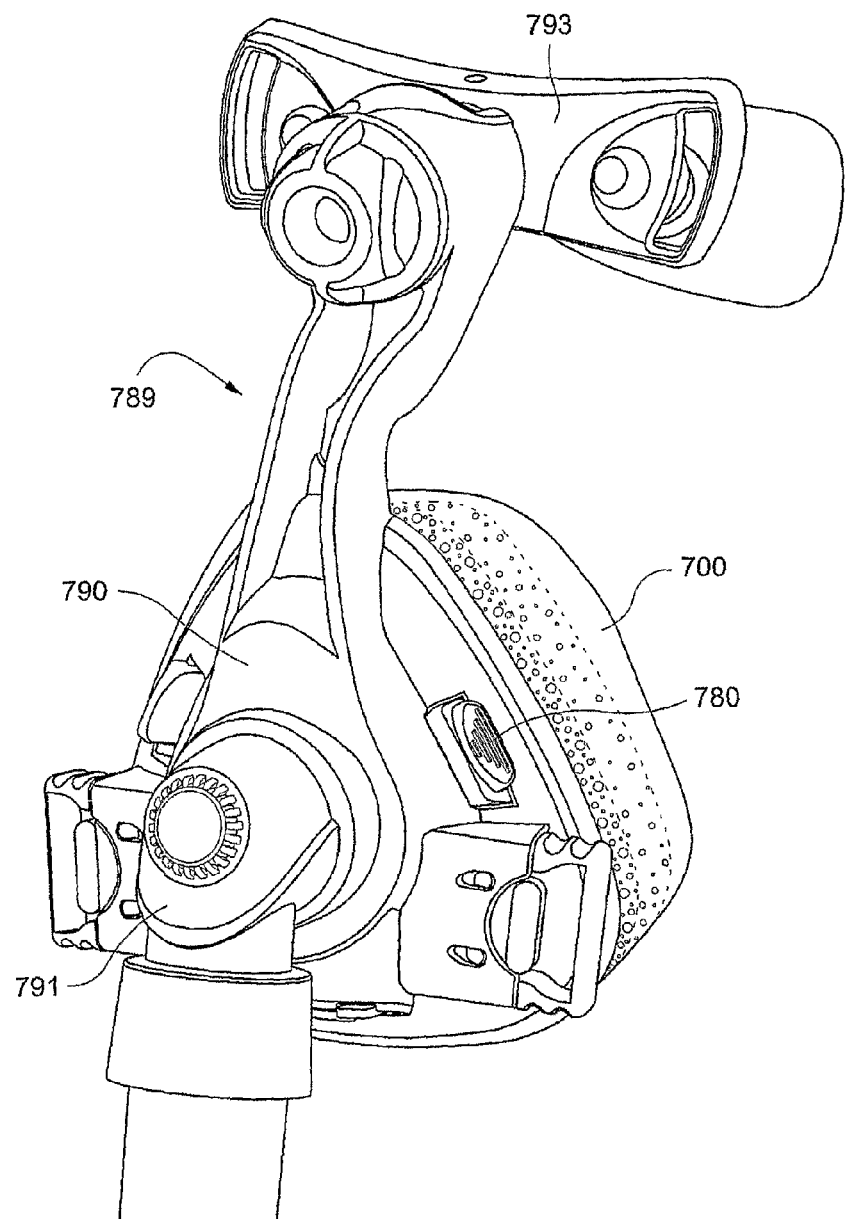
Figure 203:
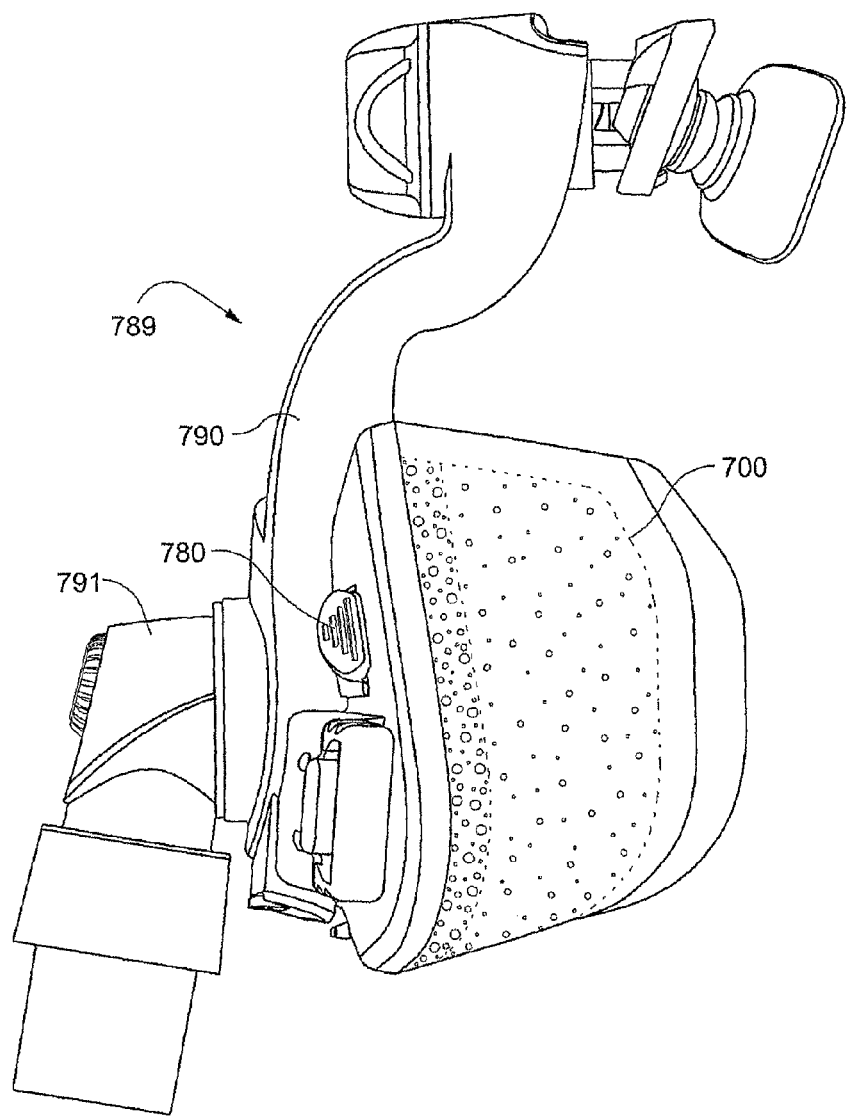
Figure 204:
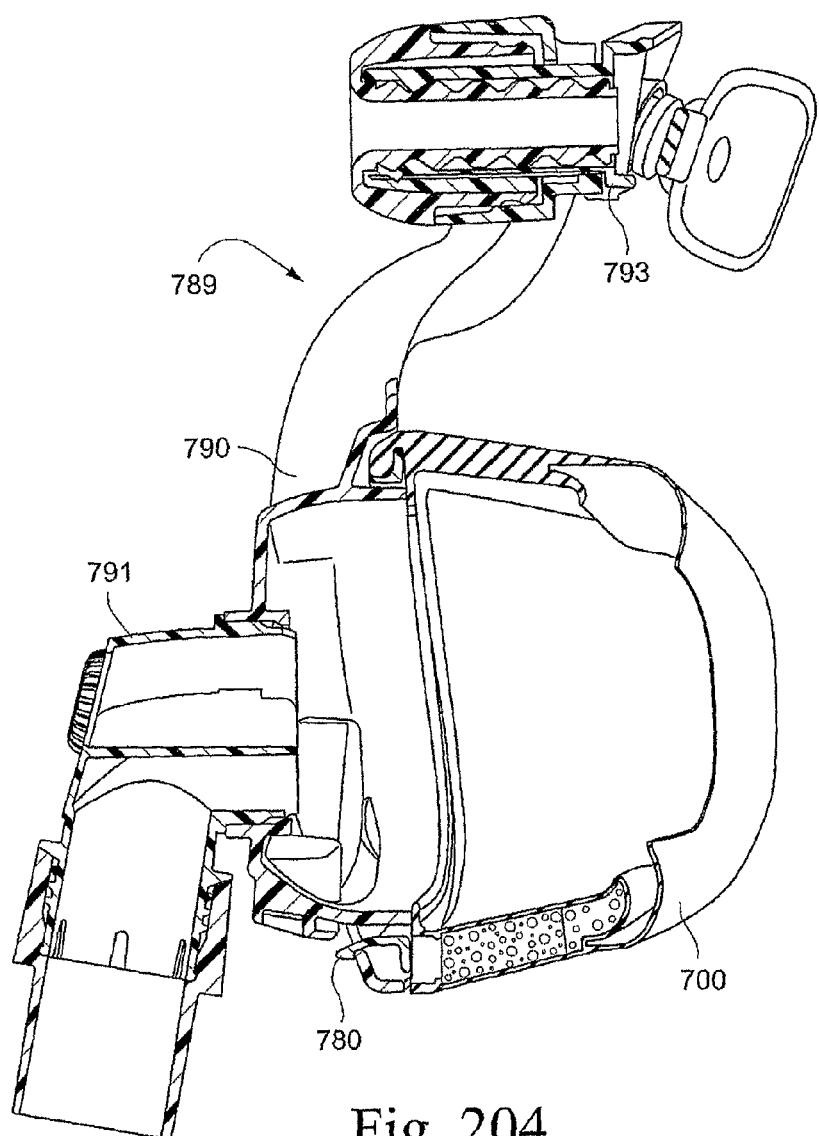
Figure 205:
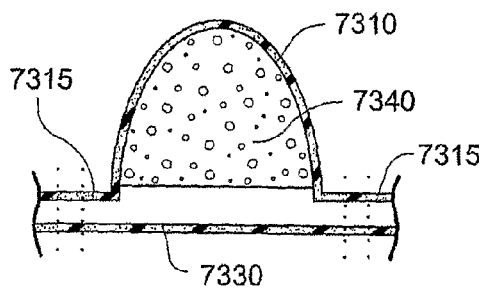
Figure 206:
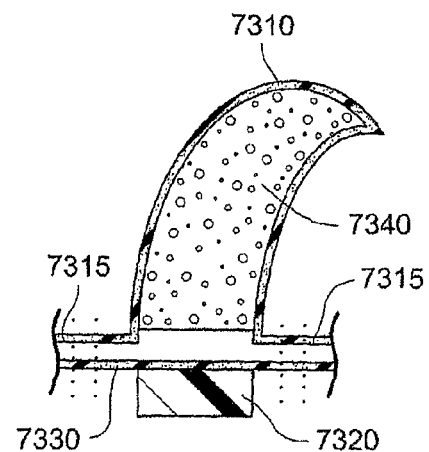
Figure 207:
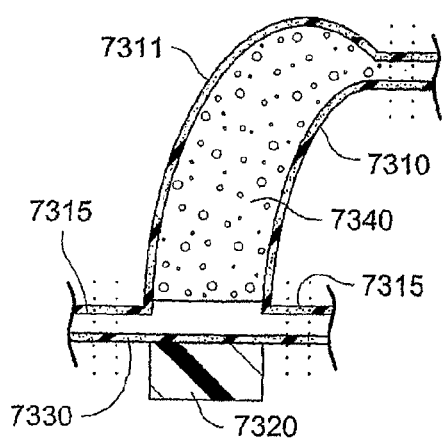
Figure 208:
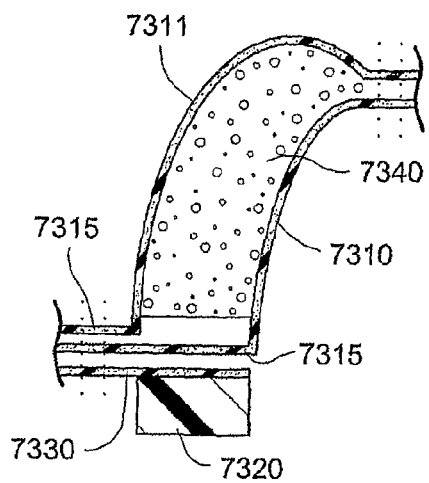
Figures 6, 201:
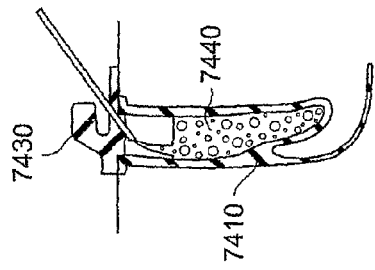
Figures 5, 210:
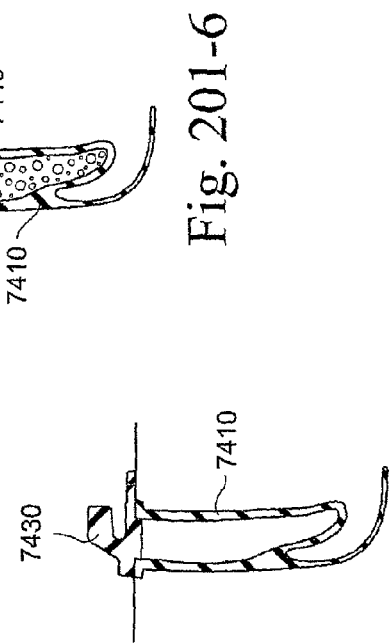
Figures 2, 210:
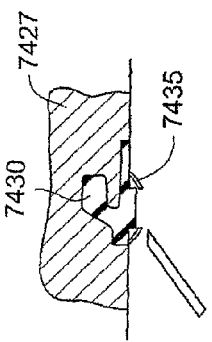
Figures 4, 210:
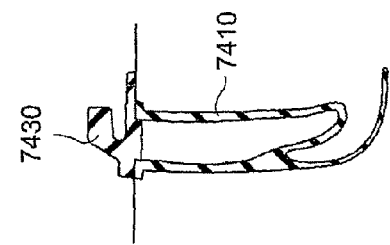
Figures 1, 210:
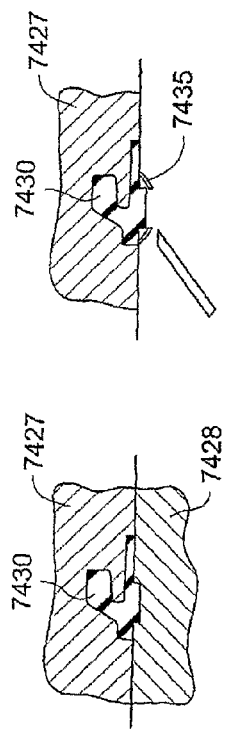
FIG. 1a is an exploded cross-sectional view of a cushioning structure according to an embodiment of the present invention.
FIG. 1b is a cross-sectional view of the cushioning structure of FIG. 1a where the first and second layers are welded together along their edges to define a cavity.
FIG. 1c is a cross-sectional view of the cushioning structure of FIG. 1b where the cavity formed by the layers has been partially filled with a first gel material.
FIG. 1d is a cross-sectional view of the cushioning structure of FIG. 1c where the cavity has been filled with second gel material after having been filled with first gel material.
FIG. 1e shows an alternative arrangement to FIG. 1d, where the cavity is entirely filled with a single gel material.
Figures 3, 210:
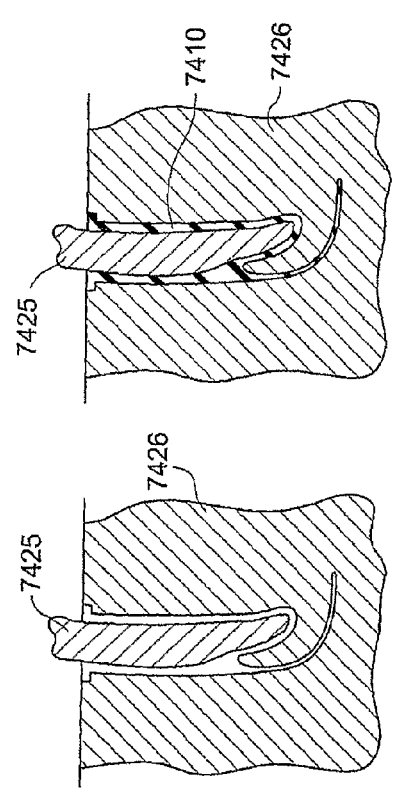
Figure 211:
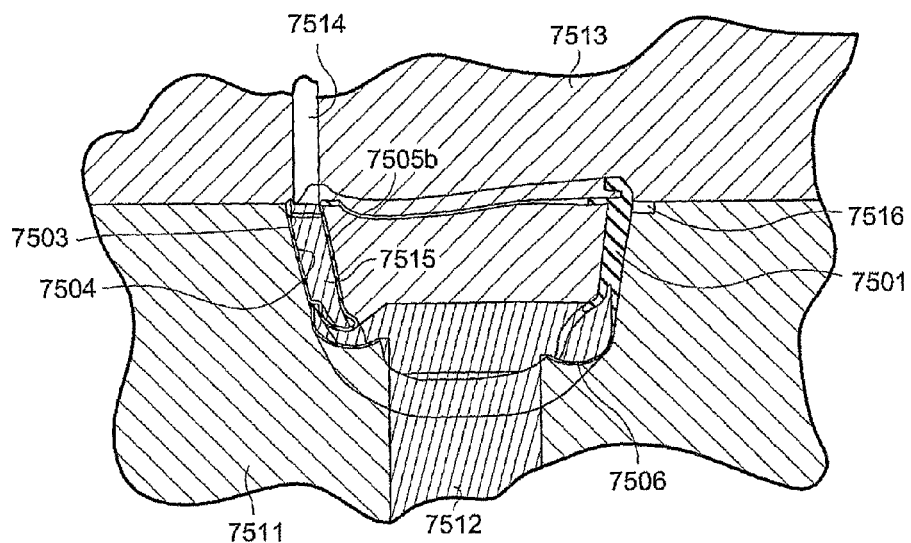
Figure 212:
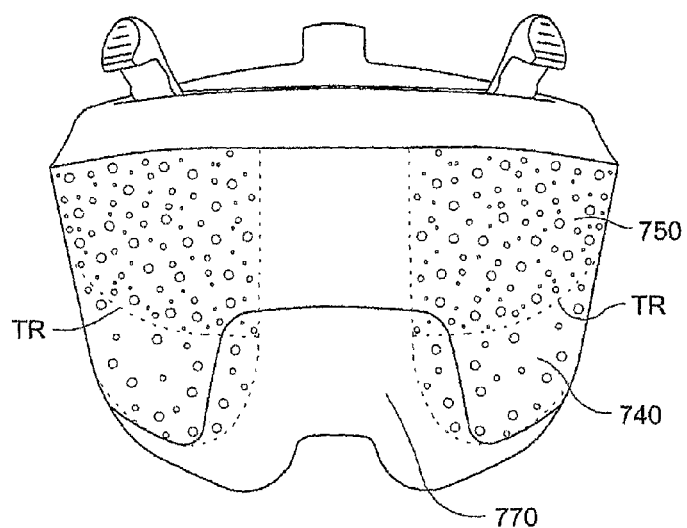
Figure 213:
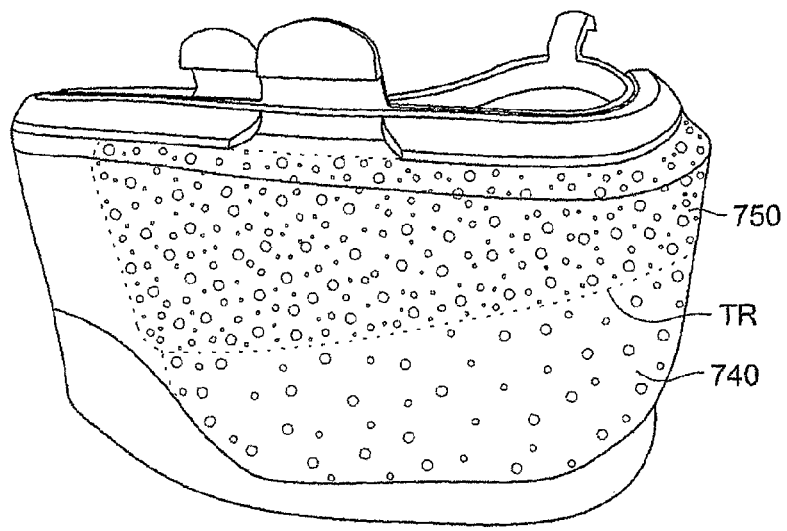
Figure 214:
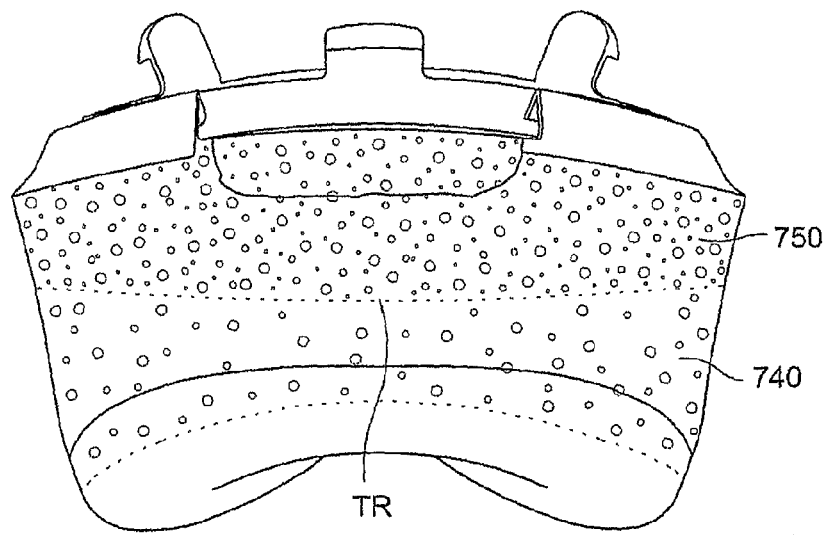

FIG. 145 is a cross-sectional view showing a thickened portion or bead for the cushion of FIG. 142 according to another embodiment of the present invention;

FIG. 146 is a cross-sectional view showing a thickened portion or bead for the cushion of FIG. 142 according to another embodiment of the present invention;

FIG. 147 is a cross-sectional view showing a thickened portion or bead for the cushion of FIG. 142 according to another embodiment of the present invention;

FIG. 148 is a cross-sectional view showing an undercushion and bladder for a cushion with no thickened portion or bead;

FIGS. 149 and 150 illustrate exemplary methods for tucking or inserting a gel bladder into a cushion pocket according to an embodiment of the present invention;

FIGS. 151 to 176 illustrate cushions with tuckable gel bladders according to alternative embodiments of the present invention;

FIGS. 177 to 187 illustrate cushions with stackable gel bladders according to alternative embodiments of the present invention;

FIGS. 188 and 189 illustrate alternative embodiments for manufacturing the stackable gel bladder of FIG. 187;

FIG. 190 illustrates a gel-filled LSR cushion according to an embodiment of the present invention;

FIGS. 191 to 201 are various views of a gel-filled LSR cushion according to an embodiment of the present invention;

FIGS. 202 to 204 illustrate the cushion of FIGS. 191 to 201 provided to a mask according to an embodiment of the present invention;

FIGS. 205 and 206 are schematic views of a gel bladder having a top layer with one skin according to an embodiment of the invention;

FIGS. 207 and 208 are schematic views of a gel bladder having a top layer with two skins according to an embodiment of the invention;

FIGS. 209-1 to 209-5 illustrate an over-molding process for manufacturing a gel-filled LSR cushion according to an embodiment of the present invention;

FIGS. 210-1 to 210-6 illustrate a co-molding process for manufacturing a gel-filled LSR cushion according to an embodiment of the present invention;

FIG. 211 is schematically illustrates a method of manufacturing according to an embodiment of the present invention;

FIG. 212 is a top view of a gel-filled LSR cushion according to an embodiment of the present invention;

FIG. 213 is a side view of a gel-filled LSR cushion according to an embodiment of the present invention; and FIG. 214 is a bottom view of a gel-filled LSR cushion according to an embodiment of the present invention.

DETAILED DESCRIPTION OF ILLUSTRATED EMBODIMENTS

The following description is provided in relation to several embodiments which may share common characteristics and features. It is to be understood that one or more features of any one embodiment may be combinable with one or more features of the other embodiments. In addition, any single feature or combination of features in any of the embodiments may constitute additional embodiments.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The term "air" will be taken to include breathable gases, for example air with supplemental oxygen.

When apparatus such as respiratory equipment are used with people, it is generally desirable to have an interfacing structure positioned either as part of the apparatus, or between the apparatus and the relevant contacting portion of the person to improve the fit and comfort of the apparatus. In the case of respiratory equipment, the interfacing structure may also provide a form of seal against the flow of air.

The interfacing structure may be arranged to form a compression/gasket-type seal, a "flap" type seal, or some combination of these two. A compression-type seal might generally be subjected to compression forces. A flap-type seal might generally be subjected to bending forces. Which forces are involved will depend on the configuration of the interfacing structure, as well as how it is being used. For example, a flap-type seal might be subject to compressive forces in certain configurations and certain uses.

An exemplary mask using a compression-type seal is the SLEEPNET PHANTOM mask, e.g., see U.S. Pat. No. 6,019,101 (Cotner et al.). Another example is the SLEEPNET IQ mask, e.g., see U.S. Pat. No. 6,631,718 (Lovell). Both of these masks include a bladder filled with a soft material.

An exemplary mask using a flap-type seal is the RESPIRONICS CONTOUR mask, e.g., see U.S. Pat. No. 4,907,584 (McGinnis).

The interfacing structure may include components that provide support to a seal portion, but which in of themselves do not form a seal with the face.

Where otherwise not specified, a reference to a Shore 000 hardness is a reference to a Shore 000 hardness measured on a specimen of material in accordance with ASTM D2240-02a, with a specimen thickness of 6 mm, with a 400 g mass for a hand-held durometer, with a rate of descent of the indentor to the specimen of 3.2 mm/s.

1. Gel Materials

The interfacing structure may comprise in part, a component made from a filling material, e.g., such as gel.

A gel may be formed as a colloid that typically contains a high (e.g., greater than 95%) fraction of liquid. The liquid is immobilized by surface tension between it and the macromolecular network built from the small fraction of "gelating" substance present.

In addition to a gel, there may also be materials that have similar material properties to a gel, i.e., gel-like. In this specification, a reference to a gel is to be taken as a reference to either a strict gel, or a material having similar material properties to a strict gel.

A gel material may be tested for indentation hardness, for example as measured on a relevant Shore hardness scale, such as the Shore 000, the Shore 00 or the Shore A hardness scales. It may be appropriate to test a material using a cone penetration test.

Another relevant material property is the tackiness of the gel.

Gels may be formed from a range of different materials, including silicone, polyurethane, and TPE.

Gels may be formed by mixing two or more components that cure to form the final gel. Prior to curing, the mixed components may flow, and may have a viscosity similar to water, or with a higher viscosity.

One example of a suitable gel is WACKER SILICONE gel ELP 26028.

In an embodiment, a gel formed from a low durometer silicone (e.g. less than about 10 on Shore A) may be soft on the patient's skin and so increases comfort (e.g. and therefore patient compliance with respiratory therapy), and decreases pressure points, that might otherwise lead to sores. In an embodiment, the silicone does not include any plasticisers. This avoids the problem of plasticisers leeching out and contacting the patient's skin leaving an unpleasant oily residue as well as weakening and/or warping of the silicone, particularly the membrane. In another embodiment, a thermoplastic elastomer (TPE) that does not include any plasticizers may be used.

2. Functions of Gel Mask Components

Gels will now be described in a form suitable for a respiratory mask, e.g., soft comfortable cushion. It should be appreciated that the gel component may be adapted for use with any suitable mask or cushion, e.g., a full-face mask, nasal mask, nasal pillows or prongs, etc. Additionally, aspects of the invention may be applied to other elements of a mask such as headgear straps and cheek supports.

The gel mask or cushion includes two general components, i.e., a gel and a support structure for retaining or supporting the gel (e.g., bladder (e.g., with optional flap-type membrane), frame, and/or gel to frame interface (e.g., gel to cushion interface and cushion to frame interface)).

Alternatively, the gel may not be completely retained within a structure or may not be retained within a structure at all. The gel may have no covering (skin or bladder) or may be coated with a material that does not provide any structure, e.g., flocking.

It should be appreciated that the gel may contact the patient's face directly, or a cushion membrane may be interposed between the user and the gel.

2.1 Support Structure

2.1.1 Bladder

In use, gels may be encased within a bladder, chamber, or cavity. The bladder may be formed from a range of materials including polyurethane, silicone, TPE, and LSR, or any other suitable material or combination of materials. The bladder can be inelastic (e.g., polyurethane) or elastic (e.g., TPE, LSR). Details on the elastic bladder can be found in U.S. Provisional Patent Application No. 60/907,609, which is incorporated herein by reference in its entirety. The bladder may be constructed by Radio Frequency (RF) welding (also referred to as dielectric welding) together one or more pieces of the relevant material to form one or more chambers. In another form, the gel may be encapsulated in a cavity formed in a molded silicone component (e.g., gel-filled LSR).

The bladder contains and protects the gel, protects the patient from the gel, provides structure/shape of the cushion, provides buckling and compression properties (aspect ratio), provides hardness of the cushion, provides deformation properties, and defines manufacturing capabilities (e.g., male/female mold).

2.1.1.1 Bladder Shapes

FIGS. 1*a*-1*e* and 8*a*-8*e* shows a schematic cross-section of a bladder or chamber 10, 315, formed for example from a layer of polyurethane. In these illustrated embodiments, the chamber has a generally constant cross-section along most of its length. FIGS. 2*a*-2*d*, 10*a*, 10*b*, 13*a*, 13*b*, 18, 20, 43, and 153, for example, also illustrate bladders with a generally similar cross-section.

However, it should be noted that the chamber need not have a constant cross section. The chamber may be any desired shape, for example rectangular or an irregular shape.

The shape of the bladder may be configured to provide the most desirable comfort and stability properties to each region of the face, for example, increase comfort at the nasal bridge and increase stability at the cheeks.

The shape of the undercushion is not limited, i.e., it can be generally triangular, bilobular, circular, square or any other desired shape. The shape of the undercushion may also include a sickle or question mark shape as outlined in International Patent Application No. PCT/AU2006/000032, which is incorporated herein by reference in its entirety.

2.1.1.1.1 Wider Base

Figure 15:
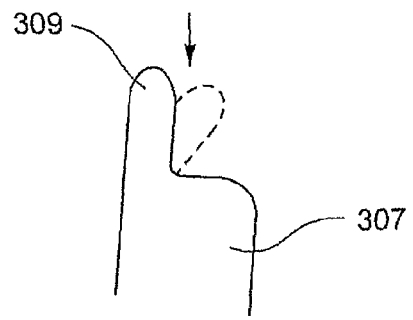
FIG. 15 shows a schematic view of a cushion according to another embodiment of the present invention.

FIGS. 15 and 53 show a cushion with a bladder that is wider on the frame contacting side 307 than the patient contacting side 309. A cushion in such a configuration may be filled the same durometer material in its wider section 307 and with a similar durometer in its thinner patient contacting section 309. The geometry of the sections and the materials contained within these geometries will mean that the wider portion is providing a stabilizing structure to the cushion, while the thinner portion is providing cushioning to the patient in use (e.g., flexibility of patient contacting side 309 shown in dashed lines). In an alternative embodiment, the sections may be made as two separate parts that can be interference fit together. In an embodiment, not all the cushion needs to deform to cover fit range.

Figure 16:
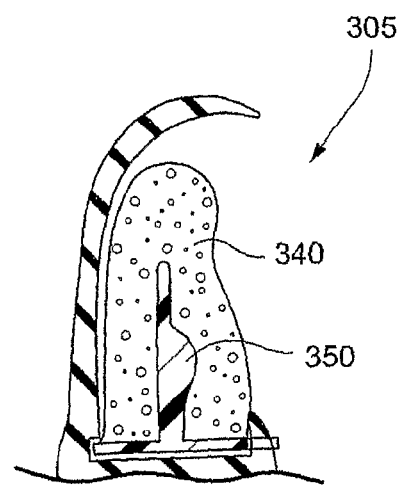
FIG. 16 shows a cross section of a cushion according to another embodiment of the present invention.

FIG. 16 illustrates a cushion 305 wherein the lower part of the bladder closest to the frame contacting portion of the cushion may be made wider to provide greater stability to the cushion and support the gel in an upright position. Alternatively, this configuration could be achieved by replacing the second gel 350 with an insert made from any reasonable material such as polycarbonate or polypropylene.

2.1.1.1.2 Narrower Base

FIGS. 151 and 152 show a bladder wherein the lower part closest to the frame is narrower than its patient contacting side. Such configuration may be provided to facilitate inward flexing of the bladder and membrane.

2.1.1.1.3 Curved

FIG. 12*a* and FIG. 12*b* show cushions with curved structures. In FIG. 12*a*, both an interior structure 350 and the surrounding structure 340 are curved. In FIG. 12*b* interior structure 350 is straight, whereas the exterior structure 340 is curved. Curvature of either or both structures may result in a more comfortable cushion subject to more bending forces, than compression forces in use. Additionally, an inwardly curved cushion may tend to bend inwards, so an effective seal is likely to be achieved, whereas with straight cushions (i.e., normal to the face of the patient) can buckle and bend irregularly (inside or outside) and unpredictably thus making it difficult to ensure a seal.

FIG. 44 shows a cushion 805 with a functional shape, e.g., curved gel 840 and membrane 810, which causes the cushion to tend inwards and therefore may seal better or at least in a different way which may be more comfortable. Also, the functional shape provides a more consistent seal as the cushion will tend inwards, which is unlike prior art where cushion can flex outwards so quality of seal may be more random. This shape may be ideal for gels Shore 000 45-70, i.e., this is to ensure the shape of the cushion is maintained, a softer gel may collapse. This shape may also be reasonable for gels Shore 000 20-45, i.e., there may be some loss of shape but this gel may also be more comfortable.

FIG. 45 shows a cushion 905 with a curvature e.g., different cross sections of gel 940 and membrane 910 throughout the cushion. This embodiment may be made using a vacuum forming process, which can affect the properties of the skin, so that some parts are harder than others and therefore can be less comfortable. FIG. 46 shows male vacuum forming wherein a harder/thicker skin is at the top near the patient contacting surface, and FIG. 47 shows female vacuum forming wherein a softer/thinner skin is at the top.

Figure 82:
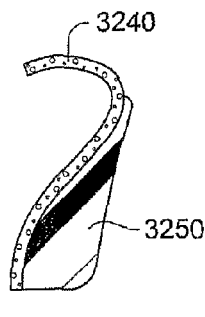
FIGS. 82 and 83 illustrate cushions with a gel-like membrane and a support wall according to an embodiment of the present invention.
Figure 83:
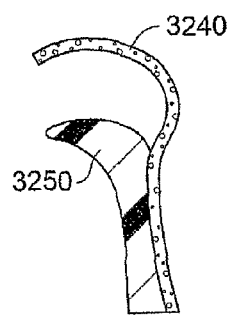

FIGS. 82 and 83 illustrate cushions with a curved gel-like membrane 3240 (i.e., thin, soft gel layer) and a support wall 3250 (i.e., hard support layer) attached thereto. As illustrated, the support wall may be on the inside or the outside of the curved gel-like membrane. In addition, the curved gel-like membrane may have different curvatures along its length as illustrated.

2.1.1.1.4 Round

Figure 49:
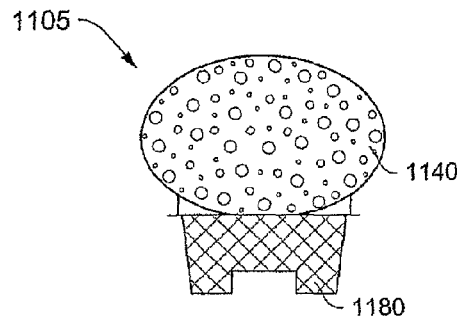
FIG. 49 illustrates a round, chubby soft gel cushion according to an embodiment of the present invention.

FIG. 49 illustrates a very round, oval-shaped soft cushion 1105 (e.g., major axis is horizontal, but could be opposite) with a round membrane and gel 1140 that easily conforms to the face. A cushion clip 1180 is provided to the cushion for engagement with a frame. No supporting structure is required for the cushion, i.e., cushion designed to "mash" onto the face and cushion pressurizes when applied to the face. In this example, only one film encapsulates the gel, which provides fewer processing steps. This shape may used for gels Shore 000 less than 10, for example. In another embodiment, the gel cushion may be egg-shaped with the wider side positioned on the inner or outer radial side of the sealing cushion. Alternatively, the egg-shaped gel may be positioned such that the axis is generally parallel to the cushion axis, with the wider part being either towards atmosphere or towards the patient's face in use.

Figure 50:
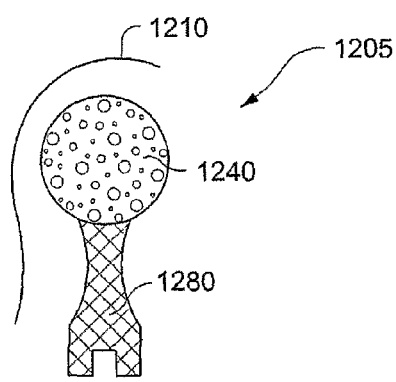
FIG. 50 illustrates a round, soft gel cushion on a long, supporting clip according to an embodiment of the present invention.

FIG. 50 illustrates a generally round, soft cushion 1205 with a round membrane and gel 1240 on a long, supporting clip 1280, which allows the cushion to be used on current frame designs (e.g., ResMed's Activa LT mask). The cushion may be used with a membrane 1210 for enhanced sealing. This shape may used for gels Shore 000 less than 10, for example.

Alternatively a relatively constant bladder cross-section may be used in conjunction with a cushion or supporting clip that varies in height in different regions of the mask providing different levels of support to the patient's face.

Figure 41:
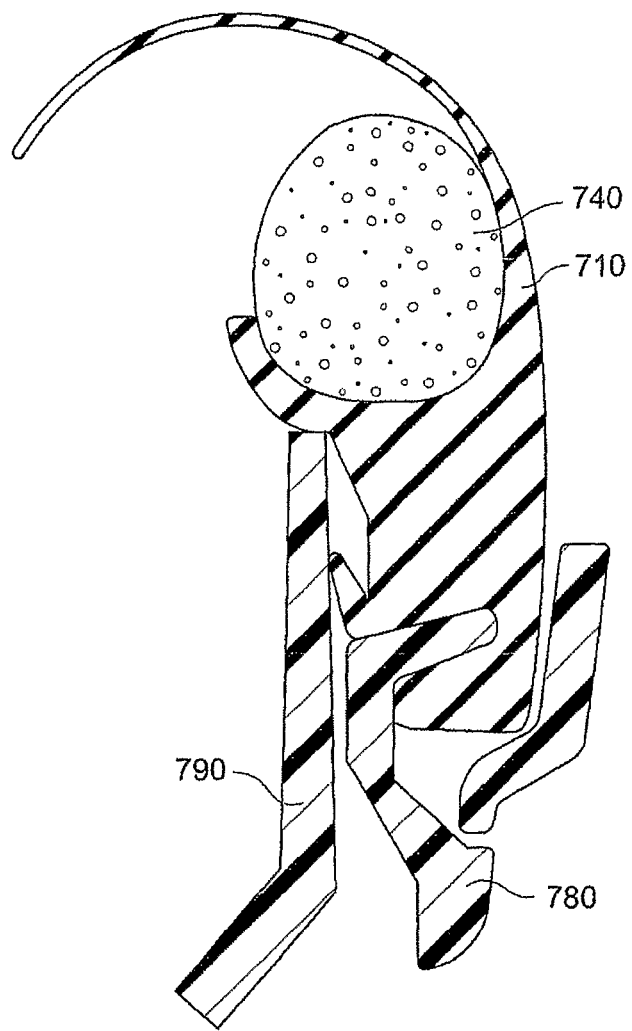
FIG. 41 is a cross-sectional view of a gel cushion according to another embodiment of the present invention.
Figure 42:
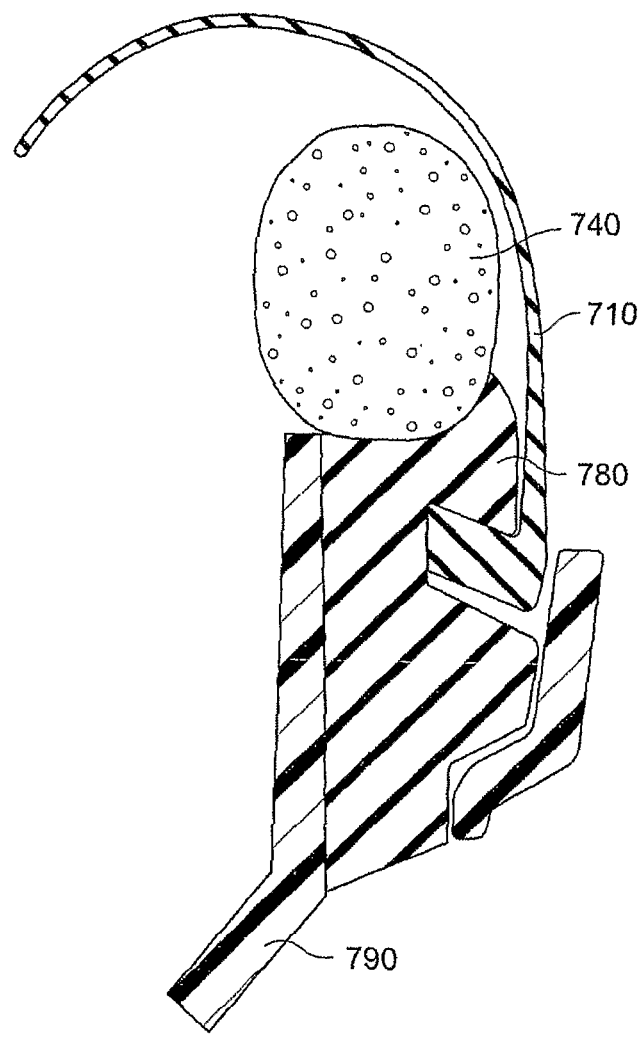
FIG. 42 is a cross-sectional view of a gel cushion according to another embodiment of the present invention.

FIGS. 41 and 42 also show bladders with a rounded configuration (e.g., egg-shaped or oval-shaped).

2.1.1.1.5 Membrane

The bladder may be provided with a membrane. The membrane may provide a seal to the patient's face, provide, comfort, retain the gel in position, and/or prevent gel from contacting face.

The sealing membrane is a flexible layer designed to form a more effective seal between the mask and the patient. This sealing membrane can be made of silicone or any other relatively inelastic or elastic material. In one form, the sealing membrane is formed as a flap of silicone having Shore A hardness in the range of 20 to 60, e.g., 40.

Figure 48:
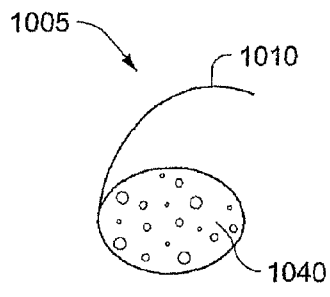
FIG. 48 illustrates a cubby gel cushion according to an embodiment of the present invention.

FIG. 48 illustrates a cushion 1005 with an oval or round and squat shape (i.e., expands radially inwards and outwards). The cushion includes a bladder for gel 1040 and a membrane 1010. This shape may be ideal for gels Shore 000 0-20, which are less hard so will expand outwards, making a larger sealing surface and will also be more comfortable. This shape may also be reasonable for gels Shore 000 20-45, which will not expand outwards as much as the softer gels.

In an embodiment, a "stout" shaped bladder (e.g., oval or egg-shaped with major axis generally parallel with the surface against which a seal is formed) may be used (rather than a long skinny bladder in which major axis is generally vertical with respect to said surface) because seal is maintained by silicone membrane so gel bladder need only provide comfort. The stout shape is like a pressure vessel so may not be comfortable at higher forces (gel has nowhere to spread out to) so can configure cushion to roll, cantilever, or free float under the membrane to move gel into a more comfortable position. Gel tactility may enhance comfort in use.

FIG. 16 also shows a bladder with a membrane, for example.

2.1.1.1.6 Contoured

The shape of the bladder may be configured to provide the most desirable comfort and stability properties to each region of the face, for example, increase comfort at the nasal bridge and increase stability at the cheeks.

For example, FIGS. 9a-9c, 11a, 11b, 17, 19a, 24, 25, 27-29, and 31-35 illustrate bladders 315, that are contoured along its perimeter (e.g., height of bladder varies along its perimeter) to provide comfortable engagement with the patient's face in use. That is, the bladder is structured to allow different amounts or levels of gel in different regions of the patient's face. In addition, the end of the bladder adapted to engage the patient's face may be contoured to more closely follow contours of the patient's face.

As shown in FIGS. 24, 25, and 27-29, the gel cushion 420 may include a nose bridge portion 430 adjacent the patient's nose bridge in use that is adapted to bend towards the side 435 of the frame 415 furthest away from the patient in use. In one embodiment, the undercushion 420 further comprises a hinging portion 455 to help facilitate the bending of the nose bridge portion 430. Preferably, the hinging portion is of narrower width and/or thickness than the nose bridge portion 430.

2.1.1.1.7 Membrane with Bladder Undercushion

The bladder may include a sealing membrane and a fillable undercushion (e.g., undercushion defines cavity) that provides a soft, conforming structure that is comfortable and prevents collapse of the sealing membrane in use. The undercushion can be formed from a bladder filled with one or more materials such as gels, foams, gases and silicones, including silicone oils.

In an embodiment, the sealing membrane includes a free end that is spaced from the undercushion in its substantially relaxed, unstressed state and is adapted to be urged into sealing engagement with the patient's face by the difference between mask pressure and ambient pressure. That is, the membrane and undercushion include adjacent surfaces that face one another and may be spaced apart from one another by a gap. The spacing between the free end of the membrane and the undercushion may be different in different regions of the patient interface.

In an embodiment, the sealing membrane may define a seal forming structure that is structured to engage and provide a seal to the patient's face, and the undercushion may define a cushioning structure to add support and stability to the seal forming structure.

Figure 40:
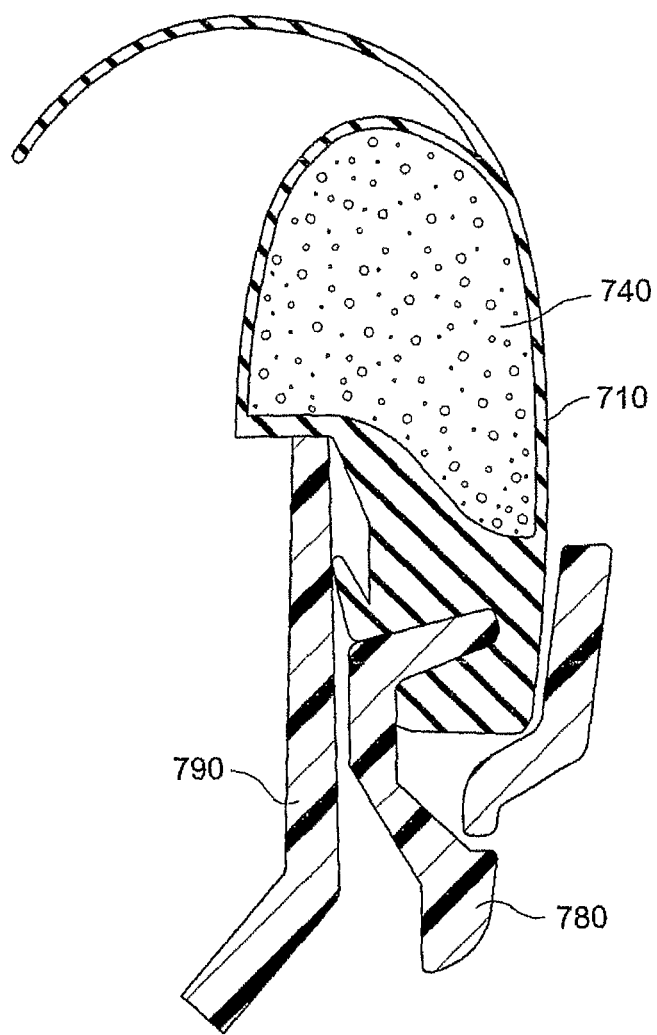
FIG. 40 is a cross-sectional view of a gel cushion according to an embodiment of the present invention.

FIG. 40 illustrates a dual wall cushion including a membrane 710 (e.g., LSR membrane) and gel-filled undercushion 740 (e.g., polyurethane or silicone gel) molded as a one piece component.

FIGS. 191-204 illustrate another embodiment of a gel-filled LSR cushion 700 (e.g., nasal cushion). In this embodiment, the cushion 700 provides a dual wall arrangement including a membrane 710 and an undercushion 715 (FIG. 198) that defines a bladder or cavity for gel. As illustrated, the bladder 746 includes an outer wall 749, an upper wall 748 extending away from the outer wall 749, and an inner wall 747 extends from the free end portion of the upper wall 748, so that the outer wall, upper wall, and inner wall define a bladder or cavity for the gel. The membrane 710 substantially covers the bladder and provides a sealing structure. It should be appreciated that the wall thicknesses (e.g., in the range of 0.25 to 0.75 mm) may be the same or varied.

In the illustrated embodiment, the undercushion is contoured to encourage bending or rolling inwards (i.e., towards the breathing cavity) in use. That is, the end portion of the undercushion is oriented or curved to resiliently bend inwards when force is applied thereto by the membrane in use. The membrane may provide a first level of compliance or spring constant and the undercushion may provide a second level of compliance or spring constant. Preferably, the undercushion is less compliant than the membrane to add support and stability to the membrane in use, however it should be appreciated that the membrane and undercushion may have similar compliances. This arrangement enhances comfort and flexibility of the cushion in use.

FIG. 190 illustrates another embodiment of a gel-filled LSR cushion. In this embodiment, the walls of the undercushion portion include walls of different thicknesses. For example, the inner wall 747 and upper wall 748 include wall thicknesses of about 0.4 mm and the outer wall 749 includes a wall thickness of about 0.6 mm. Different thicknesses may provide different comfort levels for the patient, with a thinner wall being more comfortable.

Figure 143:
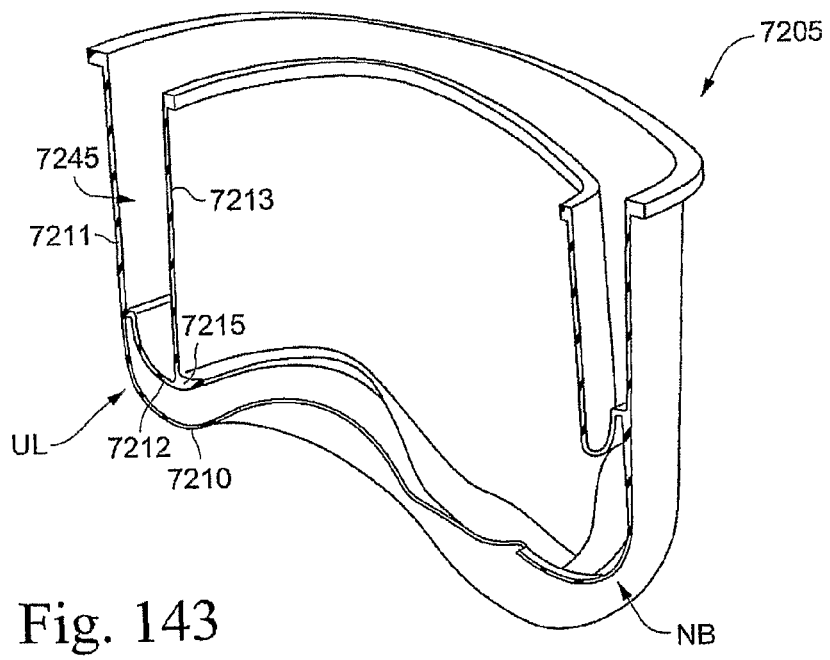
Figure 144:
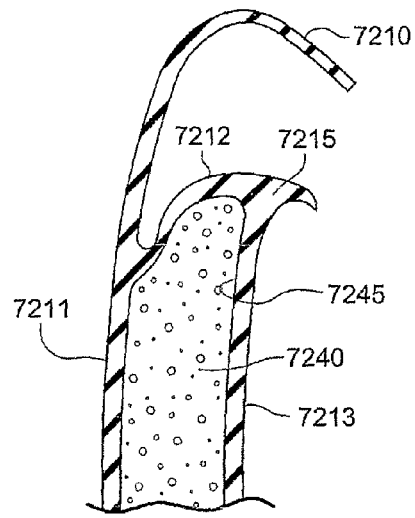

FIGS. 142 and 143 illustrate a cushion 7205 (e.g., constructed of LSR) including a dual wall arrangement (i.e., membrane 7210 and undercushion 7212) with the undercushion 7212 defining a bladder 7245 that can be filled with a cushioning material (e.g., such as gel 7240 shown in FIGS. 144-148).

As illustrated, the face contacting portion includes a base wall 7211, an undercushion 7212 extending away from the base wall 7211, and a membrane 7210 provided to substantially cover the undercushion 7212 and provide a sealing structure. An inner wall 7213 extends from the free end portion of the undercushion 7212, so that the base wall 7211, undercushion 7212, and inner wall 7213 define a bladder 7245 for the cushioning material.

In an embodiment, a thickened portion or bead 7215 may be provided to the free end of the undercushion 7212. For example, as shown in FIGS. 142-146, the thickened portion 7215 may be in the form of an extended bead or overhang that protrudes or extends past the inner wall 7213. Alternatively, as shown in FIG. 147, the thickened portion 7215 may be a thickened end portion or tip of the undercushion 7212. FIG. 148 illustrates an undercushion 7212 and bladder 7245 with no thickened portion or bead, e.g., for comparison. FIG. 146 also shows a cushion 7205 provided to a support 7230 which is secured to a frame 7290 by a cushion clip 7280.

In the illustrated embodiment, the dual wall arrangement with bladder is provided about the entire perimeter of the cushion, i.e., in nasal bridge, cheek, and upper lip/chin regions. The thickened portion or bead may be provided in selected regions of the cushion, e.g., in the upper lip/chin region UL but not in the nasal bridge region NB as shown in FIGS. 142 and 143.

The thickened portion or bead 7215 adds rigidity to the undercushion 7212. Thus, a relatively soft gel 7240 may be provided to the bladder 7245 and the thickness of the thickened portion or bead 7215 may be adjusted to vary the rigidity or the way the cushion feels on the patient's face in use.

Also, the thickened portion or bead 7215 is structured to encourage the cushion to roll inwards (i.e., towards the breathing cavity) in use. For example, the thickened portion or bead 7215 may be oriented or curved to roll inwards when force is applied thereto by the membrane in use.

FIG. 70 illustrates a cushion having a membrane and a three piece polyurethane undercushion 2410(1), 2410(2), 2410(3) and a gel filling 2440. The undercushion encases the gel and the sealing membrane is adapted to contact with the patient's face. This arrangement includes a single cushion and membrane, which provides less assembly time and lower cost.

Figure 96:
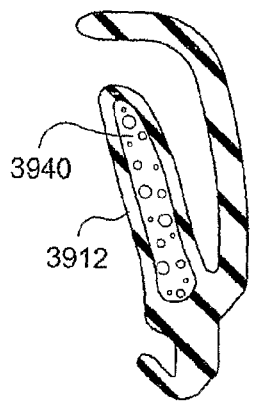
FIGS. 96 and 97 illustrate a single piece cushion with gel injected into a silicone support cushion according to an embodiment of the present invention.
Figure 97:
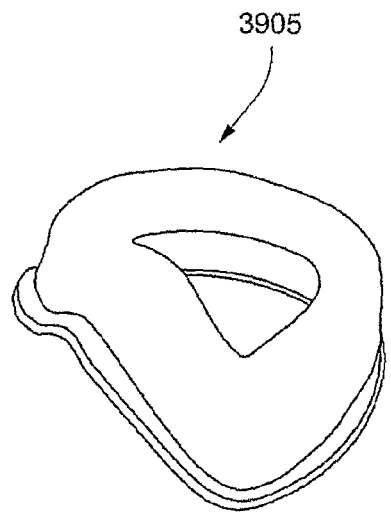

FIGS. 96 and 97 illustrate a single piece cushion 3905 (e.g., constructed of LSR) with gel 3940 injected into the silicone undercushion or support cushion 3912.

2.1.1.2 Gel Skin Properties/Structure

FIG. 117 illustrates a cushion wherein one or more portions of the cushion include a textured surface 5445 (e.g., lattice-like structure 5446 (FIG. 118), small bumps 5447 that easily compress and provide a soft, flowy, or rolling feeling (FIG. 119)) for circulation, pressure relief, or for "soft touch".

In an embodiment, sections of the wall of the skin may be shaped to match contours of the face. FIGS. 120 and 121 illustrate an arrangement wherein a harder outer skin 5545 is pressed over a soft, low durometer gel mass 5540. The harder outer skin compresses the gel mass to form the contoured profile. The skin may be welded to the mass to secure it in position. In this arrangement, certain areas may be compressed more to provide a cushion that feels multi-durometer.

FIG. 122 illustrates a cushion wherein the inner wall of the skin 5645 are pre-stressed or shortened so that the cushion tends inwards.

FIG. 123 illustrates a cushion in which the skin 5745 is relatively thick so it may be used to support the gel 5740, particularly if the gel is a very soft (e.g., Shore 000<10). This may be advantageous should a gel have reduced resilience.

FIG. 124 illustrates a cushion including a thickened inner wall 5850 to enhance the curvature of the cushion and support a very soft gel 5840 (e.g., Shore 000<10).

Figure 125:
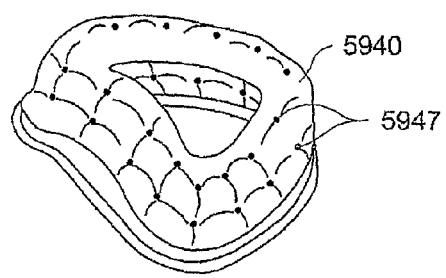
FIGS. 125 and 126 illustrate a cushion that may be constructed of a gel and including spot welds according to an embodiment of the present invention.
Figure 126:
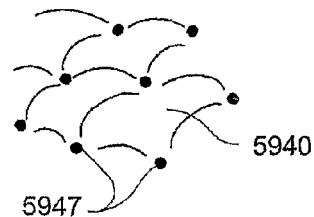

FIGS. 125 and 126 illustrate a cushion that may be constructed using a gel 5940 and including spot welds 5947 to form "pillows" or "pads" that provide structural support.

Figure 127:
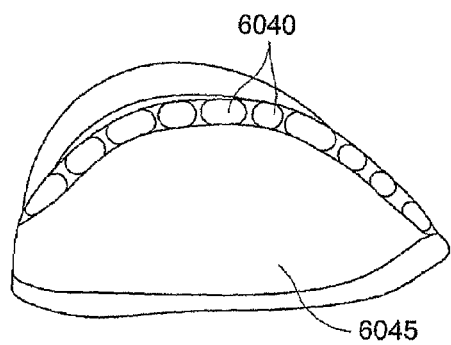
FIG. 127 illustrates a cushion with relatively thick skin and bubbles provided to the skin according to an embodiment of the present invention.

FIG. 127 illustrates a cushion with relatively thick skin 6045 and bubbles 6040 provided to the skin, e.g., bubble wrap style skin. The little pockets filled with a material such as gel, saline, foam or air at the top of the cushion provide comfort in use.

Figure 128:
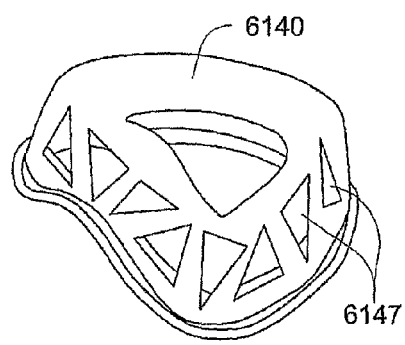
FIG. 128 illustrates a gel cushion with open windows in the gel according to an embodiment of the present invention.

FIG. 128 illustrates a gel cushion 6140 with open windows 6147 in the gel, providing variable structural qualities, such as differing elasticities. The windows may have any suitable shape, may be provided in any suitable number, and may be arranged on the cushion in any suitable manner. The windows may be provided for aesthetics to emphasize the gel properties of the cushion.

Figure 129:
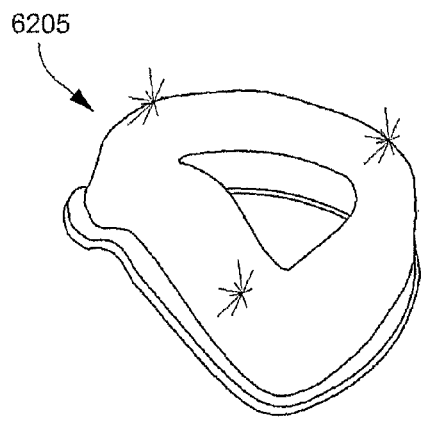
FIGS. 129 and 130 illustrate cushions that are all or partly frosted according to an embodiment of the present invention.
Figure 130:
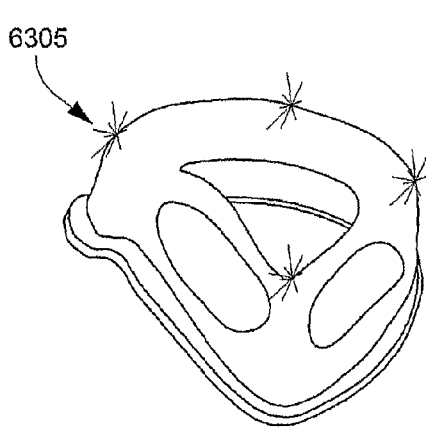

FIGS. 129 and 130 illustrate cushions 6205, 6305 that are all frosted or partly frosted for aesthetics. The frosted cushions may also provide more comfort in use.

Figure 131:
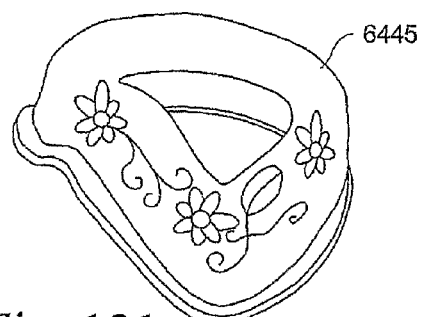

FIG. 131 illustrates a cushion with a skin 6445 made from fabric or textile material for comfort. As illustrated, such material may include one or more designs for aesthetics. In an alternative embodiment, the cushion may include flocking.

In an alternative embodiment, the cushion may include a silicone layer. In such arrangement, the air path is constructed from silicone, a material the biocompatibility is known, allowing the use of gel material with a different biocompatibility.

In another alternative embodiment, the cushion may include wrinkle free skin.

2.1.2 Frame

The gel may be supported by a mask frame. The mask frame provides an interface for supporting and maintaining the mask on the patient's face and for delivering breathable gas to the patient, e.g., interface for gel cushion, elbow assembly, forehead support, and/or headgear. Frames may be made from polycarbonate, polypropylene, silicone, or other materials.

Exemplary frames 140, 415, 510, 790 are shown in FIGS. 3, 4, 24-26, 30, and 202-204.

2.1.2.1 Gel to Frame Interface

The gel may be retained and/or supported by the frame in alternative manners. For example, the gel may include a gel to frame interface that allows the gel to attach directly to the frame. Alternatively, the gel may include a gel to cushion interface that allows the gel to attach to a cushion, and then the cushion includes a gel to frame interface that allows the cushion to attach to the frame.

The gel to frame interface may also provide seal, retention, and assembly/disassembly to the frame/cushion.

2.1.2.1.1 Gel to Frame

Referring to FIGS. 24 to 29, a respiratory mask 410 is shown comprising a frame 415, an undercushion 420, and a membrane 425. The cushion 420, 425 for a respiratory mask 410 is provided comprising a frame engagement portion 440 and a patient interfacing portion 445, the portions 440, 445 being made of different materials and being co-molded. Advantageously, the material chosen for the frame engagement portion 440 can be optimized for its purpose while the material chosen for the patient interfacing portion 445 can be optimized for its purpose. Preferably, the frame engagement portion 440 is made from a more rigid material (i.e., higher durometer) than the patient interfacing portion 445. Advantageously, the patient interfacing portion 445 can be made of a material that is suitable for sealing, tear resistance and is soft, providing comfort advantages while the frame engagement portion 440 can be made of a harder material that is more easily engaged with a corresponding portion of the frame 415 (e.g., by a snap fit, snug fit, or interference fit).

In any of the above embodiments, the undercushion 420 may extend to or towards an inside surface 450 of the front portion of the frame 415 and be adapted to define a lip seal between the mask frame 415 and an elbow of the mask 410.

In one embodiment, the cushion is a membrane and a separate undercushion (e.g., a low durometer undercushion as described in any one of the above embodiments) is provided between the membrane and the frame but is not integrally molded or permanently, sealingly attached to either although it may be supported by either. In another embodiment, the low durometer undercushion is sealingly attached to the frame, and a membrane is sealingly attached to the undercushion. In this embodiment, the frame, undercushion and membrane may all be comolded. In another embodiment, the membrane and undercushion may both be sealingly attached to the frame.

In one embodiment, the mask comprises a cushion having comolded components, i.e., a membrane, a low durometer undercushion, and a frame interfacing portion. The frame interfacing portion is made from a high durometer material to provide a snap fit, the membrane is made from the same material which is also adapted for sealing and tear resistance when manufactured thinly while the undercushion is over-molded in low durometer material for comfort.

FIG. 52 illustrates a solid silicone section 1430 that slots into a channel on a frame 1490 by an interference fit. A gel section 1440 may be permanently attached to the silicone section 1430. A silicone clip 1480 is molded between the gel and silicone sections 1440, 1430 that also clips to outside of the frame 1490. Thus, the silicone section 1430 and clip 1480 sandwich the frame 1490 with an inside/outside connection. A membrane 1410 is molded onto the silicone clip 1480. This arrangement provides a one piece arrangement for ease of assembly.

FIGS. 99 and 100 illustrate cushions in which harder components 4150 are provided to a side or under the gel cushion 4140 to provide an interference fit within the frame channel of the frame 4190. For example, the component 4150 may be co-molded under the gel cushion 4140 as shown in FIG. 99 or may be positioned between the gel cushion 4140 and membrane, e.g., spaced from gel cushion 4140, as shown in FIG. 100.

FIG. 101 illustrates a ring-like frame 4290 with a clamp arrangement wherein the frame is pushed into engagement with the cushion 4205 to force the frame closed and thus capture or clamp the cushion to the frame (e.g., clamp inner and outer cushions to the frame). This arrangement is not limited to gel cushions, e.g., may be used with a foam cushion.

Figure 109:
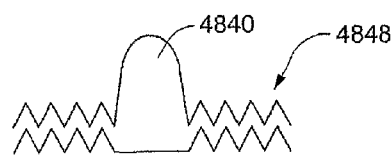
FIGS. 109 and 110 illustrate a cushion with a friction retention feature according to an embodiment of the present invention.
Figure 110:
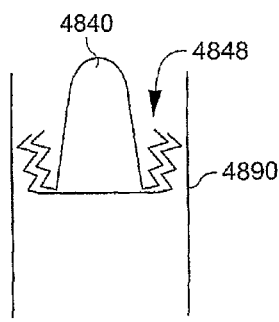

FIGS. 109 and 110 illustrate a cushion 4840 with a friction retention feature 4848 (e.g., one or more arms with crimping, texture, and/or thickening) that can be interference fit with the frame 4890.

Figure 111:
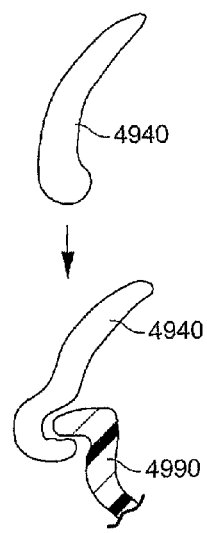
FIG. 111 illustrates a gel cushion structured to be wrapped around a frame according to an embodiment of the present invention.

FIG. 111 illustrates an arrangement wherein the elasticity of the gel cushion 4940 is used to wrap or slip the gel cushion around frame 4990 (e.g., gel sock). That is, the gel may be deformed to grip or clasp the frame. An external ridge on the frame prevents the gel cushion from disconnecting from the frame.

Figure 112:
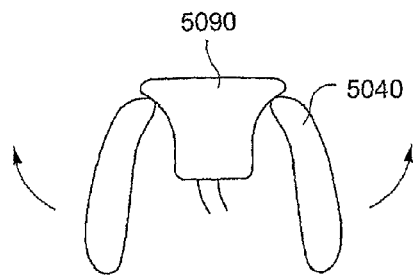
FIGS. 112 and 113 illustrate a gel cushion structured to flip around a frame according to an embodiment of the present invention.
Figure 113:
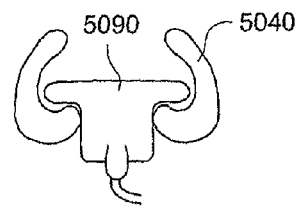

FIGS. 112 and 113 illustrate an arrangement wherein the gel cushion 5040 is structured to flip around the frame 5090. That is, ends of the gel cushion 5040 may be moved into engagement with the frame (FIG. 112) and then the gel cushion may be flipped inside out which allows the ends to grip or clasp the frame (FIG. 113).

Figure 114:
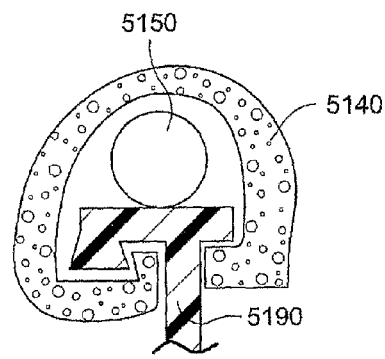
FIG. 114 illustrates a gel wrapped around a frame channel according to an embodiment of the present invention.

FIG. 114 illustrates an arrangement wherein the gel 5140 is wrapped around the frame channel of frame 5190. As illustrated, the gel may encapsulate another gel or an air pocket 5150 or any other material for spring.

Figure 115:
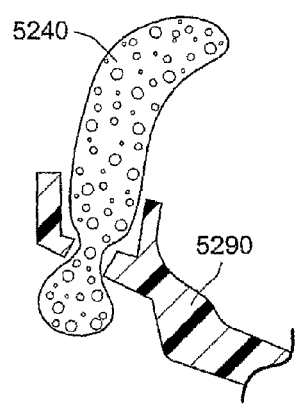
FIG. 115 illustrates a gel pushed through a channel in the frame according to an embodiment of the present invention.

FIG. 115 illustrates an arrangement wherein the gel 5240 pushes through a channel in the frame 5290 for a one way mechanical lock with the frame (e.g., gel forms retention bulge or protrusion structured to retain gel to frame).

Figure 106:
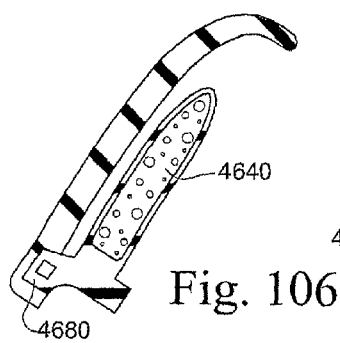
FIGS. 106 and 107 illustrate a frame/clip and cushion co-molded or over-molded as one part according to an embodiment of the present invention.
Figure 107:
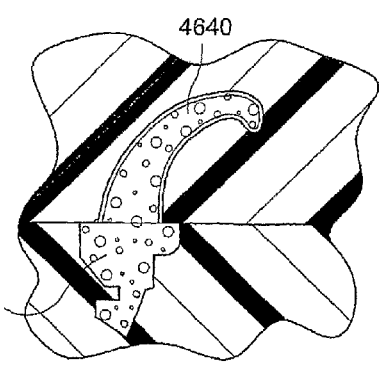

FIGS. 106 and 107 illustrate a frame/clip 4680 and cushion 4640 which is co-molded or over-molded as one part. FIG. 107 illustrates a skinned gel portion 4640 (which has already set) chemically bonded to clip 4680 formed of an unskinned, "rubber" duro gel portion.

Figure 108:
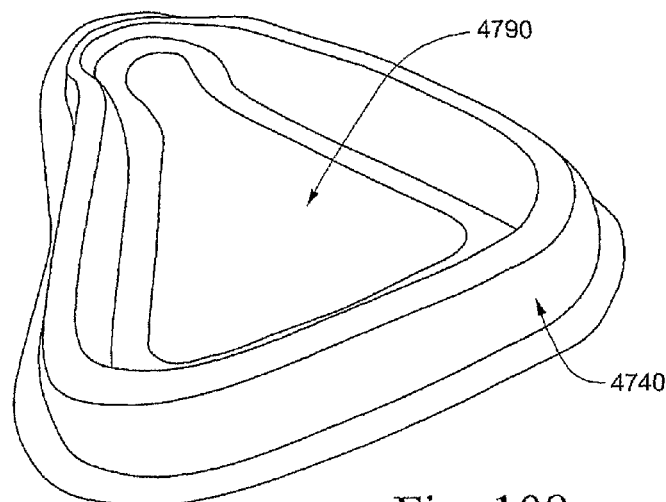
FIG. 108 illustrates a single bladder forming a cushion and frame according to an embodiment of the present invention.

FIG. 108 illustrates a single bladder forming a cushion 4740 and frame 4790. The bladder may be separated into two chambers, one chamber holding gel and the other chamber holding a more rigid material. The single bladder may be stamped in a mold and then each chamber filled with the desired materials.

In an alternative embodiment, the frame or cushion clip may be the plug in plug-assisted vacuum-forming. For example, the gel skin is placed over the mold cavity, the frame pushes the skin into the mold, the skin is vacuumed onto the sides of the mold cavity, the mold is cooled to set the skin, then gel is filled into the skin and around the frame, then the skin is welded onto the frame. The frame will extend into the gel cushion in some way (either all of the way or only a portion of the way) meaning that softer gels can be used as there is a supporting wall through the cushion. The mask may be sold as one piece or the cushion and cushion clip may be sold as one piece.

Figure 116:
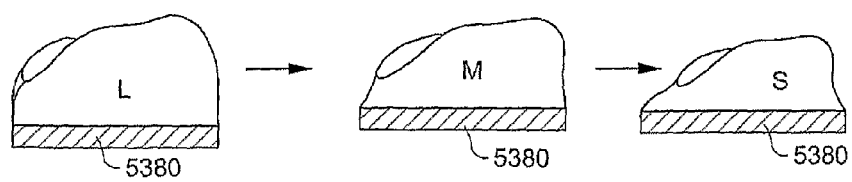
FIG. 116 illustrates an one size fits all cushion clip according to an embodiment of the present invention.

FIG. 116 illustrates a one size fits all cushion clip 5380 wherein the cushion clip can be attached to various sizes of cushion (e.g., large (L), medium (M), and small (S)), i.e., user can interchange cushion on cushion clip. Such arrangement minimizes the number of mask parts.

FIGS. 13*a*, 13*b* 14, 20, 49, 50, 55, 58-60, 64, 103, 123, and 124 also show alternative frame engaging portions and/or cushion clips provided to the gel for engagement with a frame.

2.1.2.1.1.1 Seal with Frame

In certain applications, it may be desirable for as much as possible of the mask system to be sterilizable or at least cleanable so that it is suitable for multi-patient multi-use (MPMU). Some forms of cushion may not be able to withstand the sterilization or cleaning process. Other forms of cushion may be easier to clean when a separate component. Hence, it may be desirable to make the cushioning element removable from the frame or shell.

In order to attach the cushioning component to the frame of the mask system, a cushion clip can be interfaced between the cushion and the frame. A cushion clip may be a made from a flexible material such as polyurethane, or a more rigid material such as polycarbonate. In an embodiment, the cushion is permanently or semi-permanently attached to the cushion clip. In an alternative embodiment, the cushion is permanently attached to the frame.

Gel-filled cushions typically have an outer film or bladder surrounding the gel and substantially sealed against leakage. This outer film or membrane can be made from a flexible material, such as polyurethane. The outer film may be formed from one or more sheets or films of the flexible material or a combination of a flexible material and a rigid or semi-rigid materials. In an embodiment, the outer film is continuous such that the gel is sealed within the film. This may be preferable for disinfection of the cushion and also meets disinfection standards for MPMU (Multi-Patient-Multi-Use).

Figure 36:
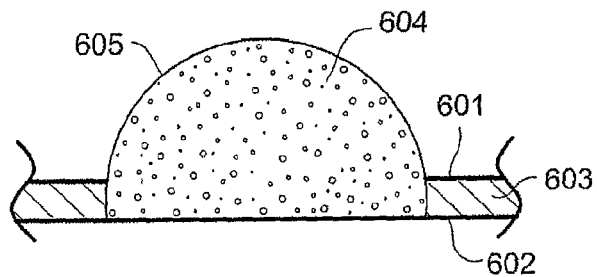
FIG. 36 shows a gel cushion with a sealed film or membrane according to an embodiment of the present invention.

For the outer film to be continuous and sealed, the sheets of flexible material may be joined forming a seal edge to prevent leakage of gel. The joining of the flexible material may be achieved by securing the ends of the flexible material sheets at the seal edge, for example, by gluing, welding, or any other reasonable means. An example of such a configuration is shown in FIG. 36 where flexible plastic piece 601 has been joined to flexible plastic piece 602 along joint 603, encasing a gel 604. An outer membrane 605 is provided to the gel 604.

However, a cushioning element can cause discomfort because of the positioning of a seal edge where it may contact the skin of a person wearing the mask.

Figure 37:
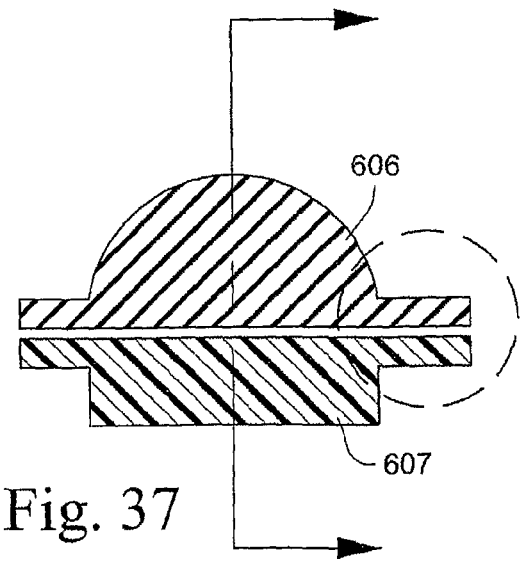
FIG. 37 shows the engagement of a cushion to a cushion clip.

In some applications, the structure containing gel may include a rigid (or semi-rigid) component, either internally or as part of a sidewall. The rigid component may function as a cushion clip. Where the rigid component forms a sidewall, in order to form a joint between the thin film material and the rigid component, it may be necessary to include an edge portion in the rigid component (clip 607) to which may be welded an edge of the film of cushion 606, forming the seal edge or mating surface, as shown in FIG. 37. Depending on the way that a bond is formed between the film and the rigid component, it may be necessary for the rigid component to include a thin, rigid projecting rim or lip region, for example at an angle of about 90 degrees to the rigid component. Such a projecting rim or lip could impinge on the nose of the patient in use.

In an embodiment, engagement of the joint with the mating surface may be achieved by Radio Frequency (RF) welding. However, alternative methods may be utilized, e.g., gluing or co-molding. The engagement may occur on the side of the mask that is closest to the patient's nose and/or mouth (as shown in FIG. 37).

Figure 38:
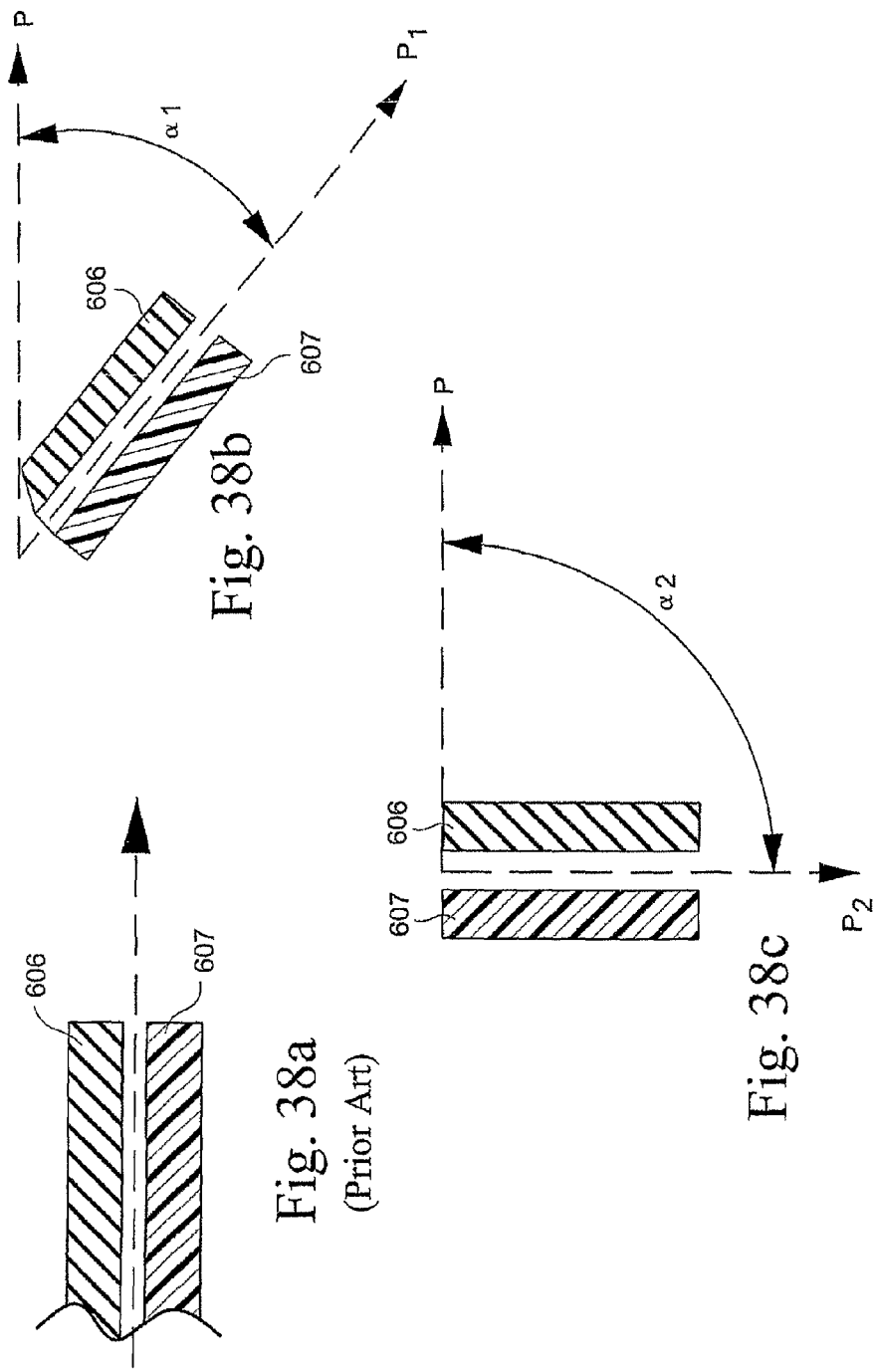
FIG. 38a shows a detail view from FIG. 37.
FIG. 38b shows an alternative form of the detail view from FIG. 37 according to an embodiment of the present invention.
FIG. 38c shows an alternative form of the detail view from FIG. 37 according to another embodiment of the present invention.
Figure 39:
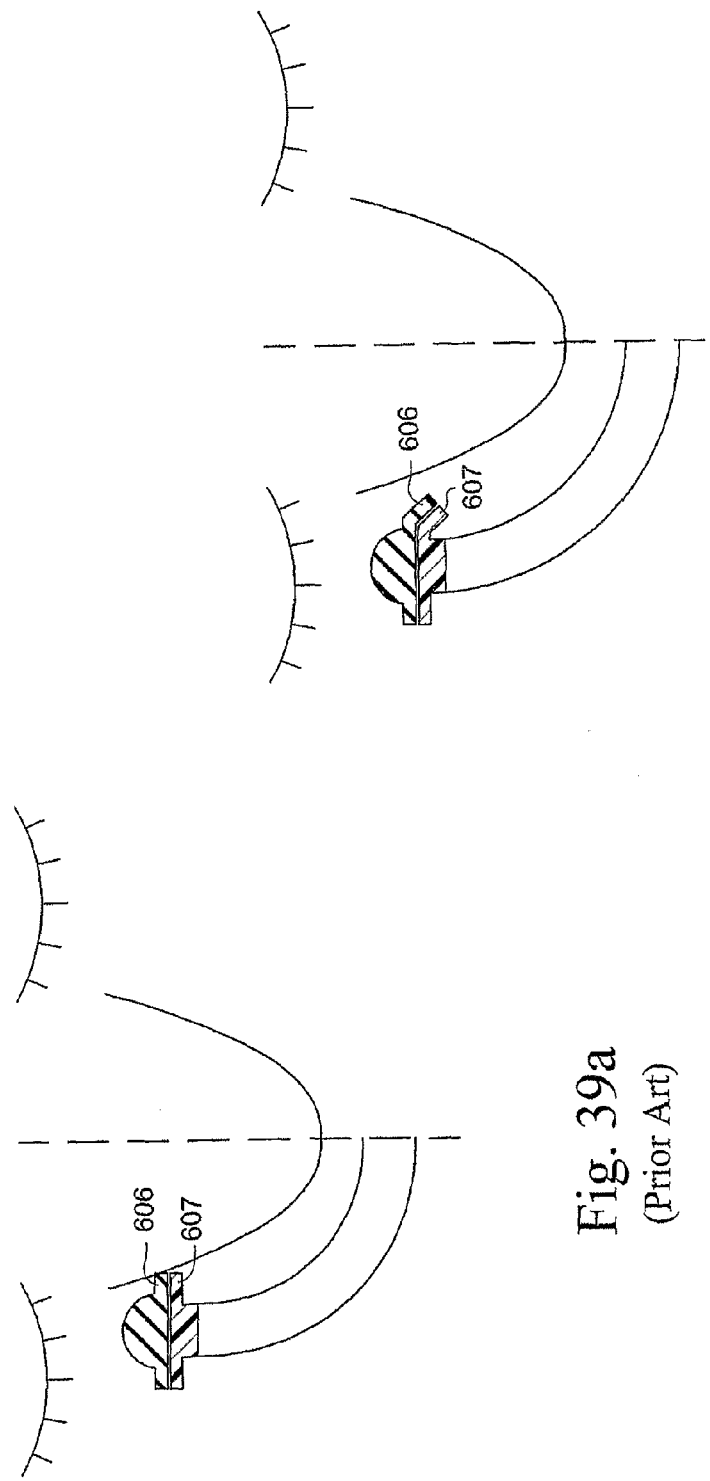
FIG. 39a shows a mask in use where the seal edge may impinge on the nose of a patient.
FIG. 39b shows a mask in use with a seal edge at an angled position according to an embodiment of the invention.

In prior art masks, the engagement of the joint on the cushion 606 with the mating surface on the frame or cushion clip 607 has been at 0° or on plane P as shown in FIG. 38*a*. FIG. 39*a* shows how this configuration can interfere with and cause discomfort to the patient.

Hence, in accordance with an embodiment of the invention, the projecting rim or lip region is arranged in a way so that it does not impinge on the nose of the patient in use. For example, the rim may be angled to be less than 90 degrees.

In accordance with an embodiment of the invention, the seal edge is angled so that it is more comfortable for the patient. In an embodiment, the engagement of the join on the cushion with the mating surface on the cushion clip may be angled below plane P. In one form, the engagement may be less than 180°. In one form, the engagement may be less than 90°. In another form, the engagement may be less than 45°. In another form, the engagement may be 60°. In another form, the engagement may be 45°. In another form, the engagement may be 30°. Examples of these forms are shown in FIGS. 38*b* and 38*b*, where the angle $\alpha 1$ of engagement at $P_1$ is about 45° and the angle $\alpha 2$ of engagement at $P_2$ is about 90°. FIG. 39*b* shows how an angled configuration may improve the comfort of the mask system for the patient.

2.1.2.1.2 Gel to Cushion

The gel may be supported by and/or attached to a cushion (e.g., via a gel to cushion interface) and then the cushion may be attached to the frame. In such embodiments, the cushion may be manufactured as two or more components (e.g., membrane and gel bladder formed separately and coupled to one another) or the cushion may be manufactured as a single component (e.g., membrane and gel bladder molded as a one piece component).

2.1.2.1.2.1 Two Components

In the two component configuration, the separately made gel bladder may be coupled to the membrane (e.g., LSR membrane) in alternative manners, e.g., "tuckable" (in which the gel bladder is tucked or inserted into a pocket within the membrane) and "stackable" (in which the gel bladder forms part of an assembly that is stacked or otherwise interlocked with the membrane), as discussed further below. In each embodiment, the inside of the LSR membrane or gel bladder may be frosted so that the parts can be easily aligned. This arrangement provides more choice of gel since the gel is not enclosed or formed with the LSR membrane but made separately.

In an alternative embodiment, a gel with no skin may be provided to a cushion, wherein the silicone membrane of the cushion seals the cushion on the patient's face and also protects the gel from external contaminants.

"Tuckable"

FIG. 41 illustrates a tuckable cushion arrangement in which the cushion includes a membrane 710 (e.g., LSR membrane) with a pocket to receive a separately made gel bladder 740 (e.g., polyurethane gel with polyurethane skin). An existing cushion clip 780 (e.g., ResMed's Quattro clip) may be used to secure the cushion to an existing frame 790 (e.g., ResMed's Quattro frame). As illustrated, the membrane includes a seal lip structured to form a seal with the frame.

FIGS. 149 and 150 illustrate exemplary methods for tucking or inserting the gel bladder into the cushion pocket and under the membrane. In FIG. 149, the gel bladder 740 is tucked into the pocket of a cushion 710 that is already attached to the mask frame 790. In FIG. 150, the gel bladder 740 is tucked into the pocket of a cushion 710, and then the cushion 710 with gel bladder 740 is subsequently attached to the mask frame 790. In these embodiments, the cushion 710 is provided with an existing cushion clip 780 (e.g., ResMed's Quattro clip) that is used to secure the cushion 710 to an existing frame 790 (e.g., ResMed's Quattro frame). However, it should be appreciated that the cushion may be retained to the frame in other suitable manners (e.g., ResMed's Liberty/Vista retention designs). Also, it should be appreciated that FIGS. 149 and 150 may simply illustrate an exemplary method for inserting a gel bladder to a cushion, i.e., regardless of gel/cushion arrangement.

The cushion and tuckable gel bladder may include alternative structures to that described above to facilitate assembly and detainment of the gel bladder to the cushion. For example, the gel bladder may include a polyurethane skin all around it ("flexible gel" as shown in FIG. 41), a polyurethane skin with silicone backing ("semi-rigid gel"), a relatively thick silicone backing to provide a "dual durometer" arrangement, an arrangement that allows various backings/rigidizing components to be modified or added ("rigid gel"), and/or an arrangement such that the gel bladder is modeled to approximate the position and an undercushion (e.g., undercushion of ResMed's Quattro cushion). The cushion may be structured by modifying an existing cushion (ResMed's Quattro cushion) to include a recessed area or shelf to support the gel bladder, e.g., remove existing undercushion. The cushion may be attached to a frame via a cushion clip ("rigid cushion"), which allows precise alignment of the cushion to the frame. However, the cushion may be attached to a frame without a cushion clip ("flexible cushion").

FIGS. 151-153 illustrate alternative cushions with tuckable gel bladders. For example, FIG. 151 illustrates a one-action locking arrangement in which the cushion includes a membrane 710 and a flexible arm 711 that defines a pocket 760 to receive the gel bladder 740. When the cushion is secured to the frame 790, the wall of the cushion channel deflects the arm 711 into engagement with the bladder 740 to securely retain the gel bladder within the pocket 760. FIG. 152 illustrates a gel bladder 740 (e.g., polyurethane gel with polyurethane skin) with a clip 742 (e.g., polyurethane clip) provided to the base of the gel bladder 740 (e.g., polyurethane skin of the gel bladder welded or molded to the polyurethane clip). The membrane 710 includes a recess 712 adapted to receive the clip 742 to securely retain the gel bladder 740 to the cushion. Also, the cushion provides a sealing flap 770 adapted to engage the frame. FIG. 153 illustrates a cushion with a reverse or outside/exterior pocket arrangement to receive the gel bladder 740, i.e., pocket 760 for gel bladder provided along cushion exterior rather than cushion interior. In such embodiment, the gel bladder 740 may be provided as two elongated pieces (rather than a one-piece loop) that cooperate to extend around the cushion perimeter.

FIGS. 154 and 155 illustrate a tuckable gel bladder 740 including a flexible gel 741 with a harder silicone backing 742. The gel bladder 740 may be tucked into the pocket 760 of a cushion 710, which includes a cushion clip 780 for securing the cushion to a frame 790. The cushion and cushion clip may be referred to as a relatively rigid cushion.

FIG. 156 illustrates a tuckable gel bladder 740 including a gel 741 and a rigid support 742 bonded or otherwise attached to the gel. The gel and rigid support may be referred to as a relatively rigid gel. As shown in FIG. 157A, the gel bladder 740 may be tucked into the pocket 760 of a cushion 710, with the rigid support 742 of the gel bladder supported by the frame 790. As illustrated, the cushion 710 may be attached to the frame 790 without a cushion clip.

In an alternative embodiment, the cushion may include a cushion clip for securing the cushion to the frame. As shown in FIG. 157B, the rigid support 742 supporting the gel 741 may be abbreviated or shortened, so that the rigid support 742 and cushion clip 780 are not in the same vertical position around the cushion perimeter to maintain cushion flexibility.

Figure 158:
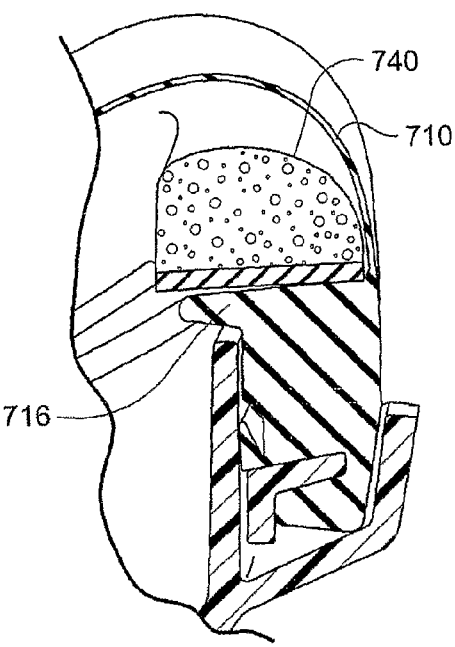

FIG. 158 illustrates a cushion 710 (e.g., LSR cushion) with a well-defined locating shelf 716 for supporting a gel bladder 740 (e.g., silicone backed gel (dual duro)). The well-defined location in the cushion provides intuitive assembly and gives the user feedback that assembly has been done correctly. In contrast, FIG. 155, for example, does not provide a well-defined gel location in the cushion, e.g., no shelf. In an embodiment, inner surfaces of the cushion may be frosted to facilitate assembly. Also, the gel may be designed for seal and size (anthropometry).

Figure 159:
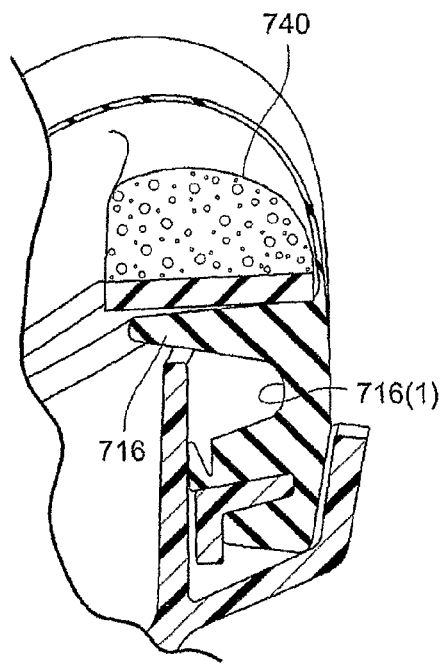

As shown in FIG. 159, a portion 716(1) of the locating shelf 716 may be cored out or removed to facilitate manufacturing, e.g., core out may facilitate demolding and lower cycle time. In addition, the cored out shelf may enhance gel softness or comfort by adding flexibility or springiness to the shelf. Ribs may be added to the core out to tweak shelf flexibility.

FIG. 160 illustrates a tuckable embodiment in which the gel bladder 740 includes a hard or rigid clip 742. As illustrated, the gel bladder 740 includes a gel 741 and a rigid clip 742 bonded or otherwise attached to the gel 741. The rigid clip 742 includes a tab 742(1) that is adapted to be fit (e.g., interference fit) into a slot 712 provided in the locating shelf of the cushion 710. The cushion 710 may include a cushion clip 780 for securing the cushion to the frame 790.

In an embodiment, as shown in FIG. 161, the cushion 710 may be first assembled to the frame 790, and then the gel bladder 740 may be tucked into the cushion membrane where the tab 742(1) can be located and pushed into engagement with the slot 712 in the locating shelf. In an alternative embodiment, the gel bladder may be first tucked into the cushion membrane where the tab can be located and pushed into engagement with the slot in the locating shelf, and then the cushion may be assembled to the frame. In such embodiment, pushing the cushion into the frame may also effect engagement of the tab with the slot in the locating shelf.

FIGS. 162 and 163 illustrate embodiments of a gel bladder 740 with a hard clip 742, wherein the hard clip 742 provides a shape that corresponds to or matches the shape of the locating shelf 716. For example, the hard clip 742 of FIG. 162 provides a sloped configuration to match the sloped configuration of the locating shelf 716, and the hard clip 742 of FIG. 163 provides an arcuate configuration to match the arcuate configuration of the locating shelf 716. As shown in FIG. 163, the gel bladder provides a generally egg shape.

Figure 175:
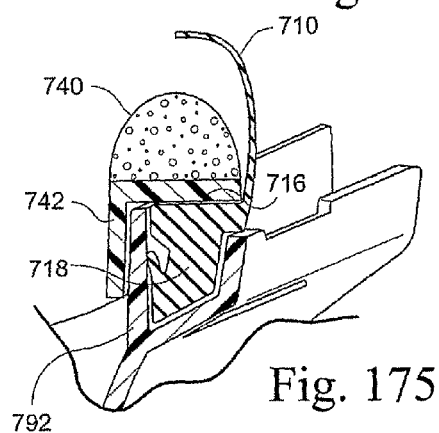

In FIG. 175, the hard or rigid clip 742 of the gel bladder 740 includes an L-shaped configuration such that one leg is supported by the locating shelf 716 and the other leg overhangs the outer wall 792 of the frame channel. As illustrated, the base 718 of the cushion 710 is structured such that the locating shelf 716 is substantially flush with the end of the outer wall 792 when inserted into the frame channel. In addition, the base 718 of the cushion may be retained within the frame channel without a cushion clip.

Figure 164:
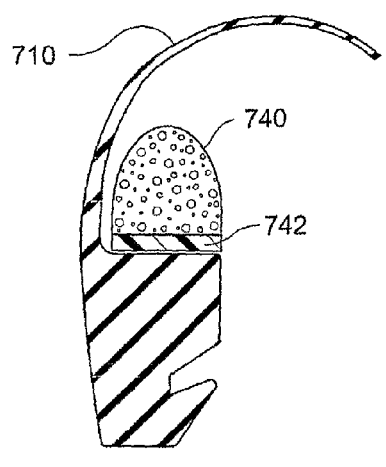
Figure 165:
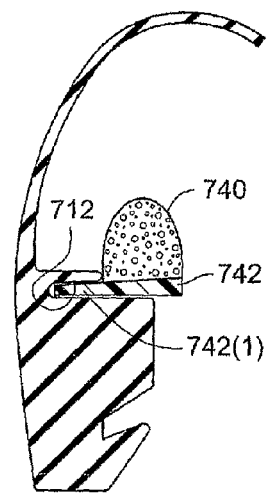
Figure 166:
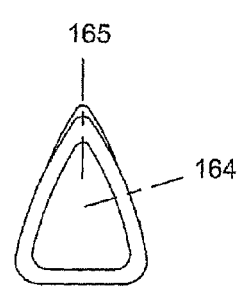

As shown in FIG. 164, the gel bladder 740 sits in the cushion 710 along the line of draw of the cushion. To aid location, portions of the gel bladder 740 may be structured to tuck or extend into the cushion (e.g., clip 742 includes laterally extending tab 742(1) adapted to be inserted into a lateral slot 712 provided in the locating shelf of the cushion as shown in FIG. 165). For example, as shown in FIG. 166, FIG. 164 may represent a section along line 164 of FIG. 166 and FIG. 165 may represent a section along line 165 of FIG. 166, which indicates that the gel bladder 740 may be adapted to tuck into an upper portion of the cushion (e.g., nasal bridge region).

Figure 167:
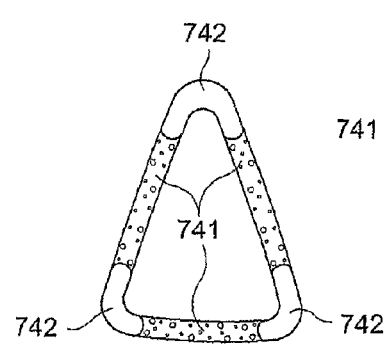
Figure 168:
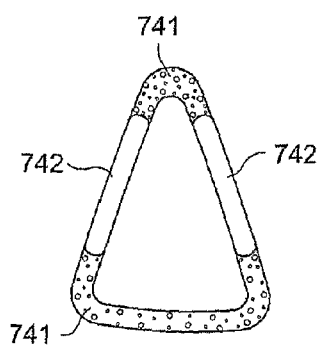

The hard clip 742 of the gel bladder 740 may extend around the entire perimeter of the gel or the hard clip may extend around selected portions of the perimeter of the gel. For example, FIGS. 167 and 168 are alternative rear views of the gel bladder showing selected portions of the gel 741 provided with the hard clip 742. Such partial hard clip may facilitate its use with existing cushion clips adapted to secure the cushion to the frame, e.g., hard clip and cushion clip provided in alternative positions around the cushion perimeter to maintain cushion flexibility (e.g., hard clip and cushion clip in same position along cushion perimeter may cause the cushion to become too firm).

Figure 169:
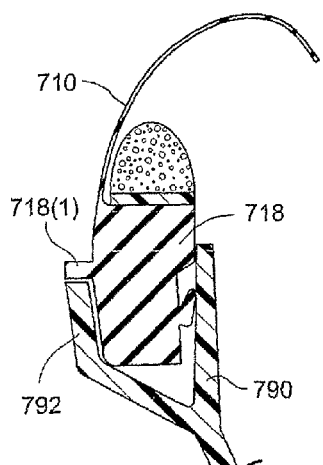
Figure 170:
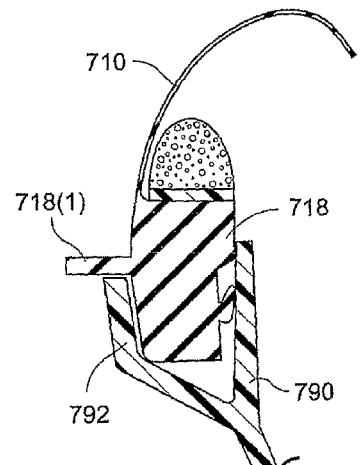
Figure 171:
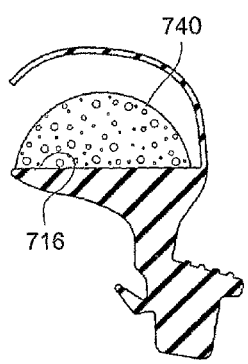

FIGS. 169 and 170 illustrate a cushion arrangement to facilitate assembly/disassembly of the cushion to the frame. As shown in FIG. 169, the base 718 of the cushion 710 includes a tab 718(1) that extends laterally outwardly from an exterior surface of the cushion. Such tab 718(1) extends around the entire perimeter of the cushion. When the cushion 710 is assembled to the frame 790, the tab 718(1) provides an area for pushing the cushion 710 into engagement with the frame 790. As illustrated, the tab 718(1) is adapted to engage the free end of the outer wall 792 of the frame channel when the cushion is fully inserted.

As shown in FIG. 170, one or more selected portions of the tab 718(1) include an extended length that is adapted to overhang the outer wall 792 of the frame channel. Such overhang provides a finger grip to facilitate removal of the cushion 710 from the frame 790, e.g., overhang may be pulled in the direction of the arrow in FIG. 170 to disassemble.

Figure 172:
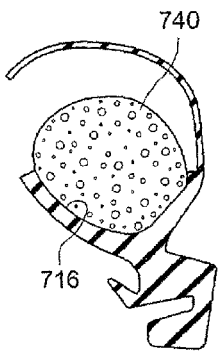
Figure 173:
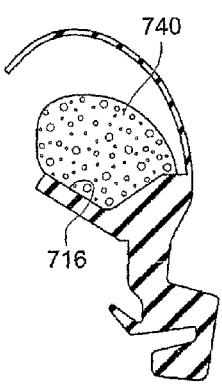
Figure 174:
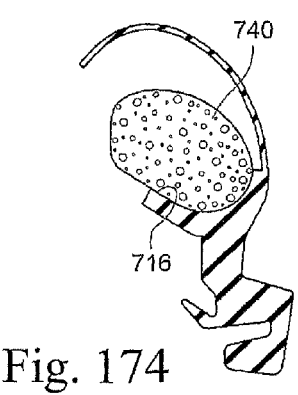

FIGS. 171 to 174 illustrate alternative configurations of the locating shelf 716 in the cushion for supporting the gel bladder 740. As illustrated, the shelf 716 may be relatively flat (FIG. 171), or the shelf 716 may be more curved or cup-shaped to cradle the gel bladder 740 (FIGS. 172-174). The configuration of the shelf may be the same around the cushion perimeter, or the configuration of the shelf may vary around the perimeter of the cushion. In an embodiment, the shelf may be an existing undercushion of a cushion.

Figure 176:
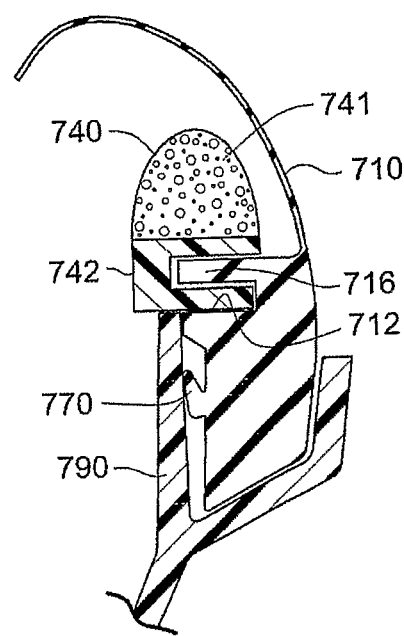

FIG. 176 illustrates an embodiment in which the gel bladder 740 includes a gel 741 and a rigid, c-shaped clip 742 bonded or otherwise attached to the gel. The cushion 710 includes a locating shelf 716 and a slot 712 adjacent the shelf 716. The clip 742 is adapted to interlock with the shelf 716 such that one arm of the clip extends into the slot 712 and the other arm of the clip overhangs the shelf 716. Such arrangement securely locates and retains the gel bladder in position. In addition, the clip facilitates alignment of the cushion with the frame. The base of the membrane may include a sealing lip 770 for sealing against the frame 790.

Figure 84:
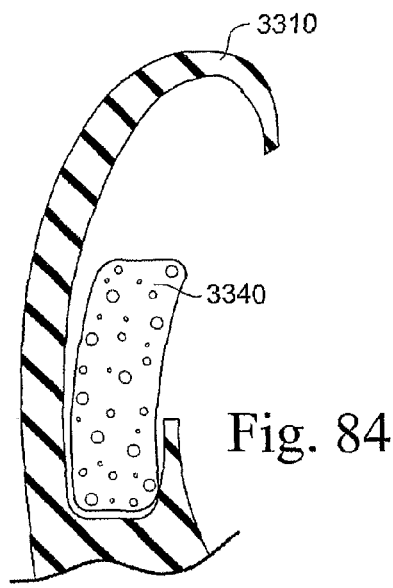
FIGS. 84 and 85 illustrate a cushion with gel underneath the membrane according to an embodiment of the present invention.
Figure 85:
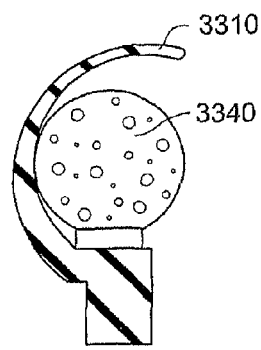

FIGS. 84 and 85 illustrate a typical cushion alignment with the gel 3340 underneath the membrane 3310 and within the frame channel.

FIGS. 88 and 89 illustrate a gel 3540 provided to the outside of the cushion membrane 3510 for cushioning and support. Such arrangement may also be aesthetically pleasing as the gel is visible. As illustrated, the membrane is s-shaped to form a seal with patient's face.

Figure 90:
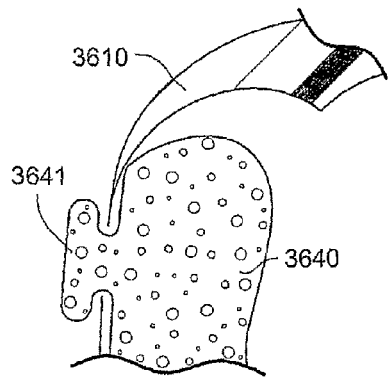
FIGS. 90 and 91 illustrate a gel cushion with a small portion of the gel extending outside the membrane according to an embodiment of the present invention.
Figure 91:
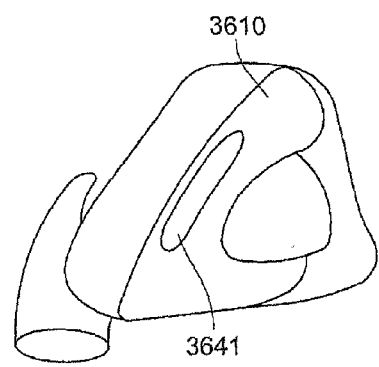

FIGS. 90 and 91 illustrate a predominantly gel cushion 3640 under a membrane 3610, however a small portion of the gel 3641 may extend outside of the membrane for the patient to touch (e.g., soft touch spots or points). The touch spots may be on the outer edge or top portion of the cushion. Such arrangement may provide an aesthetic feature.

Figure 92:
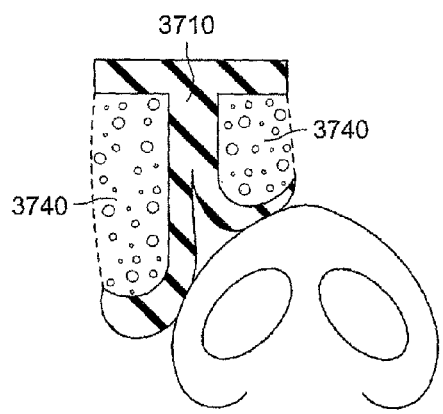
FIG. 92 illustrates a dual wall membrane with a gel according to an embodiment of the present invention.

FIG. 92 illustrates a dual wall membrane 3710 with a gel 3740. As illustrated, the walls may extend in opposite directions and the gel may be provided under both walls. The double cushioning affect as well as aesthetic gel provide an appearance of comfort.

Figure 93:
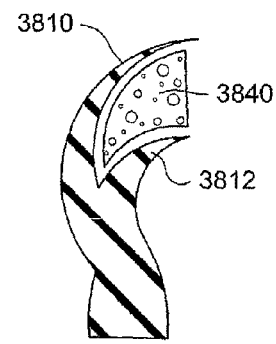
FIGS. 93, 94, and 95 illustrate a gel insert inserted between a silicone support cushion and silicone sealing membrane according to an embodiment of the present invention.
Figure 94:
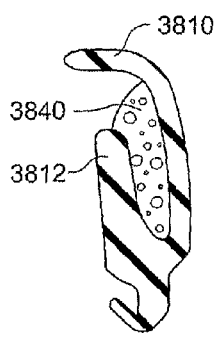
Figure 95:
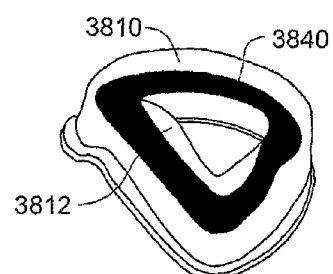

FIGS. 93 to 95 illustrate a gel insert 3840 inserted between a silicone support cushion 3812 and silicone sealing membrane 3810 (e.g., dual wall cushion constructed of LSR). The gel insert is provided for comfort so it may be very soft, e.g., Shore 000<10-20. The gel insert may be retrofitted to currently available masks, e.g., ResMed's Quattro mask.

Figure 98:
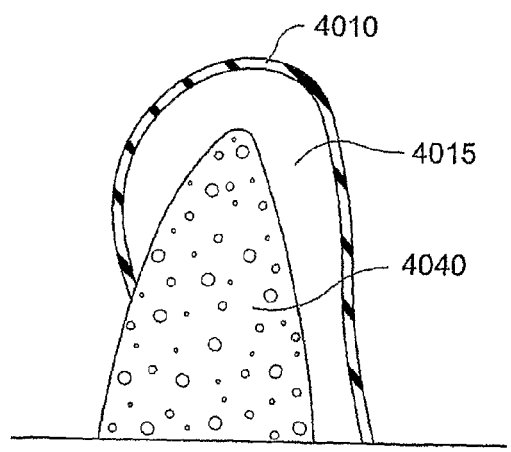
FIG. 98 illustrates a cushion with an air pocket between the gel and the face contacting membrane according to an embodiment of the present invention.

FIG. 98 illustrates a cushion with an air pocket 4015 between the gel 4040 and the face contacting membrane 4010. The air pocket provides an additional spring/gusset to the cushion.

Figure 102:
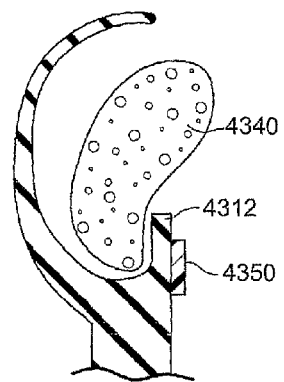
FIG. 102 illustrates a rib provided to a frame and structured to maintain a soft gel cushion in place according to an embodiment of the present invention.

FIG. 102 illustrates a silicone support rib 4312 and an optional rigid component 4350 (e.g., provided to the frame) that are structured to maintain the soft gel cushion 4340 in place.

Figure 3:
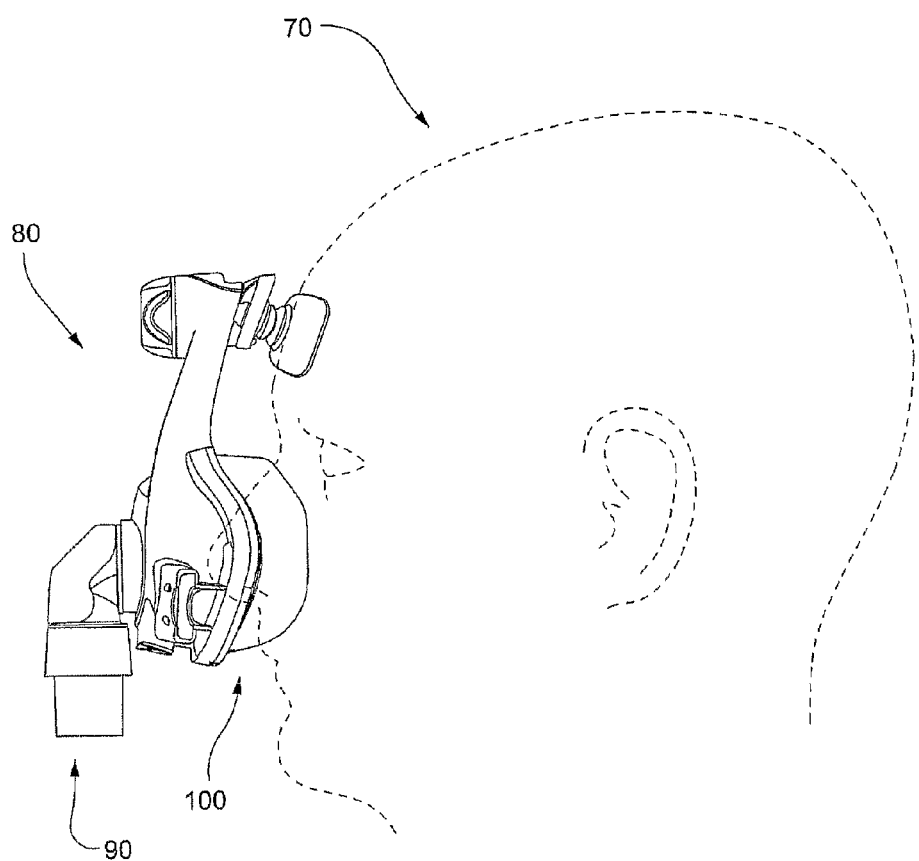
FIG. 3 shows a respiratory mask assembly in position in relation to the head of a patient.
Figure 4:
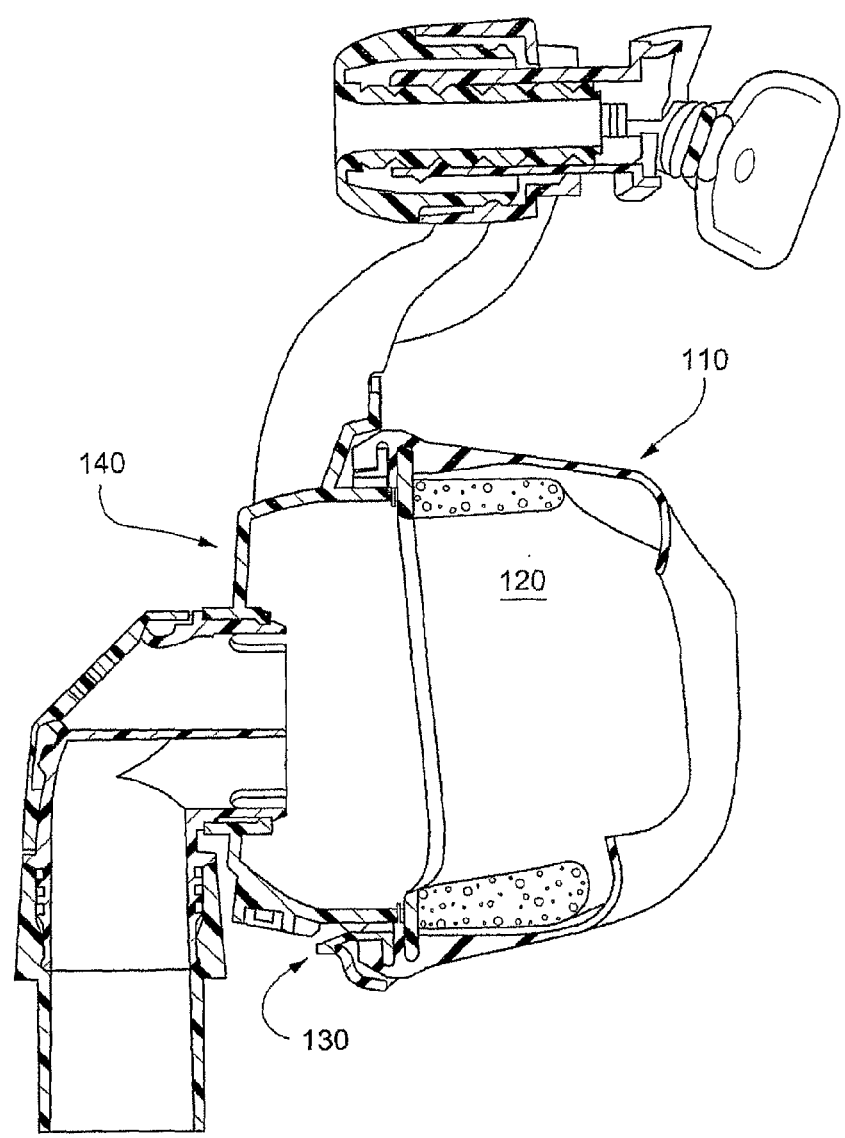
FIG. 4 shows a cross-section of a mask assembly including an undercushion and sealing membrane according to an embodiment of the present invention.

Referring to FIGS. 3 and 4, a respiratory mask assembly 80 enables a supply of breathable gas to be delivered to the airways of a patient 70. The mask assembly includes an inlet 90 and a cushion assembly 100. An example of a suitable mask is the ResMed MIRAGE MICRO nasal mask. As shown in FIG. 4, the cushion assembly 100 includes a molded membrane 110, an undercushion subassembly 120, and a clip 130. The clip 130 is structured to engage with both the cushion assembly 100 and a frame 140 of the respiratory mask assembly 80. The clip may be arranged in a similar manner to the clip used in the ResMed ACTIVA nasal mask, and as shown and described in U.S. Pat. No. 6,823,869 (e.g., see FIGS. F67 to F73(b) and columns 31-34). Unlike the ResMed ACTIVA mask, a mask in accordance with an embodiment of the present invention may include a removable undercushion sub-assembly 120. As illustrated, the undercushion subassembly 120 provides a clip that is adapted to be fit into a slot provided in the membrane, and the clip 130 is adapted to attach the cushion to the frame 140.

In embodiments, the cushion may be attached to the frame without a cushion clip. In such embodiments, the rigid clip provided to the gel bladder may replace the function of a cushion clip by providing rigidity to facilitate locating and pushing the cushion to the frame channel.

Figure 30:
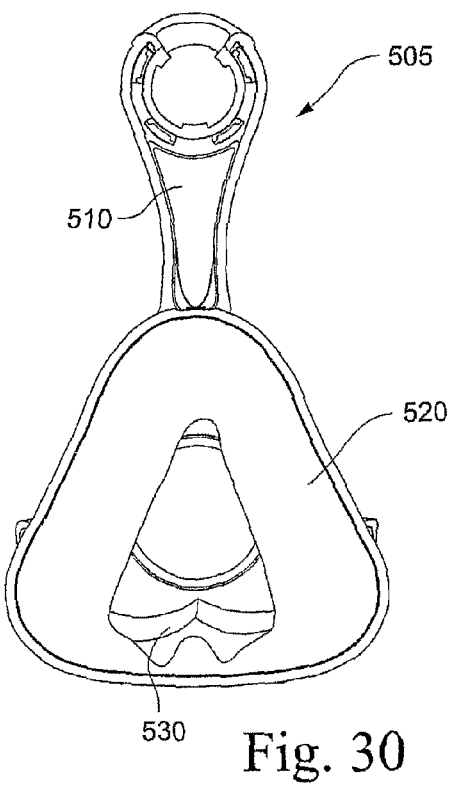
FIG. 30 shows a top view of a respiratory mask system according to an embodiment of the present invention.
Figure 31:
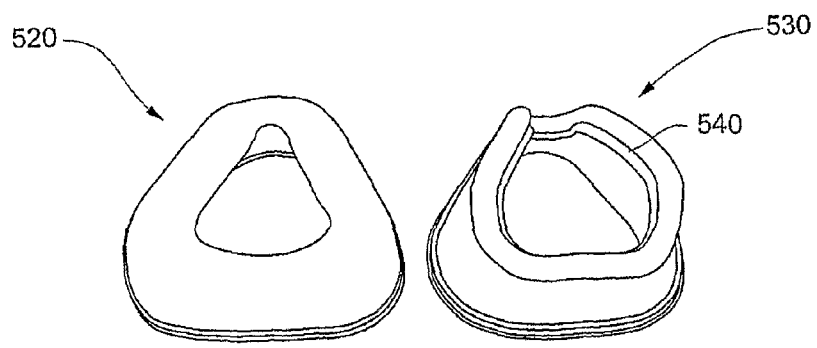
FIG. 31 shows a top view of the sealing membrane and undercushion of the mask system of FIG. 30 when disassembled.
Figure 32:
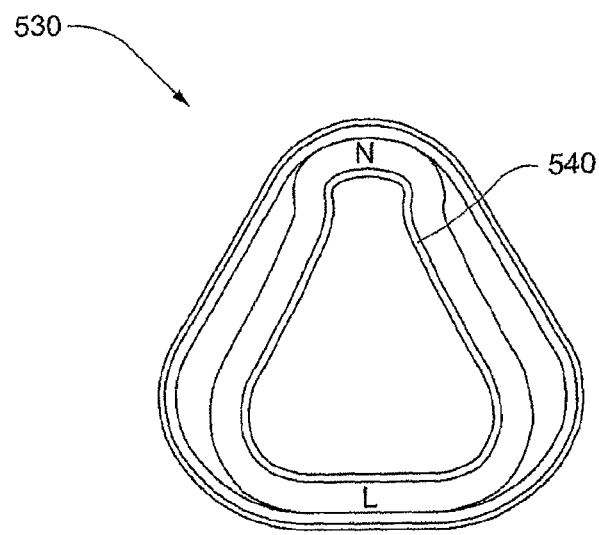
FIG. 32 shows a top view of the undercushion of the mask system of FIG. 30.
Figure 33:
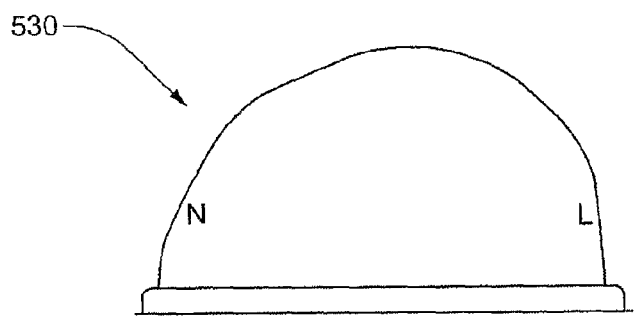
FIG. 33 shows a side view of the undercushion of the mask system of FIG. 30.
Figure 34:
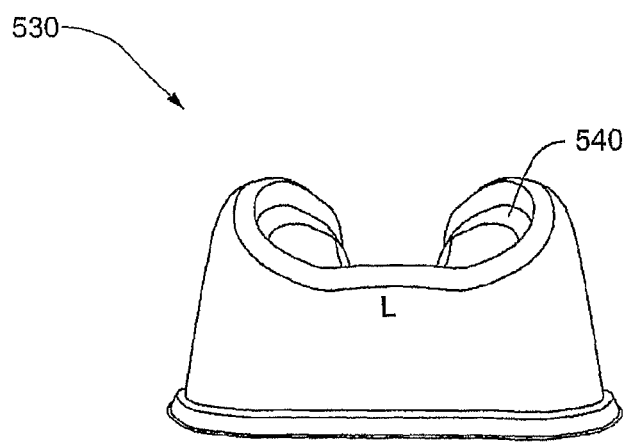
FIG. 34 shows a rear view of the undercushion of the mask system of FIG. 30.
Figure 35:
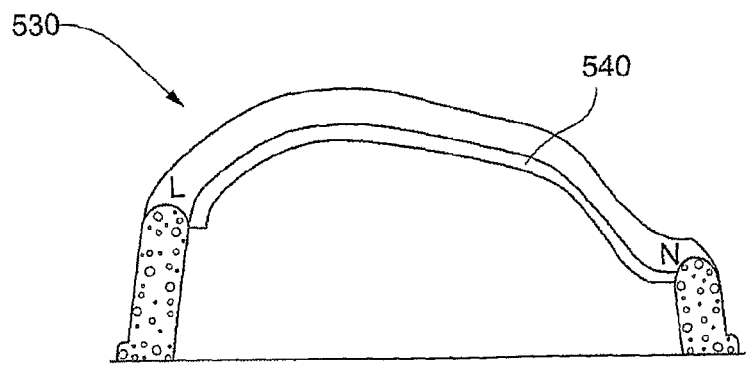
FIG. 35 shows a cross sectional view of the undercushion of the mask system of FIG. 30.

FIG. 30 shows a top view of the main elements of respiratory mask system 505 assembled, i.e., frame 510, sealing membrane 520, and undercushion 530. FIG. 31 shows the sealing membrane 520 and the undercushion 530 disassembled. FIGS. 32-35 show alternative views of the undercushion, wherein "N" indicates the nasal bridge end of the cushion and the "L" indicates the top lip end of the cushion. The number of undercushions 530 used can also be varied, for example 2 or more. Some or all of these undercushions 530 can contain the above stated gel or any other material such as foam or gas.

FIG. 16 also shows a gel 340 with a hard insert 350 adapted to support the gel within the cushion.

"Stackable"

FIG. 42 illustrates a stackable cushion arrangement in which the cushion includes a clip 780 (e.g., polyurethane clip), a membrane 710 (e.g., LSR membrane) provided to the clip 780, and a gel bladder 740 (e.g., polyurethane gel with polyurethane skin) supported by the clip 780. The clip 780 may be used to secure the cushion to an existing frame 790 (e.g., ResMed's Quattro frame). In an embodiment, the polyurethane clip may be foamed to reduce weight of parts. The gel bladder may be permanently joined to the clip (e.g., by glue) or the gel bladder may be joined to the clip by insert molding (e.g., form polyurethane clip in one half of tool, form bladder and fill with gel in other half of tool, while still warm close tool and clip and bladder will chemically bond). The membrane may be slid into the clip, i.e., membrane fit into clip before clip is in the frame or after clip is in the frame (easier usability).

Figure 43:
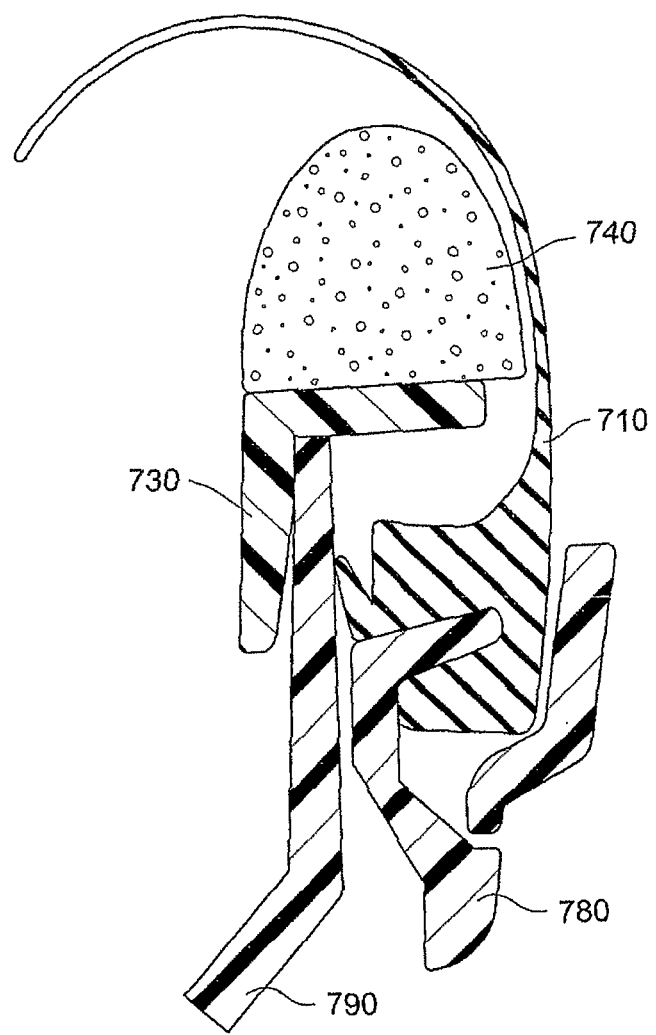
FIG. 43 is a cross-sectional view of a gel cushion according to another embodiment of the present invention.

In the stackable embodiment of FIG. 43, the cushion includes a membrane 710 (e.g., LSR membrane) and a clip 730 (e.g., polyurethane clip) that supports a gel bladder 740

(e.g., polyurethane gel with polyurethane skin). An existing cushion clip 780 (e.g., ResMed's Quattro clip) is provided to the membrane to secure the cushion to an existing frame 790 (e.g., ResMed's Quattro frame). As illustrated, the parts overlap one another for assembly.

FIG. 177 illustrates a stackable cushion arrangement in which the cushion includes a base or cushion-to-frame interface 780 (e.g., polyurethane base), a gel bladder 740 (e.g., polyurethane or silicone gel with polyurethane skin) supported by the base 780, a clip 730 (e.g., polypropylene clip) provided to one side of the base, and a membrane 710 (e.g., LSR membrane) coupled to the clip 730 and sealing engaged with the base (e.g., via sealing lip 770). The base 780 and clip 730 may be used to secure the cushion to an existing frame 790 (e.g., ResMed's Quattro frame), e.g., with a friction fit.

FIG. 178 illustrates a gel bladder 740 supported by a clip structure 780 which is adapted to engage the frame 790. The clip structure 780 locates and retains the gel bladder 740 to the cushion. The base 718 of the membrane 710 (e.g., LSR membrane) extends along one side of the clip structure 780, and the base 718 and clip structure 780 are located and retained within the frame channel of the frame 790. The contrasting materials of the clip structure and membrane (e.g., plastic and silicone) may facilitate retention and location within the frame channel.

In FIG. 179, the clip structure 780 includes a tab 780(1) adapted to engage within a corresponding recess in the membrane 710 to enhance retention/location of the membrane. In addition, a seal 771 may be provided between the clip structure 780 and frame 790 to enhance the seal between the same.

In FIG. 180, the support structure 780 includes a tab 780(1) adapted to engage within a corresponding recess in the membrane 710, and the membrane 710 and support structure 780 and retained within the frame channel of the frame 790, e.g., via a friction fit. In this embodiment, the support structure does not include a clip for interlocking with the frame. In addition, a lip seal 770 may be provided to the membrane to enhance the seal with the frame channel.

FIG. 181 is similar to FIG. 179. In contrast, the shelf of the clip structure 780 supporting the gel bladder 740 is shorter, which allows the gel bladder to engage and form a seal with the outer wall 792 of the frame channel.

Figure 182:
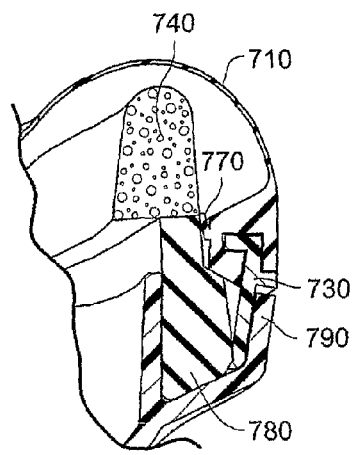

In the stackable embodiment of FIG. 182, the cushion includes a membrane 710 (e.g., silicone membrane), a clip 730 (e.g., Pocan®) including one end interlocked with the membrane 710, and a base 780 (e.g., polyurethane or silicone clip) that supports a gel bladder 740 (e.g., polyurethane gel with polyurethane skin). As illustrated, the base 780 and clip 730 engage and overlap one another for assembly to the frame channel of the frame 790, e.g., with a friction fit. The membrane 710 may include a sealing lip 770 for sealing against the base 780. In an embodiment, the gel bladder may be joined to the clip by insert molding, and the clip may be injection molded and then interlocked with the membrane.

Figure 183:
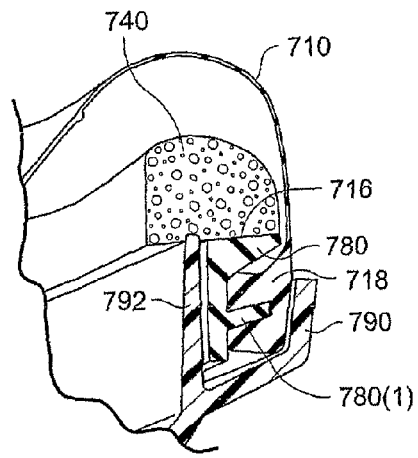

In the stackable embodiment of FIG. 183, the cushion includes a membrane 710 (e.g., silicone membrane) and a clip 780 (e.g., Pocan®) that supports a gel bladder 740 (e.g., polyurethane gel with polyurethane skin). The clip 780 includes a tab 780(1) adapted to interlock with a corresponding recess provided to the base 718 of the membrane 710. The interlocked clip/membrane is then assembled to the frame channel of the frame 790, e.g., with a friction fit. As illustrated, the shelf 716 of the clip supporting the gel bladder does not extend along the entire length of the gel bladder, which allows the gel bladder to engage and form a seal with the outer wall 792 of the frame channel. In an embodiment, the clip may be injection molded and then attached to the gel bladder, e.g., by glue.

Figure 184:
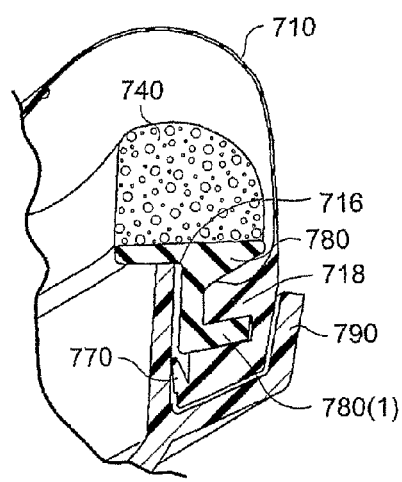

In the stackable embodiment of FIG. 184, the cushion includes a membrane 710 (e.g., silicone membrane) and a clip 780 (e.g., Pocan®) that supports a gel bladder 740 (e.g., polyurethane gel with polyurethane skin). The clip 780 includes a tab 780(1) adapted to interlock with a corresponding recess provided to the base 718 of the membrane. The interlocked clip/membrane is then assembled to the frame channel of the frame 790, e.g., with a friction fit. In this embodiment, the shelf 716 of the clip supporting the gel bladder extends along the entire length of the gel bladder. The base of the membrane may include a sealing lip 770 for sealing against the frame channel. In an embodiment, the clip may be injection molded and then attached to the gel bladder, e.g., by glue.

Figure 185:
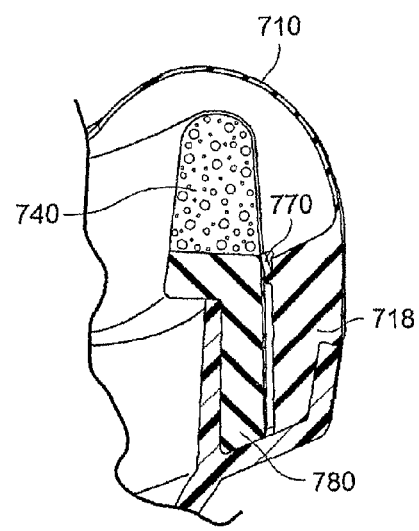

In the stackable embodiment of FIG. 185, the cushion includes a membrane 710 (e.g., silicone membrane of about 40 duro) and a clip 780 (e.g., silicone clip of about 70 duro) that supports a gel bladder 740 (e.g., polyurethane gel with polyurethane skin). The base 718 of the membrane extends along one side of the clip 780, and the base 718 and clip 780 are assembled to the frame channel, e.g., with a friction fit. The base of the membrane may include a sealing lip 770 for sealing against the clip 780.

Figure 186:
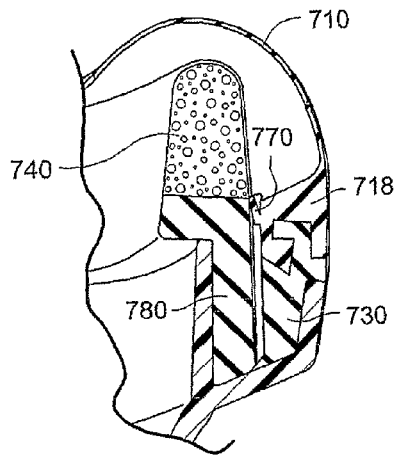

In the stackable embodiment of FIG. 186, the cushion includes a membrane 710 (e.g., silicone membrane of about 40 duro), a clip 730 (e.g., Pocan®) including one end interlocked with the membrane 710, and a base 780 (e.g., silicone clip of about 70 duro) that supports a gel bladder 740 (e.g., polyurethane gel with polyurethane skin). The base 718 of the membrane 710 and the clip 730 extend along one side of the base 780, and the assembly is assembled to the frame channel, e.g., with a friction fit. The base 718 of the membrane may include a sealing lip 770 for sealing against the base 780.

In an alternative embodiment, as shown in FIG. 187, the gel bladder 740 may be a polyurethane or silicone gel with an LSR layer (e.g., 40 duro) and the base or clip 780 may be constructed of 70-80 duro silicone. In such embodiment, the membrane (not shown) may have a configuration such as that shown in FIG. 177 or 178, for example.

FIGS. 188 and 189 illustrate alternative embodiments for attaching the gel bladder 740 to the base or clip 780 of FIG. 187. In FIG. 188, the LSR-layered gel bladder 740 may be glued to the silicone clip 780 with an adhesive 795. In FIG. 189, the polyurethane or silicone gel 741 is provided to the LSR layer 745, and then the silicone clip 780 is inserted into the LSR layer 745 to form a bond with the polyurethane or silicone gel 741 when cast.

FIGS. 65 and 66 illustrate a cushion with a gel first portion 2240 (frame contacting portion) and a silicone second portion 2210 that forms a sealing membrane. This arrangement provides a slimmer design as the components are stacked vertically instead of aligned horizontally, i.e., top cushion portion stacked on bottom cushion portion. The cushion may be provided to frame 2290.

2.1.2.1.2.2 Single Component (Gel-Filled LSR)

FIG. 40 illustrates a cushion including a membrane 710 (e.g., LSR membrane) and gel bladder 740 (e.g., polyurethane or silicone gel) molded as a one piece component. An existing cushion clip 780 (e.g., ResMed's Quattro clip) may be used to secure the cushion to an existing frame 790 (e.g., ResMed's Quattro frame). In an embodiment, the gel may be injected into the LSR membrane while it is still in the LSR molding tool. This arrangement provides a small number of mask parts.

A method of moulding a gel cushion is described in pending European Patent application EP 08160921.6 filed 22 Jul. 2008, the contents of which are hereby incorporated by cross-reference.

FIGS. 70, 96, 142-148, and 190 to 204 also show gel-filled LSR cushions.

Figure 195:
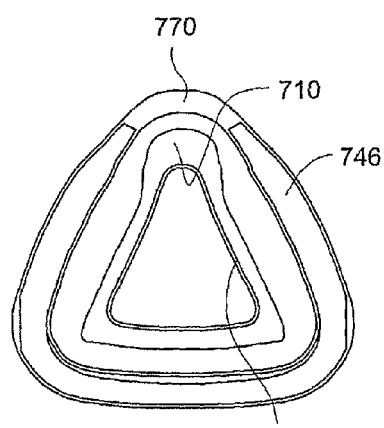
Figure 196:
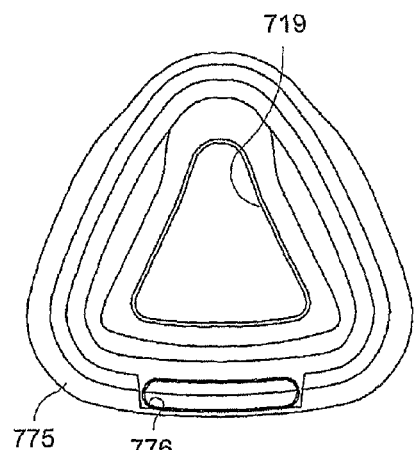
Figure 197:
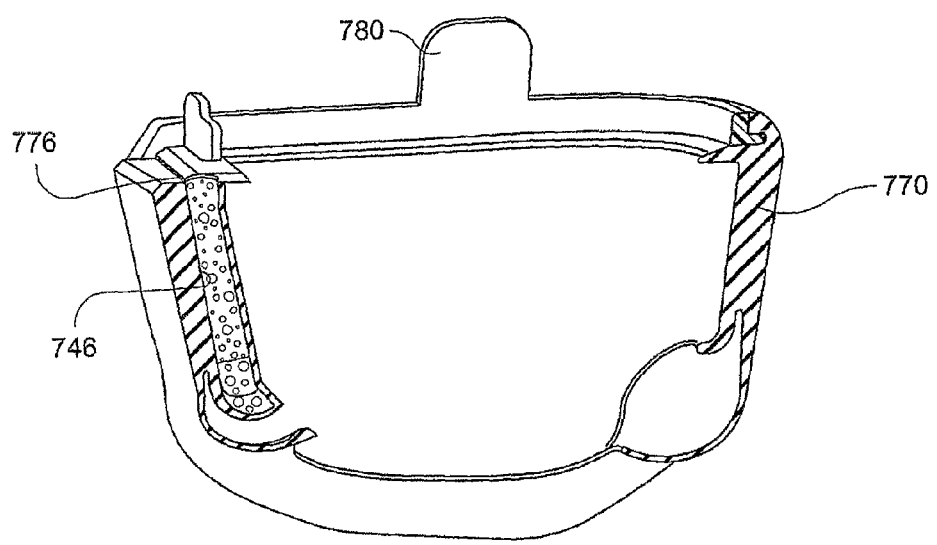
Figure 199:
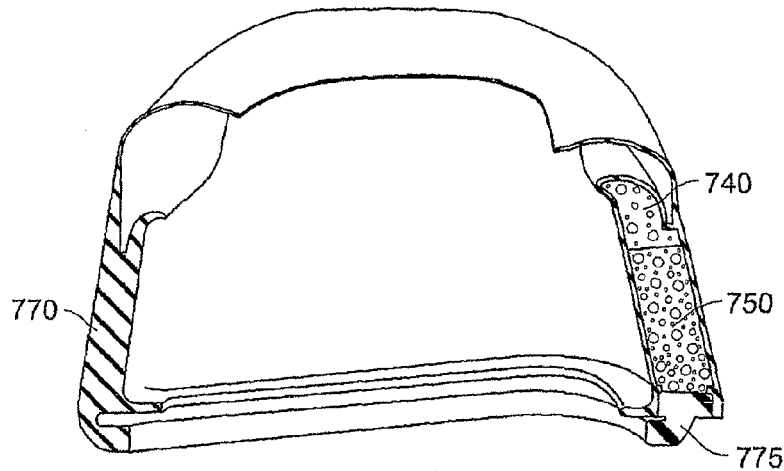
Figure 200:
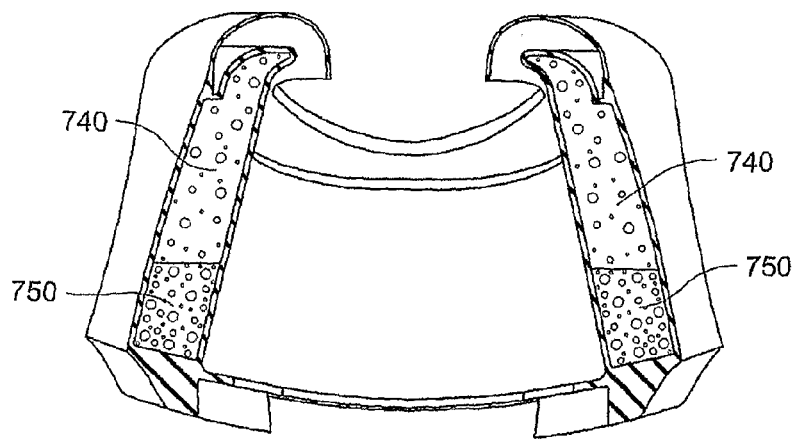

As best shown in FIGS. 197, 199, and 200, a cap 775 may be provided to the base of the cavity to enclose and retain the gels 740, 750 within the bladder or cavity (e.g., cap overmolded with the LSR cushion). A gate or hole 776 is provided in the cap 775 to allow injection of the gels into the bladder 746 (e.g., see FIGS. 193, 194, and 196). For example, FIG. 195 shows the cushion without the cap, and FIG. 196 shows the cushion with the cap.

In an embodiment, a first gel 740 may be injected through the gate 776 and then cured, and following curing of the first gel, a second gel 750 may be injected through the gate 776 and then cured. Once both gels are cured, the silicone used to make the bladder may be injected over the gate 776 to seal the cushion.

The cap 775 provides a channel 777 around its perimeter that is structured to receive a cushion clip for attaching the cushion to the mask frame. When the cushion clip is assembled to the cushion, the cushion clip 780 is structured to cover the gate 776 (e.g., see FIG. 197), therefore making it more aesthetically pleasing.

In an embodiment, some or all the cushion may be frosted to facilitate manufacture. Also, engraving may be provided to one or more sides of the cushion for branding, etc.

In the illustrated embodiment, the aperture 719 (e.g., see FIGS. 191, 192, 195, and 196) adapted to receive the patient's nose (or the patient' nose and mouth in an alternative embodiment) may be formed during the molding process, i.e., cushion has a molded aperture so that a secondary punching process is not required to form the aperture. This arrangement allows the membrane 710 to curve more inwardly (i.e., curve more inwardly towards the breathing cavity and away from the patient's face), thus effecting a better seal as the membrane can inflate more in use. In addition, a molded aperture provides a cleaner finish on the edges of the membrane.

FIGS. 202 to 204 illustrate the cushion 700 provided to a mask 789 according to an embodiment of the present invention. As illustrated, the mask 789 includes a frame 790, an elbow assembly 791 provided to the frame and adapted to be connected to an air delivery tube that delivers breathable gas to the patient, and a forehead support 793 to provide a support and stability mechanism between the mask and the patient's forehead. Headgear may be removably attached to the frame (e.g., via a headgear clip arrangement) and the forehead support to maintain the mask in a desired adjusted position on the patient's face. As noted above, the cushion is provided with a cushion clip 780 for attaching the cushion to the frame 790, e.g., with a snap-fit.

2.2 Gel

The chamber may be filled with one or more filling materials or layers or discrete portions of filling materials, e.g., one or more gels or layers of gel having different properties. For example, the chamber may be filled with two layers of gel or the chamber may be filled with more than two layers, e.g., 3 layers, 4 layers, 5 layers or more. The layers may be stacked in the axial sense (e.g., see FIG. 1*d*) and/or the layers may be arranged in other suitable manners, e.g., layers or pie-shaped sections around the cushion perimeter, layers extending parallel or perpendicular to the chamber axis, etc.

The gel may provide a comfortable cushioning structure, and may provide an appealing tactility to the cushioning structure.

The chamber may be filled with a gel prior to the inclusion of support structure, while the chamber is open (e.g., open pour or gravity fill).

The uncured gel may be placed in the chamber in a generally liquid form and fill the lower points of the chamber. The first uncured gel to be poured into the chamber may be a softer gel. In this way, in use the softer gel may be adjacent the patient's face. The second uncured gel to be poured into the chamber may be a harder gel. In another form, partially, or fully cured gels may be poured, injected, or otherwise inserted into the chamber.

In one process, a core, wall or gate may be inserted into the chamber prior filling with a first gel to prevent flow of the liquid gel into different regions of the chamber prior to curing. Once the first gel has cured, or substantially cured, the core, wall or gate may be removed and a second gel poured into the gel. In this way, a range of different cross-sections of gel may be built into a cushion wall. Furthermore, by rotating the chamber to different angles prior to, during or after curing, the different layers of gel may have different heights or thicknesses in different regions. For example, in a top lip region of a nasal cushion, a harder gel may have a relatively larger height than a softer gel. In a cheek portion, there may be a relatively larger height of soft gel material than a harder gel material. In an alternative form the two different gel materials may have equal heights in certain or all regions. A rotation process may also be used to reduce or eliminate air bubbles from a gel prior to curing, or may be used to ensure bubbles remain if desired.

In one process, the transition region or surface between different gel layers may be perpendicular to the walls of the gel-receiving chamber (e.g., see FIG. 1*d*), or aligned at an angle to the walls of the gel-receiving chamber that differs from the perpendicular (e.g., see FIGS. 212-214). Where not perpendicular (e.g., sloped), the transition region between different gel layers may exhibit a more gradual change in properties between the different gel layers that may lead to improved comfort or tactile appeal. As shown in the gel-filled LSR cushion of FIGS. 212-214, the transition region TR between first and second gels 740, 750 is generally perpendicular to the chamber walls in the upper lip region (see FIG. 214) and is sloped along its length in the cheek region (see FIGS. 212 and 213). Similar to the cushion shown in FIGS. 191 to 204 described in greater detail below, a solid silicone portion 770 is provided in the nasal bridge region. In an embodiment, the bladder may be filled with a first uncured gel layer (e.g., using gravity) to provide a sloped surface or transition region, the first gel layer is allowed to cure before the bladder is filled with the second layer.

In spite of the potential manufacturing challenges in moulding and demoulding, and the potential for silicone gel to bleed through a silicone skin, a patient interface including a cushioning structure moulded from silicone and including a pocket filled with one or more gels (e.g. silicone gels), and an integrated sealing membrane or flap in accordance with the present technology has a number of advantages vis-a-vis the prior art. For example one or more of the following advantages may be provided:

(i) a moulded silicone structure can have greater depth than can be readily manufactured from a polyurethane bladder, providing more flexibility in design or greater opportunity to improve the fit range;

(ii) a silicone sealed structure in accordance with the present technology may be multi-patient, multi-use since the gel may be fully encapsulated. This may contrast with prior gel cushion structures that do not fully encapsulate the gel, potentially exposing gel to a patient;

(iii) A silicone moulded structure enables gel to be in certain parts of the mask, and not others, for example, not having gel under the nasal bridge. This may be more difficult in a polyurethane cushion;

(iv) silicone skin has a greater elongation at break than a polyurethane film.

(v) moulding techniques in accordance with the present technology allow more consistent wall thickness of a bladder, compared to a vacuum formed film e.g. polyurethane, leading to greater control over mechanical properties;

(vi) Polyurethane doesn't handle higher temperatures as well as silicone, hence silicone is easier to clean.

(vii) A moulded structure in accordance with the present technology can be moulded with inwardly curving walls, compared to straight walls that may be required in certain prior structures. The inwardly curving wall structures may bend more comfortably and consistently, as described above. Alternatively the cushion walls may have a varied or tailored thickness in different regions, also allowing fine-tuning of comfort and effectiveness;

(viii) Polyurethane bladders may require welding that will leave a flash line. Such a flash line can impinge on the patient's nose leading to discomfort. A moulded silicone structure may not have such flashing;

(ix) A dual durometer structure may be easier to optimise for comfort and seal;

(x) According to the present technology the seal and cushion may be formed in one piece, even though they may be separate portions of a unitary structure, in contrast with a design that requires separate components for cushion and seal. Furthermore, a cushion to frame mechanism may be moulded into the single piece (e.g. as described in WO 2003/090827, the contents of which are hereby expressly incorporated by cross-reference), further reducing the overall mask component count and reducing cost of manufacture and assembly;

(xi) Furthermore, a polyurethane gel, unlike a silicone gel, may discolour with time and may have undesirable odors.

2.2.1 Single Gel

FIG. 1*e* shows an arrangement where the bladder or cavity 15 is entirely filled with a single gel material (e.g., either one of first or second gel materials 40, 50).

FIGS. 4, 24, 25, 29, 35, 40-43 also illustrate bladders with a single gel material, for example.

2.2.1.1 Exemplary Gel Hardnesses

The hardness of the gel may be selected to improve comfort and/or sealing ability for example. It should be appreciated that in each exemplary hardness range described below, the gel may include each point within the range.

In an embodiment, the bladder may be filled with a gel having a Shore 000 hardness in the range of about 10 to about 20 (and each point in between, e.g., 11, 12, 13, 14, 15, etc.), and an over-cushion or sealing membrane may be constructed from a thin membrane flap having a Shore A hardness in the range of about 20 to about 60 (and each point in between).

In another form, the gel has a Shore 000 hardness of between about 11 and about 19, e.g., between 12 and 18, between 13 and 17, between 14 and 16, about 15.

In another form, the gel has a Shore 000 hardness of between about 10 and about 15, e.g., between about 11 and about 14, between about 12 and about 13.

In another form, the gel has a Shore 000 hardness of between about 15 and about 20, e.g., between about 16 and about 19, between about 17 and about 18.

In another form, the gel has a Shore 000 hardness in the range of about 45 to about 90, e.g., between about 50 and about 90, between about 60 and about 90, between about 70 and about 90, between about 80 and about 90, between about 45 and about 80, between about 45 and about 70, between about 45 and about 60, between about 45 and about 50.

In another form, the gel has a Shore 000 hardness of between about 50 and about 80, e.g., between about 60 and about 80, between about 60 and about 70, between about 50 and about 70. A gel with such durometers are beneficial in a facemask because they are sufficiently soft for comfort, and yet having sufficient hardness for a supporting structure, thereby increasing comfort and sealing ability.

In an alternative embodiment, the undercushion includes a bladder filled with any material (e.g., foam, silicone, or oil) or any combination of materials (including gel) having a Shore 000 hardness of between 10 and 20. In yet another alternative embodiment, the undercushion includes a bladder filled with any material (e.g., foam, silicone, or oil) or any combination of materials (including gel) having a Shore 000 hardness of between 45 and 90.

In another embodiment (e.g., as shown in FIGS. 24-29), the durometer of the silicone in undercushion 420 may be below about 10 Shore A, e.g., between 1 and 5 Shore A or about 3, 4, or 5 Shore A. In another embodiment, the durometer of the silicone is above about 10 Shore A.

In another form, the gel has a Shore 00 hardness equal to or greater than about 20, e.g., 20-30 or any value inbetween, i.e., 21, 22, 23, 24, 25, 26, 27, 28, 29.

In another form, the gel has a Shore 00 hardness less than or equal to about 5, e.g., 5, 4, 3, 2, 1.

In another form, the gel has a cone penetration hardness less than about 5 cone penetrations.

In another form, the gel has a cone penetration hardness greater than about 200 cone penetrations, e.g., 200-400, 200-250.

In another form, the gel has a cone penetration hardness between about 5 and about 200 cone penetrations, alternatively between s150-200, 160-180, 200-400, 200-250.

2.2.2 Two or More Gels

Different regions of the cushion may be filled, or partially filled, with different forms of gel. For example, the nasal bridge region, cheek region and top lip region may be filled with different hardness gels.

For example, the first layer injected may be very soft or squishy to provide a comfort or soft layer, and the second layer may be harder to provide a structure or support layer. The different types of gels for the first and second layers may be defined using different properties, e.g., hardness (e.g., Shore hardness, cone penetration hardness), visco-elastic properties (e.g., time-dependent shear), resiliency, etc. In an embodiment, the gels may have one or more properties that are similar while other properties vary, e.g., similar hardnesses and different viscosities.

In one form where two or more filling materials are used, the two filling materials are chosen to have contrasting properties, e.g. a combination of a harder gel and a softer gel. The cushioning effect of the cushion structure may be adjusted by varying the relative heights or volumes of the softer and harder gels, and alternatively or additionally by adjusting the relative locations of the two or more materials. Furthermore the thickness of the chamber wall, and or hardness of the material form which the chamber is moulded may also be adjusted in different regions. For example, an inner wall of the cushion may have a thickness of about 0.2 mm to about 0.6 mm, preferably about 0.3 mm to about 0.5 mm, more preferably about 0.4 min. An outer wall of the chamber may have a thickness of about 0.3 mm to about 1 mm, preferably about 0.4 mm to about 0.8 mm, more preferably about 0.6 mm. Furthermore, a top portion of a chamber wall, located between an inner and outer walls, and in use adjacent the patient's face, may have a thickness in the range of about 0.1 mm to about 0.8 mm, preferably about 0.3 mm to about 0.6 mm, more preferably about 0.4 mm. In one form the inner and outer walls have a thickness of about 0.5 mm.

In an embodiment, the first, softer gel closest to the skin may have a compliance similar to one or more of a soft cheese, e.g. a blue vein cheese (e.g., brie, Roquefort), a soft ripe, warm Camembert, gelatin (jello), raw salmon, rare steak, sashimi, velveeta cheese, or other composites having a similar or comparable compliance. In an embodiment, the second, harder gel may have a compliance similar to one or more of a harder cheese, e.g. mozzarella cheese, hard cheddar cheese, gummy bears, boiled egg, a medium to well done steak, or other composites having a similar or comparable compliance.

In one form filling materials, e.g. gel materials, may be chosen in pairs having contrasting hardness or compliance properties such as those of hard cheese/soft cheese; well-done steak/rare steak; hard-boiled egg/soft-boiled egg; cooked salmon/raw salmon; concentrated gelatin/dilute gelatin. In this form of the technology, the precise values of the property, such as hardness, may be less important since the combined cushioning effect may be adjusted by varying the relative amounts of the two contrasting materials, or by varying the thickness of the cushion. A gel may be combined with a foam.

For example, when a relatively less resilient filling material is used, it may be appropriate to increase the thickness of the chamber wall adjacent the less resilient filling material. In the forms of the technology where cushioning and sealing are performed by different structures, adjustment of cushioning may be made without adjusting sealing structure, allowing the cushioning structure and the sealing structure to be individually optimised.

In this way, the structure may form a soft comfortable cushion for a respiratory mask with the softest layer of gel closest to the skin.

For example, FIG. 1a shows a cushioning structure including first layer 10, second layer 30, and support 20. FIG. 1b shows the cushioning structure where the first 10 and second 30 layers are welded together along their edges to define a cavity 15. FIG. 1c shows the cushioning structure where the cavity 15 formed by the layers 10, 30 has been partially filled with a first gel material 40. FIG. 1d shows the cushioning structure where the cavity 15 has been filled with second gel material 50, after having been filled with first gel material 40. In subsequent stages, a support structure may be included and the chamber sealed. In alternative pathways, the process may be repeated so that third and subsequent gels may be included. In this way, a more complex cushion wall structure may be created, for example having a harder interior and a softer exterior. In an alternative process, the gel may be injected via injection points in the support structure.

Figure 2B:
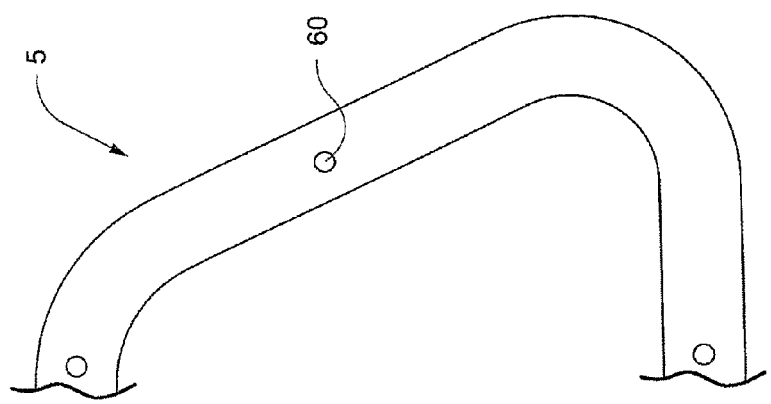
FIG. 2b shows the portion of FIG. 2b from the non-patient contacting side.
Figure 2D:
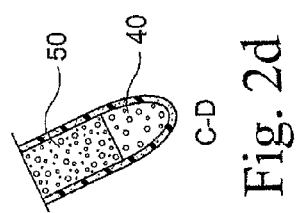
FIG. 2d shows a cross-section of the portion of the cushioning structure of FIG. 2a in the cheek contacting region.
Figure 2A:
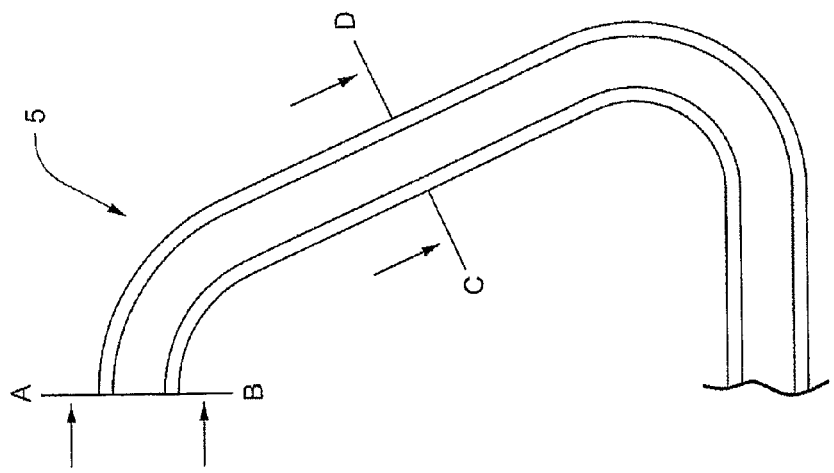
FIG. 2a shows a portion of a cushioning structure suitable for a nasal respiratory mask from the view of the patient face-contacting side according to an embodiment of the present invention.
Figure 2C:
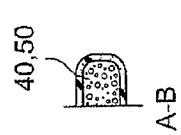
FIG. 2c shows a cross-section of the portion of the cushioning structure of FIG. 2a in the nasal bridge contacting region.

FIG. 2a shows a portion of a cushioning structure 5 suitable for a nasal respiratory mask from the view of the patient face-contacting side, and FIG. 2b shows the portion of a cushioning structure from the non-patient contacting side to illustrate injection ports 60. FIG. 2c shows the cushioning structure in the nasal bridge contacting region (e.g., the cavity is filled with only one gel material (e.g., gel materials 40 or 50)), and FIG. 2d shows the cushioning structure in the cheek contacting region (e.g., the cavity is filled with two different gel materials (e.g., gel 40 and gel 50)).

Figure 7:
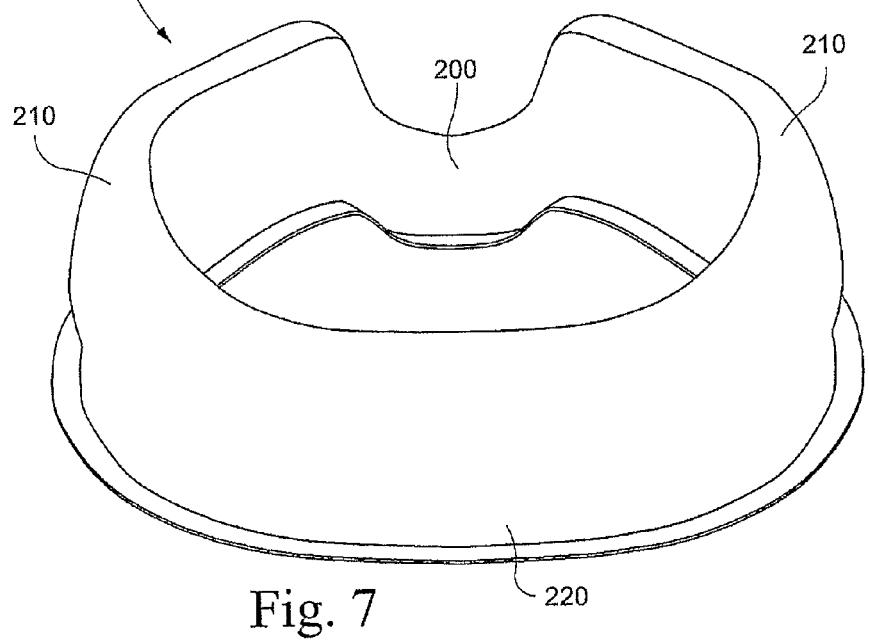
FIG. 7 shows another view of the cushion of FIG. 5.

FIGS. 5-7 show a cushion 205 incorporating dual durometer gel technology with nasal bridge region 200, cheek region 210, and top lip region 220. In this form, the cheek region 210 presents to the face a gel of a first material property value (e.g. a softer or harder gel) and the nasal bridge region 200 and top lip region 220 have a different material property value (e.g. a harder or softer gel).

FIG. 8a shows a schematic cross-section of a chamber 315, shown end-on, formed for example from a layer of polyurethane. In FIG. 8b, the core, wall or gate 325 is inserted to prevent filling of certain regions of the chamber 315 with the first gel. As illustrated, the core 325 has a tapered configuration along its length (e.g., thicker base region that tapers to a thinner region near the face contacting portion). However, it should be appreciated that the core may have other suitable configuration in order to modify the hardness or feel provided by the first and second gels. In FIG. 8c, the first gel 340 is poured into the chamber 315 and cures. In FIG. 8d, the first gel 340 has cured and the core, wall or gate 325 has been removed. In the next stage, shown in FIG. 8e, the second gel 350 is poured into the remaining space in the chamber 315 to cure.

Figure 9A:
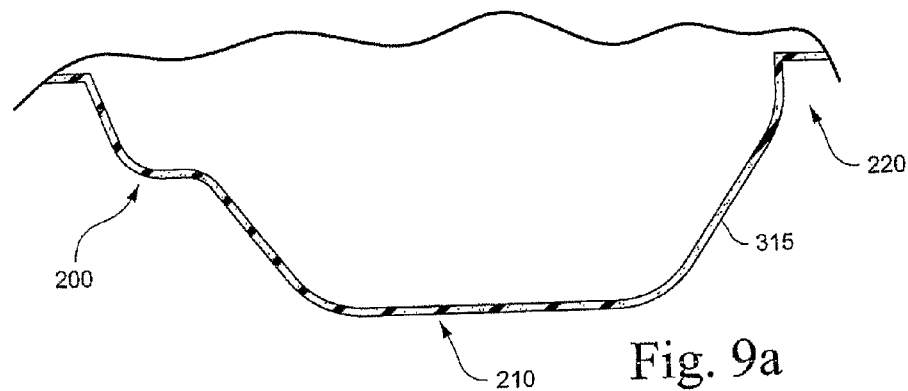
FIGS. 9a to 9c shows a process for filling a chamber with two gels according to an embodiment of the present invention.
Figure 9B:
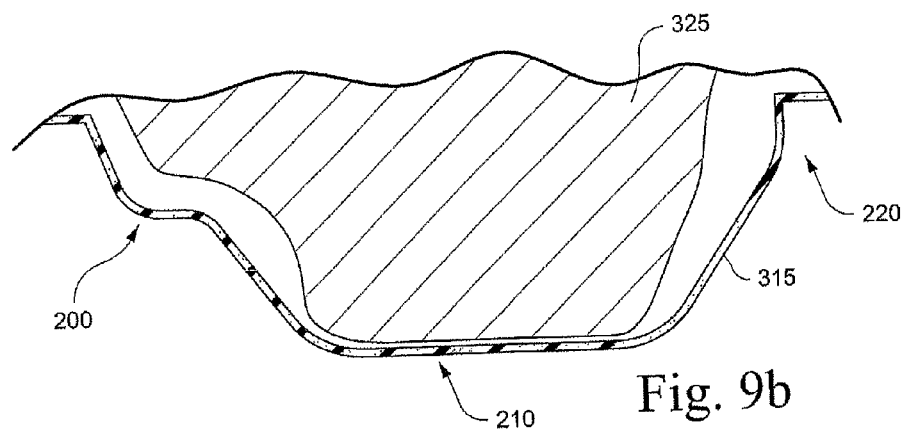
Figure 9C:
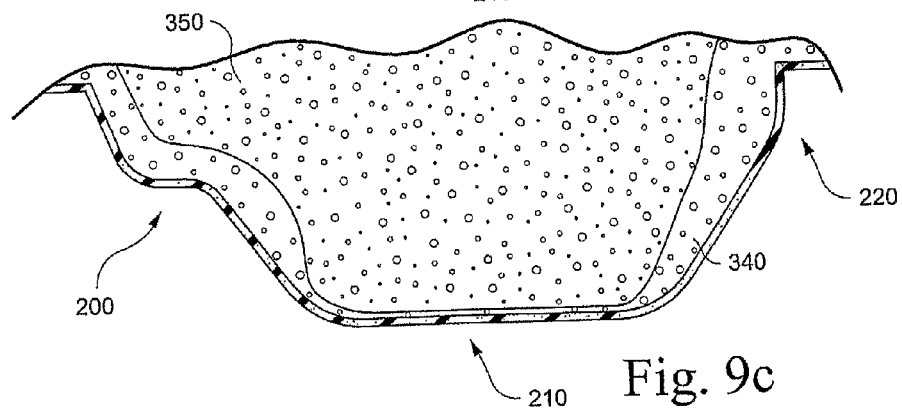

FIG. 9a to FIG. 9c show a similar process to that shown in FIGS. 8a to 8e, from a side view (similar to that shown in FIG. 6). Corresponding intermediate stages shown in FIGS. 8c and 8d are omitted. In this process, different amounts or levels of the first gel 340 may be positioned in the nasal bridge region 200, cheek region 210 and top lip region 220 to vary the softness or stability in these regions. As illustrated, the first gel 340 is relatively thinner in the cheek region 210 (compared to the nasal bridge and top lip regions 200, 220) to enhance stability and hardness in this region, whereas the first gel 340 is relatively thicker in the nasal bridge and top lip regions 200, 220 to enhance comfort and softness in these regions.

Figure 17:
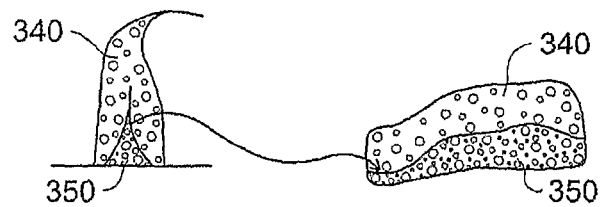
FIG. 17 shows a cross section and side view of a cushion according to another embodiment of the present invention.

FIG. 17 also demonstrates another use of the process described in FIGS. 8a to 8e. The shapes of the first and second gel portions 340, 350 may be configured to provide the most desirable comfort and stability properties to each region of the face, for example, increase comfort at the nasal bridge and increase stability at the cheeks. That is, the softer, first gel 340 has an increased height with respect to the harder, second gel 350 in the nasal bridge region, which enhances comfort and softness in this region. Likewise, the harder, second gel 350 has an increased height with respect to the softer, first gel 340 in the cheek regions, which enhances stability and hardness in this region. It should also be noted that the shapes of the first and second gel portions may not be similar and may have different curvature.

Figure 18:
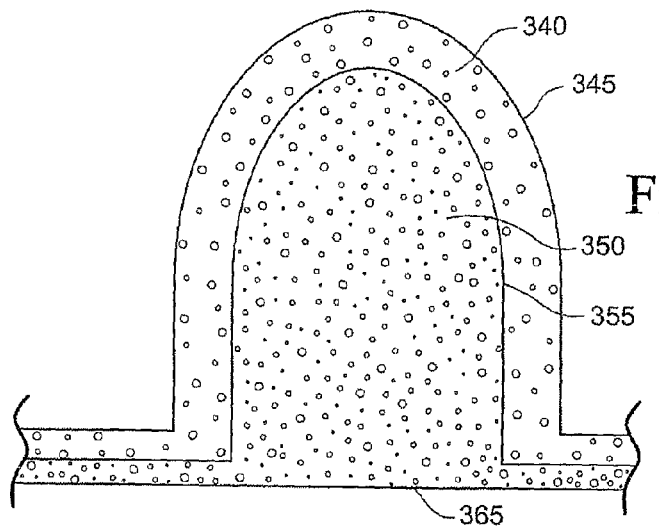
FIG. 18 shows a cross section of a cushion according to another embodiment of the present invention.

FIG. 18 follows a similar technique to that described in FIGS. 8a to 8e. Rather than fill the void left in FIG. 8d with gel (as shown in FIG. 8e), the void may be filled with another gel encased in a skin. This second gel cushion could be formed separately (demonstrated in FIGS. 1a and 1b) and positioned inside the void. FIG. 18 illustrates first gel 340 with first skin 345, second gel 350 with second skin 355, and a third skin 365 along the base. Alternatively, the second skin could be placed around the surface of the void and then filled with the second gel.

FIG. 10a and FIG. 10b show in cross-section two alternative configurations, each with two different materials, for example, two different gels 340, 350.

FIG. 11a and FIG. 11b show side views with different materials (e.g., different gels 340, 350) in different regions. For example, in FIG. 11a, there are two generally horizontal layers. In FIG. 11b, the nasal bridge region 200 and top lip region 220 are filled differently than the cheek region 210.

Figure 19A:
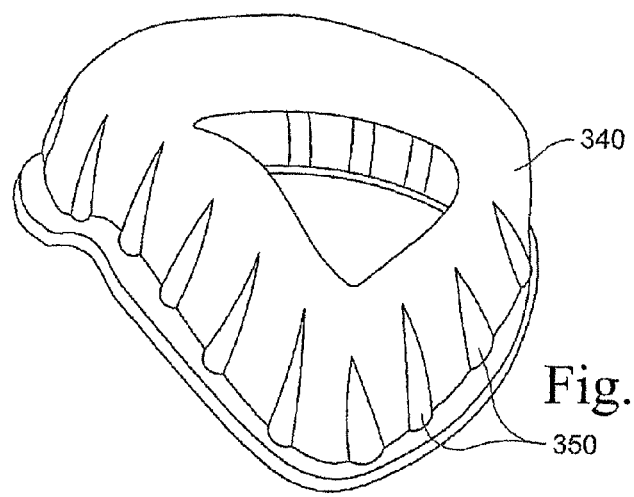
FIGS. 19a and 19b show a side view and cross section of cushion according to another embodiment of the present invention.
Figure 19B:
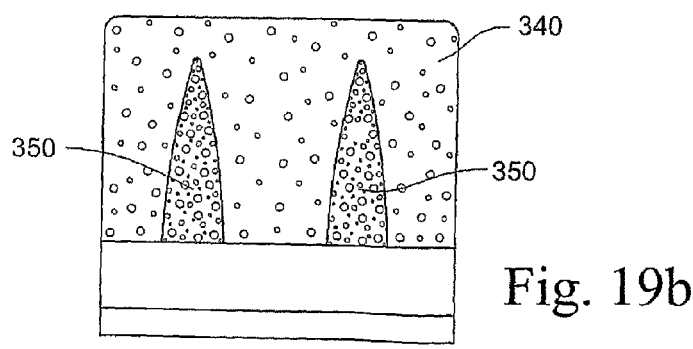

FIGS. 19a and 19b shows a cushion where higher durometer gel ribs 350 are equally placed around the cushion filled with a lower durometer gel 340 for structure. Such ribs 350 are shown towards the exterior surface of the cushion however it should be appreciated that these ribs could be placed anywhere within the cushion, e.g., depending on facial features. Additionally, the ribs could be formed separately to the cushion and retrofitted to the external surfaces of the mask. Alternatively, the ribs could be integrated with the cushion to frame mechanism, e.g., cushion clip. The ribs may also vary in geometry to better suit facial profile. For example, the ribs may have varying height and width at certain points on the face, e.g., to adjust the hardness of the cushion for different regions of the patient's face.

FIG. 20 shows another embodiment of the current invention, demonstrating a cushion with 3 layers of gel, e.g., gels 340, 350, and 360. Each layer may comprise a gel with different durometer to the other layers. Alternatively, two layers may have the same durometer and the final layer may have a higher or lower durometer. The three layer configuration may enable greater refinement of the comfort and stability of the cushion. FIG. 61 illustrates a cushion with three layers of gel, i.e., a low durometer first layer 360, a high durometer second layer 350, and a low durometer third layer 340. The low durometer first layer 360 may enable the high durometer second layer 350 to be slightly flexible so that the cushion can conform to the face. This arrangement provides a combination of support and comfort.

FIG. 22 shows another embodiment whereby there are one or more localized regions of lower durometer gel (region 1) that are positioned to provide more comfort to the patient. In the illustrated embodiment, there is softer gel at the nasal bridge and upper lip or chin regions, while the cheek region includes a higher durometer gel (region 2). These comfort regions may be formed integrally with the rest of the cushion, or could be retrofitted to the cushion. Additionally, the patient may be able to choose from a range of separate gel cushion inserts that vary in hardness, which may be retrofitted into the cushion. This enables patients to customize their mask to suit their individual needs.

In an embodiment, the cushion may include insertable or co-molded zones 2001 so that different size and/or durometer zones may be selectively positioned (e.g., see FIG. 63A). FIG. 63B illustrates a cushion with first and second zones 1, 2 with first and second durometers, and one of the first and second zones may be selectively interchanged with a third zone 3 having a third durometer. It should be appreciated that the cushion may have any suitable number of zones to allow multiple zones of different durometers.

Figure 23A:
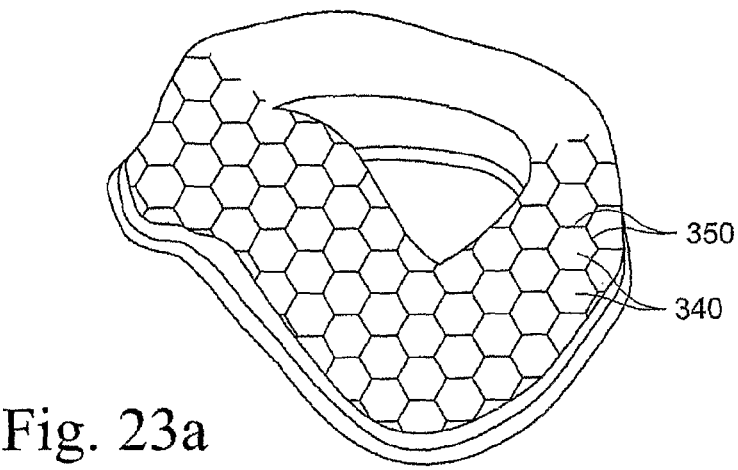
FIGS. 23a and 23b show an isometric view and enlarged isometric view of a cushion according to another embodiment of the present invention.
Figure 23B:
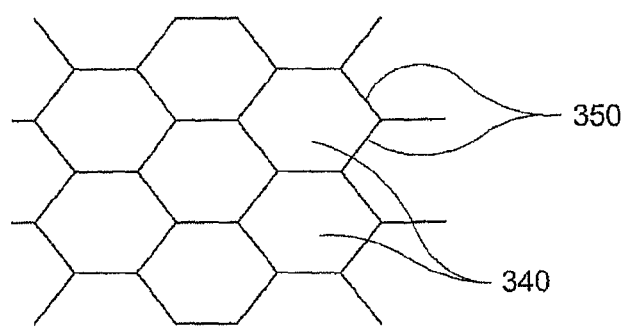
Figure 25:
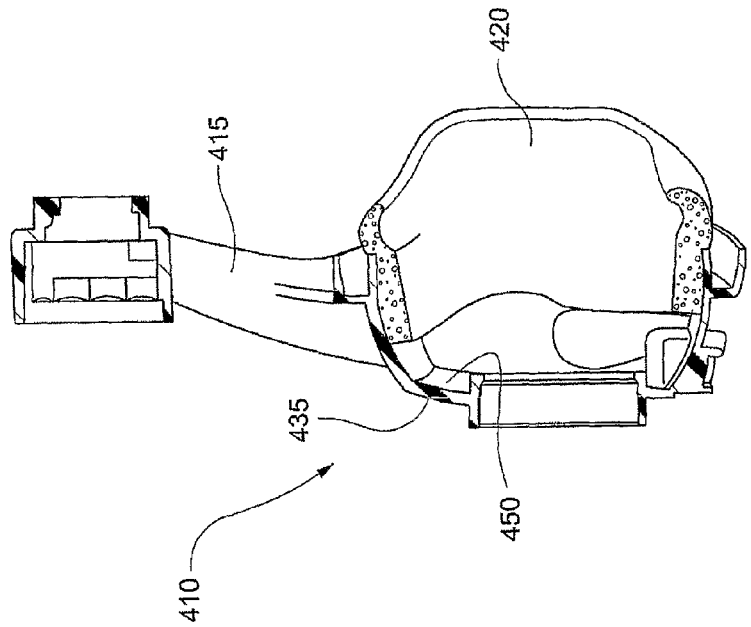
FIG. 25 is another cross-section through the mask of FIG. 24.
Figure 24:
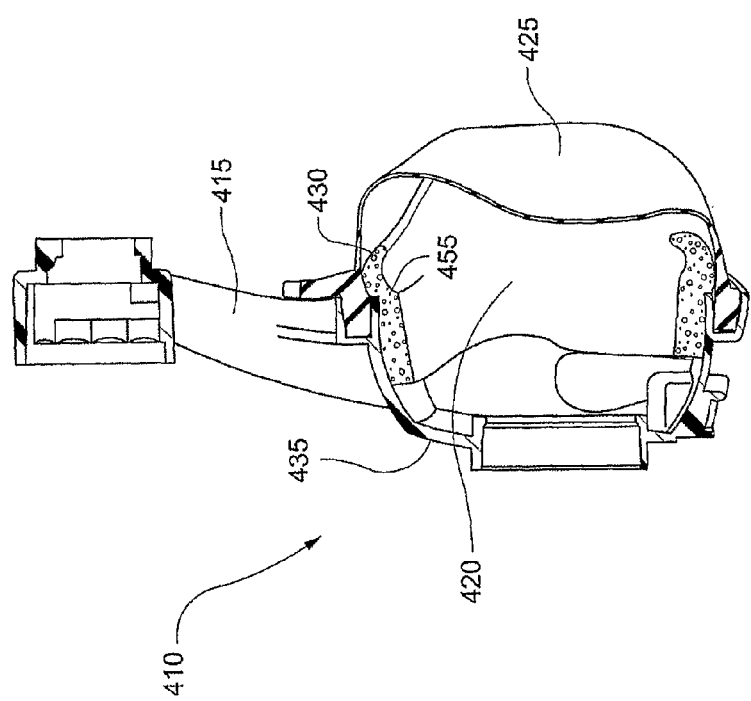
FIG. 24 is a cross-section through a respiratory mask according to an embodiment of the present invention.
Figure 26:
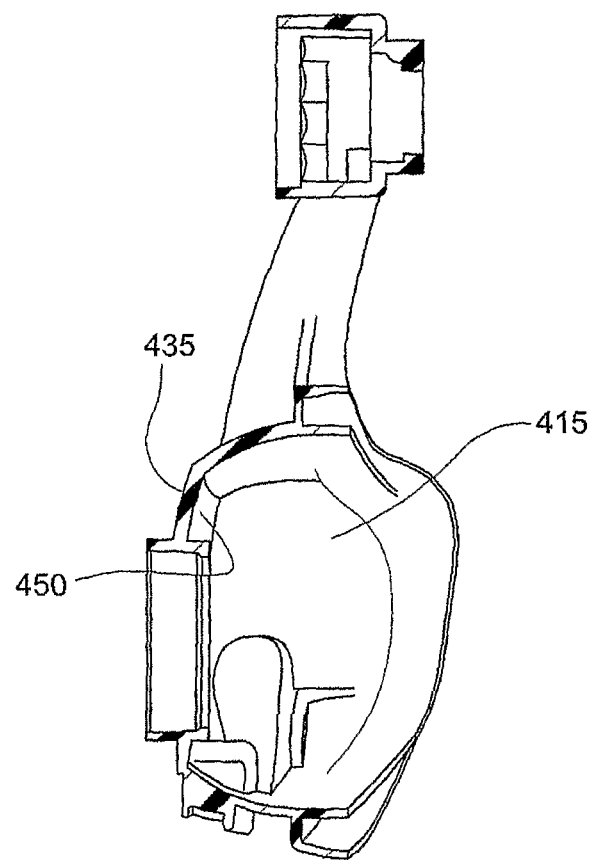
FIG. 26 is a cross-section through the frame of the mask of FIG. 24.
Figure 27:
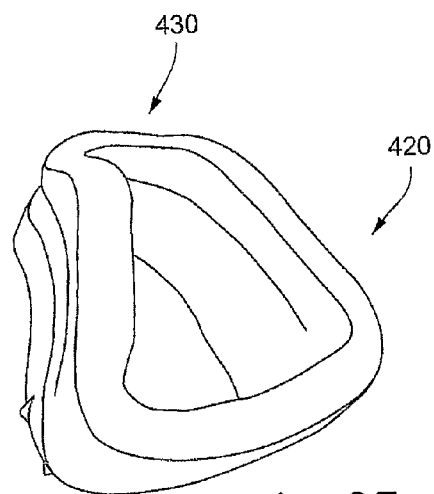
FIG. 27 is a perspective view of the undercushion of the mask of FIG. 24.
Figure 28:
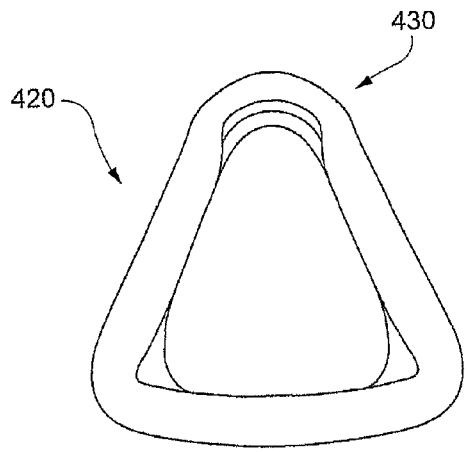
FIG. 28 is a front view of the undercushion of the mask of FIG. 24.
Figure 29:
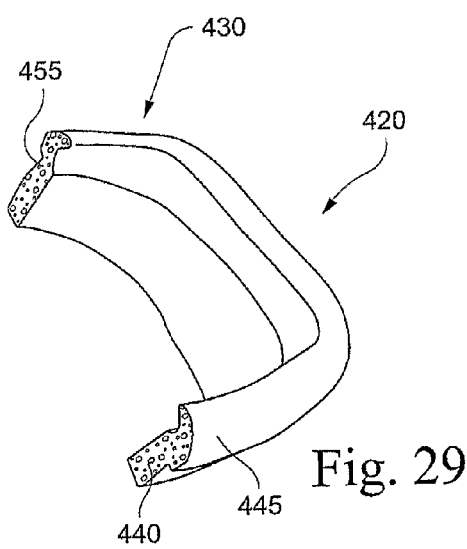
FIG. 29 is a perspective cross-section through the undercushion of the mask of FIG. 24.

FIGS. 23a and 23b shows another configuration according to an embodiment of the invention. In this embodiment, higher durometer gel 350 forms a honeycomb-like structure and lower durometer gel 340 is filled into the spaces created by the honeycomb. This arrangement provides a trampoline or suspension system to cushion the patient's face. The higher durometer structure maintains the design integrity but the lower durometer gel allows some flexibility.

Figure 59:
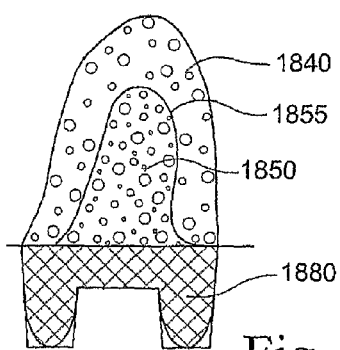
FIG. 59 illustrates a cushion with two layers of gel separated by skin according to an embodiment of the present invention.

FIG. 59 illustrates a cushion with two layers of gel 1840, 1850 separated by skin 1855, which avoids mixing of gels and thus maintains structural integrity. This arrangement may provide varying heights throughout the inner and outer gel layers to better conform to patient's face. The two layers may result in a combination of support and comfort. In an embodiment, the outer layer may be Shore 000<10-20, and the inner layer may be Shore 000>45-55. A clip 1880 (e.g., Shore A>80) may be provided to the cushion.

Figure 103:
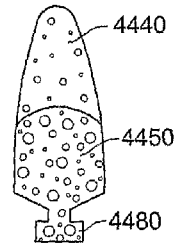
FIGS. 103 and 104 illustrate a cushion with a first layer of low durometer gel and a second layer of high durometer gel according to an embodiment of the present invention.
Figure 104:
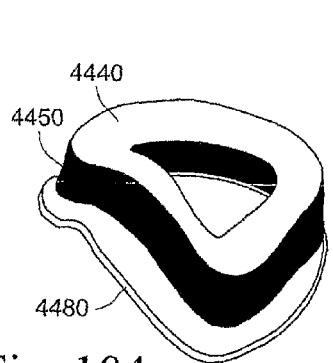

FIGS. 103 and 104 illustrate a cushion with a first layer of low durometer gel 4440 and a second layer of high durometer gel 4450, and wherein a cushion clip 4480 is integrally formed into the second layer 4450.

FIGS. 199 and 200 show a gel-filled LSR embodiment in which the bladder 746 is injected with two different gel materials (i.e., first and second gels 740, 750) to provide the cushion with different hardnesses or durometers along its height (e.g., dual durometer). The height and/or angle of each gel material may be adjusted to vary the hardness, the rigidity, or the way the cushion feels on the patient's face in use, e.g., the first gel may be relatively softer than the second gel and the relative heights of the gels or ratio of heights may be adjusted to adjust the hardness.

The dual durometer gel arrangement may be provided about the entire perimeter of the cushion, or the dual durometer gel arrangement may be provided in selected regions of the cushion. For example, in the illustrated embodiment, the dual durometer gel arrangement is not provided in the nasal bridge region of the cushion. That is, the dual durometer gel arrangement is provided in cheek and upper lip regions of the cushion and a solid silicone portion 770 is provided in the nasal bridge region of the cushion (see FIGS. 199 and 204). The solid silicone portion 770 at the nasal bridge region may facilitate manufacture.

Also, the hardness provided by the dual durometer gel arrangement may vary in different regions about the cushion perimeter. For example, as shown in FIGS. 199 and 200, the cheek regions may be relatively softer than the upper lip region due to the longer height of the softer first gel in the cheek regions. That is, the height of the softer first gel may enhance the softness and/or shock absorbing characteristic of the cushion while the height of the harder second gel may enhance the support and/or springiness of the cushion. The ratio of the heights may be tuned to vary the hardness, the rigidity, or the way the cushion feels on the patient's face in use.

In an embodiment, the first and second gels 740, 750 may be different colors (e.g., first gel is clear and the second gel is blue) for aesthetics and/or to emphasize the dual durometer gel arrangement. The bladder may be substantially transparent to allow the different colored gels 740, 750 to be visible through the bladder (e.g., see FIG. 201). In another embodiment, the same gel may be provided with different colors, e.g., for aesthetics.

2.2.2.1 Exemplary Gel Hardnesses

The hardness of each gel may be selected to improve comfort and/or sealing ability for example. It should be appreciated that in each exemplary hardness range described below, the gel may include each point within the range.

In an embodiment (e.g., as shown in FIG. 1d), the first layer 40 may have a Shore 000 hardness of less than about 10, or between about 10 and about 20, or between about 15 and about 25, or between about 20 and about 40, or between about 10 and about 15, e.g., 12, 13, or 14. The second layer 50 may have a Shore 000 hardness of about 40 to about 50, about 45 to about 55, about 50 to about 60, about 55 to about 65, about 60 to about 70, greater than 45, or in the range of about 45 to about 90. Alternatively, the second layer may have an indentation hardness more appropriately measured on the Shore 00 hardness scale, for example about 10 to about 20, or about 20 to about 30.

In another embodiment, (e.g., the gel-filled LSR embodiment of FIGS. 199 and 200), the first gel (i.e., the patient contacting gel) may be approximately 10-15 Shore 000, e.g., 13 Shore 000, and the second gel (i.e., the supporting gel) may be approximately 50-60 Shore 000, e.g., 52 Shore 000.

In another embodiment (e.g., as shown in FIGS. 12a and 12b) the gel 350 for the inner supporting layer may be about 45-90 on the Shore 000, e.g., about 45-70, about 50-70.

2.2.3 Gel Support Structures

In alternative embodiments, the cushion may be constructed using one or more layers of gel and one or more layers of another material, for example a silicone. For example, the second gel or interior structure/layer described above may be a silicone instead to support the surrounding gel.

For example, it should be noted that interior structure shown in FIGS. 12a and 12b may be made from any other reasonable material than gel, for example polycarbonate, polypropylene. In this case, the surrounding gel may be softer (for example, 0-45 on the Shore 000, e.g., 0-20 on the Shore 000, e.g., 10-20 (e.g., 15)) as there is a more rigid structure supporting its shape.

FIG. 13a and FIG. 13b show multiple internal structures. The base structure 350 may be made from silicone and include a portion 352 constructed to engage with a hard component such as a frame of a mask. In FIG. 13a, the base structure 350 includes multiple fingers 354 and a surrounding layer 340. In FIG. 13b, first and second surrounding layers 340(1), 340(2) are provided to the base structure 350.

FIG. 14 shows a structure that includes a silicone membrane component 370, an internal rib 350 that supports an exterior gel component 340, and a frame engaging portion 352. The frame engaging portion is integral with the internal rib.

FIG. 21 shows an alternative configuration whereby the inner gel or support structure 350 is configured with multiple horizontal branches in a tree-like shape. Such a configuration may enable better distribution of compressive forces. FIG. 62 illustrates a cushion with such a branched medium/high durometer insert 350 to provide a spring element as well as support.

Figure 51:
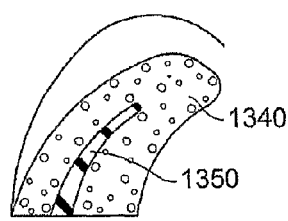
FIG. 51 illustrates a gel cushion with a firm support according to an embodiment of the present invention.

FIG. 51 illustrates a firm support 1350 in the center of a gel cushion 1340. The firm support is not constructed of a gel (e.g., PC, PP) and may be more rigid (e.g., gel surrounds firm support). This may be ideal for gels Shore 000 0-20, since shape is provided by support center, and a more comfortable soft gel can be used on outer layer. This shape may also be reasonable for gels Shore 000 20-45, which may not be as comfortable as the softer gels.

Figure 55:
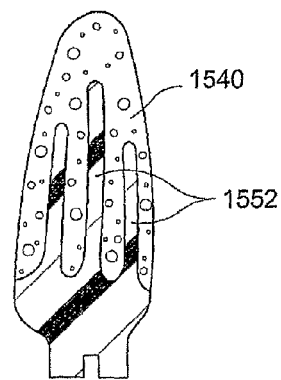

FIGS. 54 and 55 illustrate a cushion with multiple adjacent ribs 1552 (e.g., constructed of LSR) within a gel 1540 (e.g., low duro). The multiple adjacent ribs may be provided for comfort or to support a very soft gel. The multiple adjacent ribs may also provide more stability in the horizontal direction than a single rib insert.

Figure 56:
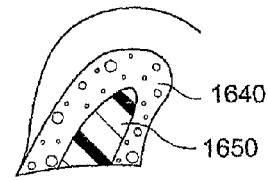
FIG. 56 illustrates a gel cushion with a firm support according to an embodiment of the present invention.

FIG. 56 illustrates a firm support 1650 in the center of a gel cushion 1640 and may be more rigid than the gel that surrounds the support. This may be ideal for gels Shore 000 0-20 (outer comfort layer) and 45-70 (inner supporting layer).

Figure 57:
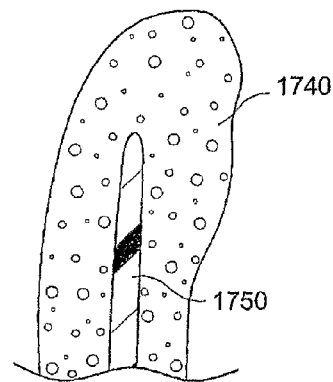
FIG. 57 illustrates gel cushion with an insert according to an embodiment of the present invention.
Figure 58:
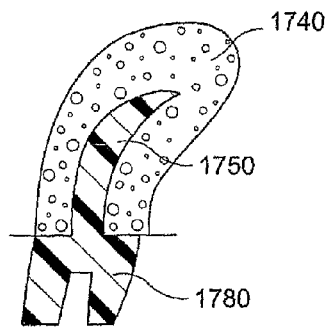
FIG. 58 illustrates gel cushion with an insert and cushion clip according to an embodiment of the present invention.

FIG. 57 illustrates an insert 1750 within a gel 1740 for stability. The gel may be relatively thick so that the patient does not feel the insert. As shown in FIG. 58, the insert 1750 may be curved to bias the cushion inwards. The insert may be solid or somewhat harder than the gel. Also, the insert 1750 may be a part of a cushion clip 1780 (e.g., see FIG. 58). In an embodiment, the insert/clip may have a Shore A hardness greater than about 80 and the gel may have a Shore 000 hardness less than about 20.

FIG. 60 illustrates a cushion with a high durometer polyurethane core 1950, skin 1945, and a low durometer gel 1940. This arrangement looks and feels like gel. For comfort, facial contact with the high durometer core should be avoided.

FIG. 64 illustrates a cushion with a cured silicone 2150 that gradually blends to an uncured silicone 2140 with a skin 2145. The uncured silicone will be more viscous so will better conform to the patient's face.

FIGS. 16 and 17 illustrate an insert 350 within gel 340 that could be shaped to suit a required stability at parts of the patient's face, i.e., insert variable around the cushion perimeter to create structure that is contoured to suit patient's face. For example, the insert 350 may be shallow at the nasal bridge to avoid discomfort and deeper at the cheek region for stability (see FIG. 17). The gel 340 could also be contoured to mirror dimensions of the insert 350 (see FIG. 16) so that the hard insert is not uncomfortable. Referring to FIG. 16, the gel 340 may be thicker along an inside portion so the patient will not feel the rib-like insert maintaining stability.

3. Manufacturing Summary for Gel Mask

The gel mask or cushion includes four general manufacturing components, i.e., forming, filling, welding, and trimming.

To form by vacuum forming/thermoforming, heat film of polymer, place over male or female mold, and suck film into shape. The male mold provides a raised (convex) mold, and the female mold provides a cut out (concave) mold.

To form by dipping, mandrel in shape of cushion is heated, mandrel dipped in resin solution then removed, cure resin on mandrel, and remove from mandrel.

To form by pressure forming, heat film of polymer, place film over mold (usually female), and apply air pressure to back of film to force film into/against mold. This forming process may provide better detail than vacuum forming because pressure forming can produce up to five times the pressure of vacuum forming.

To fill by open cast, fill gel into half of bladder and seal off with other half of bladder. This filling process can be done in the tool or nested depending on curing characteristics of the gel.

To fill by injection, inject gel into bladder once formed, and cover the injection point with glue or silicone.

Welding may include skin to skin or skin to clip.

Trimming may be automated or manually completed.

3.1 Vacuum Forming

A structure for retaining a gel in a form suitable for a respiratory mask is shown in FIGS. 1a to 1e. The structure has three components: (i) a first or top layer 10, (ii) a second layer 30, and (iii) a support 20. The first and second layers may be made from a polyurethane film or films having a thickness of about 0.07 mm to about 0.25 mm. The support structure may be made from polyurethane or polypropylene.

The top layer is vacuum formed into a shape to define a gel-receiving chamber or bladder.

In an embodiment, the top layer may be vacuum formed using a female mold as shown in FIG. 47. In this technique, a center portion of the layer is stretched as it is drawn into the female mold under vacuum. This leads to the center portion being thinner than the side portions (i.e., softer/thinner skin is at the top near the patient contacting surface).

In another embodiment, the top layer may be vacuum formed using a male mold as shown in FIG. 46. In this technique, side portions of the layer are stretched as they are drawn on the male mold under vacuum. This leads to the center portion being thicker than the side portions (i.e., harder/thicker skin is at the top near the patient contacting surface).

The support structure is placed in between the first and second layers and the first and second layers are Radio Frequency (RF) welded to join them together. RF welding uses electromagnetic energy to heat the joining surfaces of the first and second layers. Pressure is then applied to the joining surfaces by a die. The combination of heat and pressure causes the joining surfaces of the first and second layers to permanently bond.

The support structure may include a series of injection points through which one or more gels may be injected to fill the gel-receiving chamber.

In this embodiment, the top layer or skin defining the gel bladder or gel cavity may be formed using one skin or two or more skins (e.g., joined by RF welding).

3.1.1 "1 Skin"

FIGS. 205 and 206 illustrate "1 skin" embodiments. In these embodiments, a one-piece skin 7310 is formed (e.g., vacuum formed or drawn), the gel 7340 is injected and cured, a backing 7330 with or without a cushion clip 7320 is formed and then the backing 7330 is located and welded to the outer skin 7310, and then a trimming operation may be performed to remove any excess skin/backing.

As illustrated, the top layer provides end portions 7315 (e.g., L-shaped parts) that provide a relatively flat surface for engaging and supporting the backing 7330.

3.1.2 "2 Skin"

FIGS. 207 and 208 illustrate "2 skin" embodiments. In these embodiments, the top layer includes inner and outer skins 7310, 7311 that are formed (e.g., vacuum formed or drawn), the inner and outer skins 7310, 7311 are registered and located with respect to one another and then welded to one another, a backing 7330 with or without a cushion clip 7320 is a formed and then the backing 7330 is located and welded to the inner and outer skins 7310, 7311, the gel 7340 is injected and cured, and then a trimming operation may be performed to remove any excess skin/backing.

As illustrated, the top layer provides end portions 7315 (e.g., L-shaped parts) that provide a relatively flat surface for engaging and supporting the backing 7330.

3.2 Injection Molding

Another structure for retaining a gel may be created by molding a component in liquid silicone rubber (gel-filled LSR).

Materials and manufacturing processes are considered when designing a gel-filled LSR cushion. For example, the following manufacturing aspects are considered: hardness of the one or more gel materials (e.g., suitable 000 Shore hardness of gel); gel compatibility with the LSR layer (e.g., suitable gel and LSR layer structure to prevent bleeding of the gel through the LSR layer); in-mold or out-of-mold filling of gel; suitable gel cure temperature; suitable gel cure time; mix ratio and viscosity of gel; thickness of gel; ability to transfer gel filling into existing LSR process; ability to create a void or cavity in LSR layer; and/or ability to fill gel into void or cavity of LSR layer.

3.2.1 Over-Molding

FIGS. 209-1 to 209-5 illustrate an over-molding process for manufacturing a gel-filled LSR cushion according to an embodiment of the present invention. This process includes three consecutive steps which all occur within the cushion mold, i.e., in-mold filling. Specifically, an LSR layer 7410 is molded in a mold including first and second mold parts 7425, 7426 (FIGS. 209-1 and 209-2), the first part 7425 is removed and a gel 7440 is mixed and poured (e.g., open pour or gravity fill) into the cavity defined by the LSR layer 7410 (FIG. 209-3), and then a third mold part 7427 is provided to the second mold part 7426 for over-molding a cap 7430 over the gel-filled layer 7410 (FIGS. 209-4 and 209-5). The gel 7440 is cured before over-molding the cap 7430 to the LSR layer 7410. As illustrated, the ends of the layer 7410 provide a relatively flat back or support for engaging the cap.

In this embodiment, a high temperature curing gel (e.g., silicone) may be used to withstand the LSR temperatures and control cure time. Also, the cap may be molded of an LSR material using low pressure injection molding.

It should be appreciated that the cushion mold is merely schematic and each mold part may include multiple components to facilitate molding/demolding.

For example, FIG. 211 illustrates a method of molding a gel cushion according to an embodiment of the present invention. Further details of such method are described in European Patent Application No. EP 08160921.6, filed 22 Jul. 2008, which is incorporated herein by reference in its entirety.

As illustrated, three mold parts 7511, 7512 and 7513 are provided. They are moveable with respect to each other. Thus, the mold can be opened and closed. Mold half 7513 is designed complementary to the cushion's upper side and to its inner side such as inner wall 7505*b*. Mold half 7511 is designed complementary to the cushion's outer circumference and part of the cushion's lower side. Stamp 7512 is designed complementary to the remainder of the cushion's lower side and is adapted to form sealing lip 7506.

Furthermore, a core 7515 is provided within the mold formed by the mold parts 7511, 7512 and 7513. The core is preferably C-shaped and mounted on or comprises a handling member 7514 such as, e.g., a rod. Preferably, core 7515 is substantially symmetrical with regard to the axis of the cushion to be molded. Preferably, core 7515 and member 7514 are integrally formed. Preferably, member 7514 is moveably connected to mold half 7513. Core 7515 can thus be displaced with respect to the mold parts 7511, 7512 and 7513.

After closing the mold, a first material is injected into the mold through gate 7516. The first material is cured or at least partially cured and thus a cushion 7501 is formed. The core 7515 is enclosed by the cushion 7501 and thus forms a cavity 7504 therein. Handling member 7514 extends through orifice 7503 to the outside of cushion 7501. The mold is then opened by moving, e.g., mold parts 7511 and 7512 away from mold part 7513. The moveable part 7514 is then displaced with respect to mold part 7513, preferably leaving the core 7515 together with the cushion 7501 in a position without any contact to other mold parts. Now, the cushion 7501 may be removed from the core 7515. This may be achieved, e.g. by air pressure. For instance, member 7514 and core 7515 may comprise an air conduit for providing pressure. The cavity of the cushion 7501 formed by the core 7115 is thus inflated and the cushion 7501 can be easily detached from the core 7515. Alternatively, cushion 7501 can be mechanically pulled off the core 7515 without the provision of air pressure.

3.2.2 Co-Molding

FIGS. 210-1 to 210-6 illustrate a co-molding process for manufacturing a gel-filled LSR cushion according to an embodiment of the present invention. This process includes parallel molding steps and out-of-mold gel filling. Specifically, an LSR layer 7410 is molded in a first mold including first and second mold parts 7425, 7426 as shown FIGS. 210-3 and 210-4. In a second mold, as shown in FIG. 201-1, an LSR cap 7430 is molded in first and second mold parts 7427, 7428. The second mold part 7428 is removed to allow an adhesive 7435 to be applied to the base of the LSR cap 7430 as shown in FIG. 210-2. As shown in FIG. 210-5, the LSR cap 7430 is suitably located and bonded to the LSR layer 7410 via the adhesive 7435. Then, as shown in FIG. 210-6, a gel 7440 is injected into the cavity (e.g., via a hole in the cap 7430) defined between the LSR layer 7410 and cap 7430. The hole into the cavity is sealed with silicon.

In this embodiment, the gel is cured independent of molding, which allows the cure temperature of the gel to be independent from the LSR curing temperatures (e.g., polyurethane and silicone gels may be suitable). Such co-molding arrangement may be compatible with existing LSR processes.

In another embodiment, a pre-molded gel piece may be inserted into the cavity of the LSR layer, and then a cap may be attached or molded over the LSR layer (e.g., see FIG. 18 described above).

It should be appreciated that the cushion mold is merely schematic and each mold part may include multiple components to facilitate molding/demolding.

4. Alternative Gel Arrangements

The following illustrates alternative embodiments and configurations for gel cushions.

FIGS. 71 and 72 illustrate a spring mechanism 2585 attached to a gel cushion 2540 for bias. The spring mechanism 2585 is structured to act between the gel support or frame and the gel cushion. In an embodiment, the spring mechanism may be insertable to the gel cushion 2540 (see FIG. 73).

Figure 74:
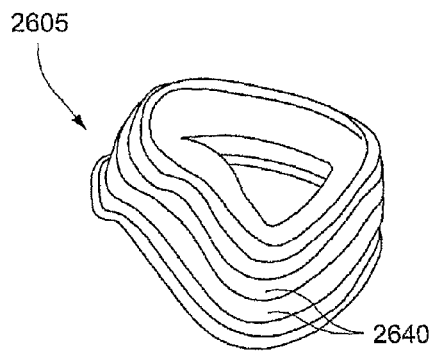
FIGS. 74 and 75 illustrate a cushion with multiple tubes of gel according to an embodiment of the present invention.
Figure 75:
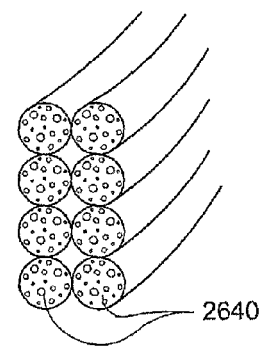

FIGS. 74 and 75 illustrate a cushion 2605 with multiple tubes of gel 2640 stacked to form the cushion. The tubes may have varying durometers, thicknesses, lengths, etc. A skin may be provided to the tubes for contacting the patient's face in use.

Figure 76:
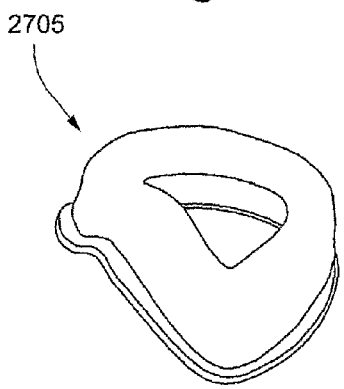
FIGS. 76 and 77 illustrates cushions with injected low durometer and high durometer gels according to an embodiment of the present invention.
Figure 77:
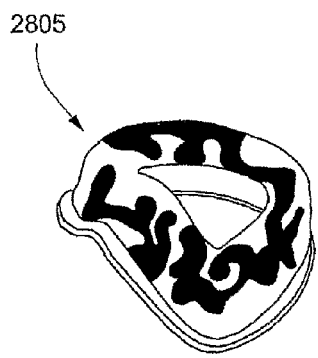

FIGS. 76 and 77 illustrates cushions 2705, 2805 with low durometer and high durometer gel injected simultaneously into the cushion. In an embodiment, different colored gels may be used to provide a color mix. For example, FIG. 76 shows a cushion 2705 with a low duro and high duro coinjection mix, and FIG. 77 shows a cushion 2805 with a low duro and high duro coinjection "marbled" effect.

Figure 78:
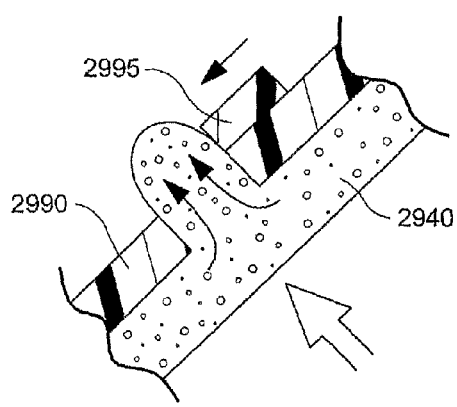
FIG. 78 illustrates a gel cushion with movable gel according to an embodiment of the present invention.

FIG. 78 illustrates a gel cushion 2940 in which the gel can move to outside of the frame 2990 when under pressure. A mechanical switch 2995 'forces' the gel back into the cushion to increase the bulk of the cushion. In an embodiment, multiple chambers may be provided around the mask, each chamber having a switch system so that user can modify pressure in each chamber to suit their face shape.

Figure 79:
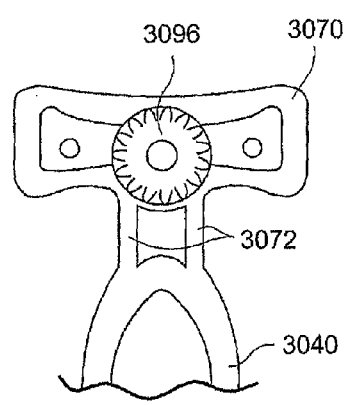
FIG. 79 illustrates a mask having a cam dial structured to release gel according to an embodiment of the present invention.

FIG. 79 illustrates a mask having a cam dial 3096 structured to release gel from a forehead pad reservoir 3070 so that it can flow down gel channels 3072 and into the cushion 3040, thereby increasing the volume of gel in the cushion. The user can customize the amount of gel in the cushion so that it is the right comfort level. In an embodiment, the reservoir may include water, air, or oil.

Figure 80:
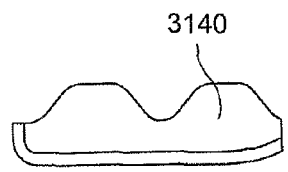
FIGS. 80 and 81 illustrate a gel cushion formed in two-dimensions and then wrapped around and locked together to form a three-dimensional cushion according to an embodiment of the present invention.
Figure 81:
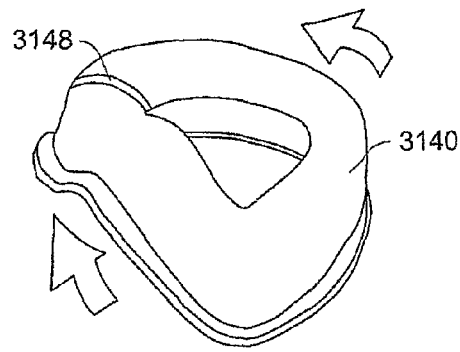

FIGS. 80 and 81 illustrate a gel cushion 3140 formed in two-dimensions (e.g., two-dimensional gel pouch) and then wrapped around and locked together to form a three-dimensional cushion. This arrangement allows the cushion to be sold in flat packs (see FIG. 80). The cushion joint 3148 may be joined by a clip, zip or any other suitable means.

FIG. 86 illustrates a gel 3440 that extends on either side of the sealing membrane 3410 to support it. The gel may cause the membrane to tend inwards and provide comfort. A clip mechanism 3480 (such as that shown in FIG. 87) may be provided to the gel for attachment to the frame 3490. The membrane 3410 could be co-molded to the center of the clip 3480 to minimize parts and aid assembly.

In an alternative embodiment, headgear and cushion for a mask may be molded as one part, with the one-piece headgear and cushion filled with gel or other material.

FIGS. 67 to 69 illustrate a cushion 2305 adapted to cover nose and mouth contacting portions as well as forehead pad. The cushion may have varying hardness throughout the cushion depending on zone.

In another alternative embodiment, the cushion may be structured such that temperature changes the size and/or shape of the cushion.

In another alternative embodiment, the cushion may be constructed of multiple cushions. Some cushions may only be partial cushions to support/comfort certain areas of the face. The multiple cushions may have different hardnesses, textures, colors, and/or dimensions. In an embodiment, the multiple cushions may be stackable to provide a stack-a-cushion arrangement, e.g., keep adding more cushions until mask is comfortable or fits better.

Figure 105:
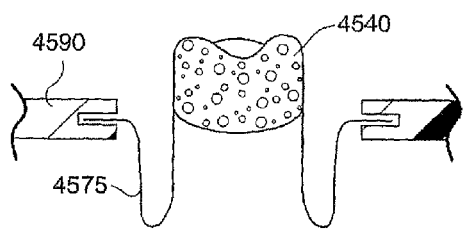
FIG. 105 illustrates a mask with a gusset provided between a gel cushion and a frame according to an embodiment of the present invention.

FIG. 105 illustrates a mask with a gusset 4575 provided between a gel cushion 4540 and a frame 4590 (e.g., like ResMed's Activa mask). In the illustrated embodiment, only a portion of the cushion at the top is filled with gel. In an embodiment, the gusset is springier than known gussets as the weight of the gel may require more force to move it back and forth.

Figure 132:
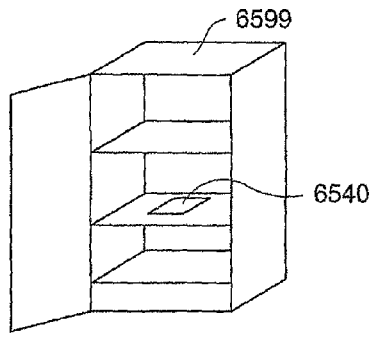

FIG. 132 illustrates a gel cushion wherein the gel section 6540 has an ice-pack arrangement that allows it to cool down before use. For example, the gel section 6540 may be placed in the fridge or freezer 6599 before use, e.g., for warm nights. Equally, the cushion may provide a heat-pack arrangement wherein the gel section may be heated before use.

Figure 133:
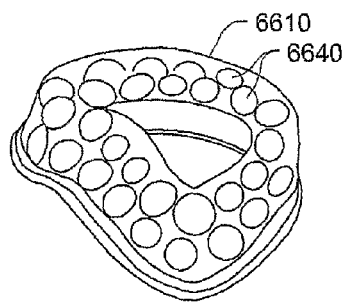
Figure 134:
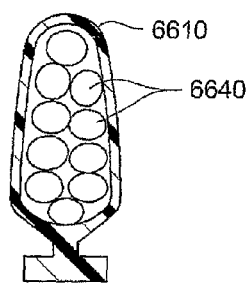

FIGS. 133 and 134 illustrate a cushion wherein small balls of low durometer gel 6640 are encased in a polyurethane or silicone cushion pouch 6610. In an alternative embodiment, the cushion may use foam balls.

Figure 135:
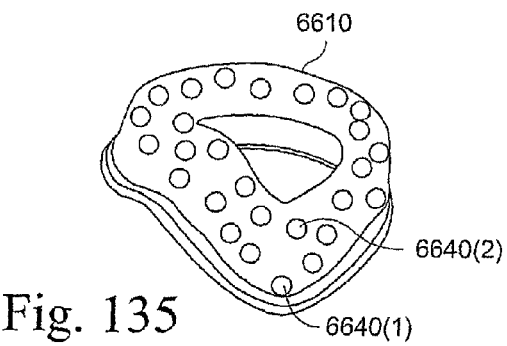
Figure 136:
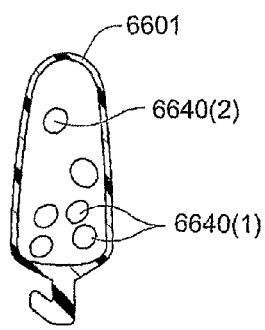

FIGS. 135 and 136 illustrate a cushion with small gel/foam balls encased in a cushion pouch, and wherein higher durometer balls 6640(1) are positioned at the bottom of the pouch 6610 and lower durometer balls 6640(2) are positioned at the top of the pouch 6610.

Figure 137:
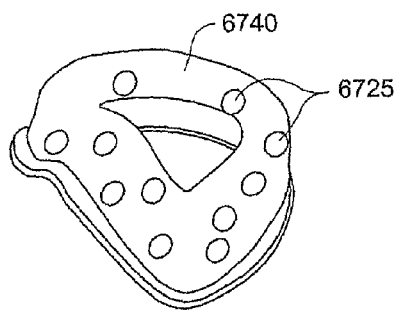

FIG. 137 illustrates a cushion with air bubbles 6725 provided within a high durometer gel 6740. The air bubbles alter the spring characteristics of the gel. In an embodiment, the cushion may change color when squashed, which could indicate high force areas.

Figure 138:
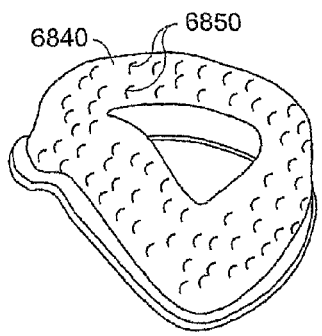

FIG. 138 illustrates a cushion including a high durometer gel foam 6840 filled or injected with a low durometer gel 6850. Such cushion may act like a "wet sponge" in use.

Figure 139:
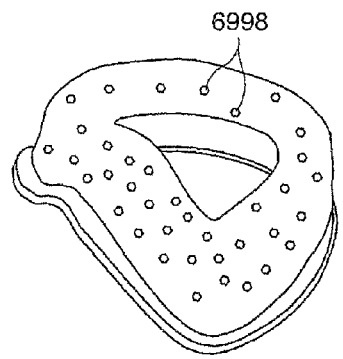

FIG. 139 illustrates a cushion with glitter 6998 added for aesthetics. The glitter could also indicate areas of high force.

Figure 140:
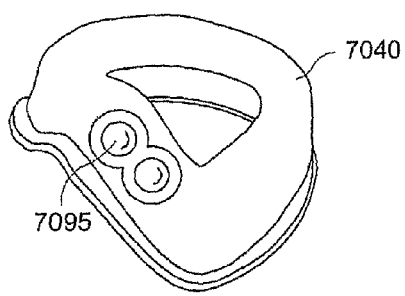

FIG. 140 illustrates a low durometer gel cushion 7040 with a mechanical finger pump 7095. The pump may be controlled by the patient to pump gel around the different areas of the cushion for a custom fit. The pump may be an oil, air or water pump.

In an alternative embodiment, the cushion may be constructed of a super tacky or sticky gel so that no headgear may be needed to maintain the cushion in position on the patient's face.

In another alternative embodiment, the cushion may include an atypical "skin", e.g., talc, spray-on skin.

Figure 141:
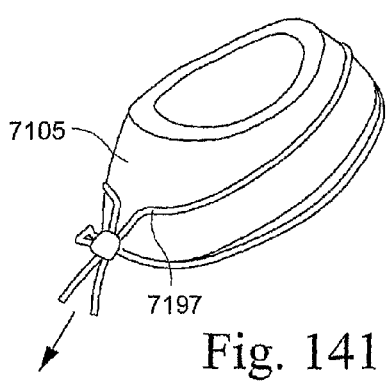

FIG. 141 illustrates a cushion 7105 including a draw string 7197 that is structured to pull the cushion inwards or outwards, e.g., change the size of the cushion opening. This arrangement may allow the cushion to be one size fits all, i.e., user adjusts draw string to suit their face.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A patient interface, comprising:
a cushioning structure including at least one hollow chamber filled with first and second discrete and/or layered filling materials, the first filling material being softer and/or more comfomable than the second filling material to provide patient comfort in use, and the first filling material adapted to be positioned closer to the patient's face in use; and
a seal forming structure formed in one piece with the cushioning structure, the seal forming structure including a thin membrane flap that is structured to provide a seal to the patient's face, the thin membrane flap including a free end that is spaced from the cushioning structure in its substantially relaxed, unstressed state and is adapted to be responsive to a difference between mask pressure and ambient pressure to effect a seal with a face region of a patient,
wherein the chamber extends only around a portion of the perimeter of the cushioning structure such that the chamber with first and second filling materials is provided in cheek and lip regions of the cushioning structure and a solid silicone portion is provided in a nasal bridge region of the cushioning structure.

2. A patient interface according to claim 1, wherein spacing between the free end of the thin membrane flap and the cushioning structure is different in different regions of the patient interface.

3. A patient interface according to claim 1, wherein the cushioning structure and the thin membrane flap include adjacent surfaces that face one another and are spaced apart from one another by a gap.

4. A patient interface according to claim 1, wherein the first and second filling materials are gel or gel-like materials.

5. A patient interface according to claim 1, wherein the second filling material provides support and structure to the first filling material.

6. A patient interface according to claim 1, wherein the cushioning structure and seal forming structure are molded of LSR.

7. A patient interface according to claim 1, wherein a width of each of the first and second filling materials is the same as a width of the chamber.

8. A patient interface according to claim 1, wherein the cushioning structure is a nasal cushion, and the chamber with first and second filling materials is provided in cheek and upper lip regions of the cushion.

9. A patient interface according to claim 1, wherein the first filling material and the second filling material are stacked in an axial direction.

10. A patient interface according to claim 1, wherein the chamber is oriented, curved, or contoured towards a breathing chamber of the patient interface to encourage bending or rolling towards the breathing cavity in use.

11. A patient interface according to claim 1, wherein a ratio of height of the first filling material to the second filling material is different in different regions of the cushioning structure along its perimeter.

12. A patient interface according to claim 1, wherein the first filling material has a Shore 000 hardness in the range of about 10 to about 20 and the second filling material has a Shore 000 hardness greater than about 45.

13. A patient interface according to claim 1, wherein the first filling material has a Shore 000 hardness in the range of about 10 to about 15 and the second filling material has a Shore 000 hardness in the range of about 50 to about 60.

14. A patient interface according to claim 1, wherein the seal forming structure is provided along the entire perimeter of the cushioning structure such that the thin membrane flap substantially covers the chamber and solid silicone portion of the cushioning structure.

15. A patient interface according to claim 1, wherein each of the chamber and the solid silicone portion includes a free end portion that curves inwardly towards a breathing chamber of the patient interface.

16. A patient interface according to claim 1, wherein walls of the chamber, the thin membrane flap, and the solid silicone portion are molded as a one piece component.

17. A patient interface according to claim 1, wherein the chamber and the solid silicone portion provide a continuous support and stability structure to the thin membrane flap along the entire perimeter of the cushioning structure.

* * * * *